United States Patent
Brodney et al.

(10) Patent No.: US 10,858,373 B2
(45) Date of Patent: Dec. 8, 2020

(54) HETEROCYCLIC SPIRO COMPOUNDS AS MAGL INHIBITORS

(71) Applicant: Pfizer Inc., New York, NY (US)

(72) Inventors: Michael Aaron Brodney, Newton, MA (US); Christopher Ryan Butler, Canton, MA (US); Laura Ann McAllister, Arlington, MA (US); Christopher John Helal, Mystic, CT (US); Steven Victor O'Neil, East Lyme, CT (US); Patrick Robert Verhoest, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/429,678

(22) Filed: Jun. 3, 2019

(65) Prior Publication Data

US 2019/0292203 A1    Sep. 26, 2019

Related U.S. Application Data

(63) Continuation of application No. 15/876,698, filed on Jan. 22, 2018, now abandoned.

(60) Provisional application No. 62/449,242, filed on Jan. 23, 2017.

(51) Int. Cl.

| | |
|---|---|
| *C07D 513/10* | (2006.01) |
| *A61P 37/00* | (2006.01) |
| *C07D 401/12* | (2006.01) |
| *C07D 471/10* | (2006.01) |
| *C07D 493/10* | (2006.01) |
| *C07D 498/10* | (2006.01) |
| *A61P 3/00* | (2006.01) |
| *A61P 9/00* | (2006.01) |
| *A61P 25/00* | (2006.01) |
| *A61P 35/00* | (2006.01) |
| *C07D 221/20* | (2006.01) |

(52) U.S. Cl.
CPC .............. *C07D 513/10* (2013.01); *A61P 3/00* (2018.01); *A61P 9/00* (2018.01); *A61P 25/00* (2018.01); *A61P 35/00* (2018.01); *A61P 37/00* (2018.01); *C07D 221/20* (2013.01); *C07D 401/12* (2013.01); *C07D 471/10* (2013.01); *C07D 493/10* (2013.01); *C07D 498/10* (2013.01)

(58) Field of Classification Search
CPC .................................................. C07D 513/10
USPC ........................................................ 514/278
See application file for complete search history.

(56) References Cited

U.S. PATENT DOCUMENTS

| | | | |
|---|---|---|---|
| 4,804,665 A | 2/1989 | Goto et al. | |
| 5,854,268 A | 12/1998 | Baker et al. | |
| 6,106,864 A | 8/2000 | Dolan et al. | |
| 6,599,900 B2 | 7/2003 | Cai et al. | |
| 6,642,257 B2 | 11/2003 | Yamamoto et al. | |
| 6,696,443 B2 | 2/2004 | Mavunkel et al. | |
| 7,225,679 B2 | 6/2007 | Miyagawa et al. | |
| 7,241,770 B2 | 7/2007 | Mentzel et al. | |
| 7,723,349 B2 | 5/2010 | Yao et al. | |
| 7,786,046 B2 | 8/2010 | Witschel et al. | |
| 7,825,147 B2 | 11/2010 | Palle et al. | |
| 7,863,279 B2 | 1/2011 | Even et al. | |
| 7,879,761 B2 | 2/2011 | Witschel et al. | |
| 8,394,787 B2 | 3/2013 | Abouabdellah et al. | |
| 8,415,341 B2 | 4/2013 | Chevalier et al. | |
| 8,513,423 B2 | 8/2013 | Connolly et al. | |
| 8,748,417 B2 | 6/2014 | Zhang et al. | |
| 8,772,318 B2 | 7/2014 | Cravatt et al. | |
| 8,835,418 B2 | 9/2014 | Bartsch et al. | |
| 9,133,148 B2 | 9/2015 | Cisar et al. | |
| 9,845,301 B2 | 12/2017 | Butler et al. | |
| 10,030,020 B2 * | 7/2018 | Cisar .................... C07D 471/10 |
| 2002/0151712 A1 | 10/2002 | Lin et al. | |
| 2007/0179167 A1 | 8/2007 | Cottrell et al. | |

(Continued)

FOREIGN PATENT DOCUMENTS

| | | |
|---|---|---|
| WO | 9111172 | 8/1991 |
| WO | 9402518 | 2/1994 |

(Continued)

OTHER PUBLICATIONS

Venkatesh, J. Pharm. Sci. 89, 145-54 (2000).*

(Continued)

*Primary Examiner* — Nizal S Chandrakumar
(74) *Attorney, Agent, or Firm* — Richard V. Zanzalari

(57) ABSTRACT

The present invention provides, in part, heterocyclic spiro compounds of Formula I:

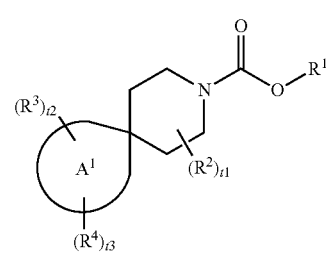

and pharmaceutically acceptable salts thereof; processes for the preparation of; intermediates used in the preparation of; and compositions containing such compounds or salts, and their uses for treating MAGL-mediated diseases and disorders including, e.g., pain, an inflammatory disorder, depression, anxiety, Alzheimer's disease, a metabolic disorder, stroke, or cancer.

17 Claims, No Drawings

(56) References Cited

U.S. PATENT DOCUMENTS

| | | | |
|---|---|---|---|
| 2007/0249648 | A1 | 10/2007 | Bladh et al. |
| 2009/0048247 | A1 | 2/2009 | Palle et al. |
| 2010/0035909 | A1 | 2/2010 | Andres-Gil et al. |
| 2010/0063081 | A1 | 3/2010 | Bradly |
| 2010/0113417 | A1 | 5/2010 | Reich et al. |
| 2010/0190687 | A1 | 7/2010 | Boyle et al. |
| 2010/0324011 | A1 | 12/2010 | Bian et al. |
| 2011/0166165 | A1 | 7/2011 | Neelamkavil et al. |
| 2012/0077797 | A1 | 3/2012 | Connolly et al. |
| 2012/0264749 | A1 | 10/2012 | Hadida-Ruah et al. |
| 2014/0017698 | A1 | 1/2014 | Wang |
| 2018/0065943 | A1 | 3/2018 | Butler et al. |

FOREIGN PATENT DOCUMENTS

| | | |
|---|---|---|
| WO | 9855148 | 12/1998 |
| WO | 2000/035298 | 6/2000 |
| WO | 01011968 | 2/2001 |
| WO | 2008/130581 | 10/2008 |
| WO | 2009060030 | 5/2009 |
| WO | 2010/074588 | 7/2010 |
| WO | 2011142359 | 11/2011 |
| WO | 2012173174 | 12/2012 |
| WO | 2013/103973 | 7/2013 |
| WO | 2013131010 | 9/2013 |
| WO | 2014074715 | 5/2014 |
| WO | 2015/104343 | 7/2015 |
| WO | 2016/149401 | 9/2016 |
| WO | 2017/197192 | 11/2017 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*
Venkatesh et al, "Role of the Development Scientist in Compound Lead Selection and Optimization", Journal of Pharmaceutical Sciences, vol. 89(2), pp. 145-154 (2000).
Patel, et al: "Loratadine analogues as MAGL inhibitors", Bioorganic & Medicinal Chemistry Letters, vol. 25, No. 7, pp. 1436-1442 (2015).
Almarsson et al., "Crystal engineering of the composition of pharmaceutical phases. Do pharmaceutical co-crystals represent a new path to improved medicines?", Chem. Commun. 2004, 17, 1889-1896.
Bridgeman et al., "A Simple Method for the Preparation of Di-, Tri- and Tratrasubstituted Non-Symmetrical Ureas", Synlett 2006, 243-246.
Finnin et al., "Transdermal Penetration Enhancers: Applications, Limitations, and Potential", J. Pharm. Sci. 1999, 88, 955-958.
Flack, "On Enantiomorph-Polarity Estimation", Acta Cryst. 1983, A39, 867-881.
Freedman, et al., "Absolute Configuration Determination of Chiral Molecules in the Solution State Using Vibrational Circular Dichroism", Chirality 2003, 15, 743-758.
Haleblian, "Characterization of Habits and Crystalline Modification and Solids and their Pharmaceutical Applications", J. Pharm. Sci. 1975, 64, 1269-1288.
Hooft et al., "Determination of absolute structure using Bayesian statistics on Bijvoet differences", J. Appl. Cryst. 2008, 41, 96-103.
Mechoulam, et al., "Identification of an endogenous 2-monoglyceride, present in canine gut, that binds to cannabinoid receptors" Biochem. Pharmacol., 50 (1995), 83-90.
Macrae, et al., "Mercury: visualization and analysis of crystal structures", Appl. Cryst. 2006, 39, 453-457.
Dolomanov, et al., "OLEX2: a complete structure solution, refinement and analysis program", J. Appl. Cryst. 2009, 42, 339-341.
Spek, "Single-crystal structure validation with the program PLATON", J. Appl. Cryst. 2003, 36, 7-13.
Senczyszyn, et. al, "Spirocyclic Dihydropyridines by Electrophile-Induced Dearomatizing Cyclization of N-Alkenyl Pyridinecarboxamides"; Organic Letters (2013), 15(8), 1922-1925.
Sugiura et al., "2-Arachidonoylglycerol: a possible endogenous cannabinoid receptor ligand in brain," Biochem. Biophys. Res. Commun., 215 (1995), 89-97.
Verma et al., "Current Status of Drug Delivery Technologies and Future Directions", Pharmaceutical Technology On-line, 25(2), 1-14 (2001).
Wang, et al., "A Fluorescence-Based Assay for Monoacylglycerol Lipase Compatible with Inhibitor Screening," Assay and Drug Development Technologies, 2008, vol. 6 (3) pp. 387-393.
Bioreversible Carriers in Drug Design, Pergamon Press, 1987 (Ed. E. B. Roche, American Pharmaceutical Association).
Crystals and the Polarizing Microscope by N. H. Hartshorne and A. Stuart, 4th Edition (Edward Arnold, 1970).
Design of Prodrugs by H. Bundgaard (Elsevier, 1985).
Greene and P. G. M. Wuts, Protective Groups in Organic Synthesis, 3rd Ed., Wiley & Sons, Inc., New York (1999).
Handbook of Pharmaceutical Salts: Properties, Selection, and Use by Stahl and Wermuth (Wiley-VCH, 2002).
Pro-drugs as Novel Delivery Systems, vol. 14, ACS Symposium Series (T. Higuchi and W. Stella).
Prodrugs: Challenges and Reward, 2007 edition, edited by Valentino Stella, Ronald Borchardt, Michael Hageman, Reza Oliyai, Hans Maag, Jefferson Tilley, 125-176 (Springer, 2007).
Remington's Pharmaceutical Sciences, 19th Edition (Mack Publishing Company, 1995).
Stereochemistry of Organic Compounds by E. L. Eliel and S. H. Wilen (Wiley, New York, 1994).
Bringmann, et al., Atroposelective Synthesis of Axially Chiral Biaryl Compounds. Angew. Chem., Int. Ed. 2005, 44, 5384-5427.
Jae Won Chang et al: "Highly Selective Inhibitors of Monoacylglycerol Lipase Bearing a Reactive Group that Is Bioisosteric with Endocannabinoid Substrates", Chemistry & Biology, vol. 19, No. 5, May 1, 2012 (May 1, 2012), pp. 579-588.

* cited by examiner

HETEROCYCLIC SPIRO COMPOUNDS AS MAGL INHIBITORS

This application is a continuation of U.S. patent application Ser. No. 15/876,698 filed Jan. 22, 2018, which in turn claims the benefit of priority to U.S. Provisional Patent Application Ser. No. 62/449,242 filed Jan. 23, 2017, the disclosure of each of which is hereby incorporated by reference in its entirety.

FIELD OF THE INVENTION

The present invention relates to novel heterocyclic spiro compounds, which are monoacylglycerol lipase (MAGL) inhibitors, pharmaceutical compositions thereof, and uses thereof in the treatment of MAGL-mediated disorders such as pain, an inflammatory disorder, depression, anxiety, Alzheimer's disease, a metabolic disorder, stroke, or cancer.

BACKGROUND OF THE INVENTION

MAGL is the principal enzyme responsible for the in vivo degradation of 2-arachidonoyl glycerol (2-AG), an endogenous ligand of the cannabinoid receptors (e.g., CB1 and CB2). See e.g., Patel, J. Z. et al., "Loratadine analogues as MAGL inhibitors," Bioorg. Med. Chem. Lett., 2015, 25(7): 1436-42; Mechoulam, R. et al., "Identification of an endogenous 2-monoglyceride, present in canine gut, that binds to cannabinoid receptors" Biochem. Pharmacol., 50 (1995), 83-90; Sugiura, T. et al., "2-Arachidonoylglycerol: a possible endogenous cannabinoid receptor ligand in brain," Biochem. Biophys. Res. Commun., 215 (1995), 89-97.

MAGL inhibitors are potentially useful for the treatment of a MAGL-mediated disease or disorder. Examples of MAGL-mediated diseases or disorders include a metabolic disorder (e.g., obesity); vomiting or emesis; nausea; an eating disorder (e.g., anorexia or bulimia); neuropathy (e.g., diabetic neuropathy, pellagric neuropathy, alcoholic neuropathy, Beriberi neuropathy); burning feet syndrome; a neurodegenerative disorder [multiple sclerosis (MS), Parkinson's disease (PD), Huntington's disease, Alzheimer's disease, amyotrophic lateral sclerosis (ALS), epilepsy, a sleep disorder, Creutzfeldt-Jakob disease (CJD), or prion disease]; a cardiovascular disease (e.g., hypertension, dyslipidemia, atherosclerosis, cardiac arrhythmias, or cardiac ischemia); osteoporosis; osteoarthritis; schizophrenia; depression; bipolar disease; tremor; dyskinesia; dystonia; spasticity; Tourette's syndrome; sleep apnea; hearing loss; an eye disease (e.g., glaucoma, ocular hypertension, macular degeneration, or a disease arising from elevated intraocular pressure); cachexia; insomnia; meningitis; sleeping sickness; progressive multifocal leukoencephalopathy; De Vivo disease; cerebral edema; cerebral palsy; withdrawal syndrome [alcohol withdrawal syndrome, antidepressant discontinuation syndrome, antipsychotic withdrawal syndrome, benzodiazepine withdrawal syndrome, cannabis withdrawal, neonatal withdrawal, nicotine withdrawal, or opioid withdrawal]; traumatic brain injury; spinal cord injury; seizures; excitotoxin exposure; ischemia [stroke, hepatic ischemia or reperfusion, CNS ischemia or reperfusion]; liver fibrosis, iron overload, cirrhosis of the liver; a lung disorder [asthma, allergies, COPD, chronic bronchitis, emphysema, cystic fibrosis, pneumonia, tuberculosis, pulmonary edema, lung cancers, acute respiratory distress syndrome, intersitital lung disease (ILD), sarcoidosis, idiopathic pulmonary fibrosis, pulmonary embolism, pleural effusion, or mesothelioma]; a liver disorder [acute liver failure, Alagille syndrome, hepatitis, enlarged liver, Gilbert's syndrome, liver cysts, liver hemangioma, fatty liver disease, steatohepatitis, primary sclerosing cholangitis, fascioliasis, primary bilary cirrhosis, Budd-Chiari syndrome, hemochromatosis, Wilson's disease, or transthyretin-related hereditary amyloidosis], stroke [e.g., ischemic stroke; hemorrhagic stroke]; subarachnoid hemorrhage; vasospasm; AIDS wasting syndrome; renal ischemia; a disorder associated with abnormal cell growth or proliferation [e.g., a benign tumor or cancer such as benign skin tumor, brain tumor, papilloma, prostate tumor, cerebral tumor (glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, bladder cancer, brain cancer, glioblastoma (GBM), gastrointestinal cancer, leukemia or blood cancer]; an autoimmune disease [e.g., psoriasis, lupus erythematosus, Sjögren's syndrome, ankylosing spondylitis, undifferentiated spondylitis, Behcet's disease, hemolytic anemia, graft rejection]; an inflammatory disorder [e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, IBS, pelvic inflammatory disease, sarcoidosis, HIV encephalitis, rabies, brain abscess, neuroinflammation, inflammation in the central nervous system (CNS)]; a disorder of the immune system (e.g., transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); Asperger's syndrome; pain [e.g., acute pain; chronic pain; inflammatory pain; visceral pain; post-operative pain; migraine; lower back pain; joint pain; abdominal pain; chest pain; postmastectomy pain syndrome; menstrual pain; endometriosis pain; pain due to physical trauma; headache; sinus headache; tension headache arachnoiditis, herpes virus pain, diabetic pain; pain due to a disorder selected from: osteoarthritis, rheumatoid arthritis, osteoarthritis, spondylitis, gout, labor, musculoskeletal disease, skin disease, toothache, pyresis, burn, sunburn, snake bite, venomous snake bite, spider bite, insect sting, neurogenic bladder, interstitial cystitis, urinary tract infection (UTI), rhinitis, contact dermatitis/hypersensitivity, itch, eczema, pharyngitis, mucositis, enteritis, irritable bowel syndrome (IBS), cholecystitis, and pancreatitis; neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy from chemotherapeutic agent, or sciatica pain)]; a demyelinating disease [e.g., multiple sclerosis (MS), Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis]; and cognitive impairment [e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)]. See e.g., U.S. Pat. No. 8,415,341, 8,835,418, or 8,772,318.

There continues to be a need for alternative MAGL inhibitors.

SUMMARY OF THE INVENTION

The present invention provides, in part, a novel compound of Formula I:

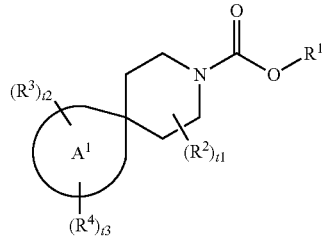

or a pharmaceutically acceptable salt thereof, wherein:
ring $A^1$ is $C_{4-7}$ cycloalkyl or 4- to 7-membered heterocycloalkyl;
$R^1$ is $R^{1A}$ or $R^{1B}$;
$R^{1A}$ is 1,1,1,3,3,3-hexafluoropropan-2-yl-;
$R^{1B}$ is 2,5-dioxopyrrolidin-1-yl-, which is optionally substituted with 1, 2, 3, or 4 (i.e., substituted with 0, 1, 2, 3, or 4) substituents each independently selected from the group consisting of the group consisting of halogen, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy;
each $R^2$ is independently selected from the group consisting of halogen, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy;
each $R^3$ is independently selected from the group consisting of —OH, oxo, halogen, —CN, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy;
$R^4$ is selected from the group consisting of $R^6$, —N($R^5$)(C(=O)$R^6$), —N($R^5$)(S(=O)$_2R^6$), —C(=O)—$R^6$, —S(=O)$_2R^6$, —N$R^5R^6$, —SO$_2$N$R^5R^6$, and —O$R^6$;
$R^5$ is selected from the group consisting of H, $C_{1-4}$ alkyl, $C_{3-4}$ cycloalkyl, and $C_{3-4}$ cycloalkyl-$C_{1-2}$ alkyl-;
$R^6$ is selected from the group consisting of $C_{1-6}$ alkyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, $C_{1-4}$ haloalkoxy, —C(=O)$C_{1-4}$ alkyl, —C(=O)OH, —C(=O)O—$C_{1-4}$ alkyl, —C(=O)NH$C_{1-4}$ alkyl, —C(=O)N($C_{1-4}$ alkyl)$_2$, —OC(=O)—$C_{1-4}$ alkyl, —OC(=O)O—$C_{1-4}$ alkyl, —NH$_2$, —NH($C_{1-4}$ alkyl), —N($C_{1-4}$ alkyl)$_2$, —NHC(=O)$C_{1-4}$ alkyl, —NHC(=O)OC$_{1-4}$ alkyl, and —NHC(=O)NH$C_{1-4}$ alkyl;
t1 is 0, 1, or 2;
t2 is 0, 1, 2, 3, or 4; and
t3 is 0 or 1.

In some embodiments, $R^1$ is $R^{1A}$. Accordingly, in such embodiments, the compound of Formula I or a pharmaceutically acceptable salt thereof is a compound of Formula I-1:

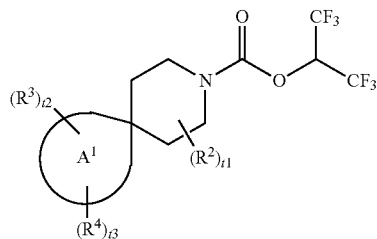

or a pharmaceutically acceptable salt thereof.

In some embodiments, $R^1$ is $R^{1B}$. Accordingly, in such embodiments, the compound of Formula I or a pharmaceutically acceptable salt thereof is a compound of Formula I-2:

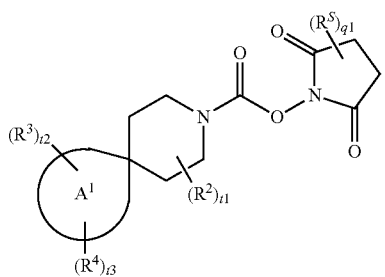

or a pharmaceutically acceptable salt thereof, wherein q1 is 0, 1, 2, 3, or 4; and each $R^S$ is independently selected from the group consisting of the group consisting of halogen, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments, $R^1$ is $R^{1B}$ and $R^{1B}$ is 2,5-dioxopyrrolidin-1-yl-. Accordingly, in such embodiments, the compound of Formula I or a pharmaceutically acceptable salt thereof is a compound of Formula I-2A:

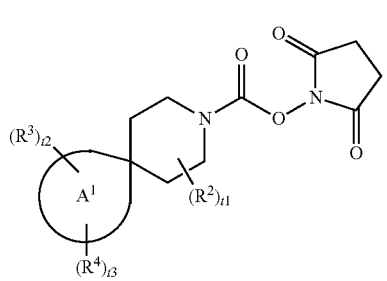

or a pharmaceutically acceptable salt thereof.

In the following embodiments described herein, unless otherwise indicated, each of these embodiments can be a compound of Formula I, I-1, I-2, or I-2A, or pharmaceutically acceptable salt thereof.

In some embodiments, ring $A^1$ is $C_{4-6}$ cycloalkyl or 4- to 6-membered heterocycloalkyl.

In some further embodiments, ring $A^1$ is $C_{4-6}$ cycloalkyl. In some yet further embodiments, ring $A^1$ is $C_4$ cycloalkyl (i.e. cyclobutyl).

In some embodiments, ring $A^1$ is $C_{4-6}$ cycloalkyl or 5- to 6-membered heterocycloalkyl.

In some embodiments, ring $A^1$ is 4- to 6-membered heterocycloalkyl. In some further embodiments, ring $A^1$ is 5- to 6-membered heterocycloalkyl.

In some embodiments, the moiety of Formula M-1 of Formula I (including the moiety of Formula M-1 of Formula I-1, Formula I-2, or Formula I-2A):

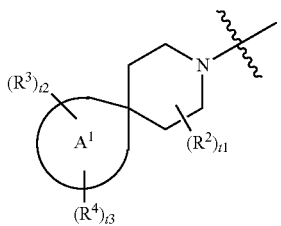

M-1 is a moiety of Formula M1-a:

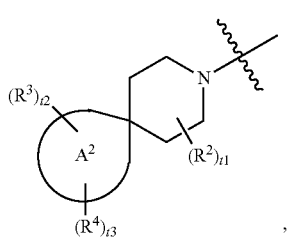

M-1a wherein ring $A^2$ is 5- or 6-membered heterocycloalkyl.

In some embodiments, the moiety of Formula M-1 of Formula I (including the moiety of Formula M-1 of Formula I-1, Formula I-2, or Formula I-2A) is a moiety of Formula M-1b, M-1c, M-1d, or M-1e:

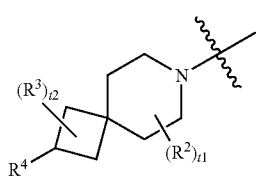

M-1b

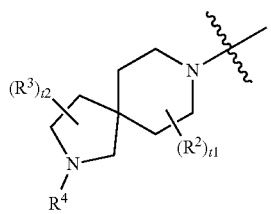

M-1c

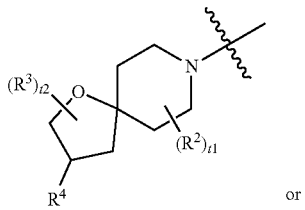

M-1d or

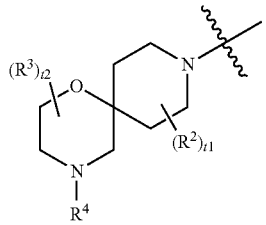

M-1e

In some embodiments, the moiety of Formula M-1 of Formula I (including the moiety of Formula M-1 of Formula I-1, Formula I-2, or Formula I-2A) is a moiety of Formula M-1b.

In some embodiments, the moiety of Formula M-1 of Formula I (including the moiety of Formula M-1 of Formula I-1, Formula I-2, or Formula I-2A) is a moiety of Formula M-1c.

In some embodiments, the moiety of Formula M-1 of Formula I (including the moiety of Formula M-1 of Formula I-1, Formula I-2, or Formula I-2A) is a moiety of Formula M-1d.

In some embodiments, the moiety of Formula M-1 of Formula I (including the moiety of Formula M-1 of Formula I-1, Formula I-2, or Formula I-2A) is a moiety of Formula M-1e.

In some embodiments, $R^2$ is halogen, methyl, or $C_1$ fluoroalkyl; t1 is 0 or 1; each $R^3$ is independently halogen, oxo, methyl, or $C_1$ fluoroalkyl; and t2 is 0, 1, or 2.

In some embodiments, t1 is 0.

In some embodiments, t2 is 0 or 1. In some further embodiments, t2 is 0.

In some embodiments, t1 is 0; t2 is 0 or 1; and t3 is 1. In some further embodiments, t1 is 0; t2 is 0; and t3 is 1.

In some embodiments, the moiety of Formula M-1 of Formula I (including the moiety of Formula M-1 of Formula I-1, Formula I-2, or Formula I-2A) is a moiety of Formula M-1b; and $R^4$ is selected from the group consisting of $R^6$, —N($R^5$)(C(=O)$R^6$), —N($R^5$)(S(=O)$_2R^6$), and —O$R^6$. In some further embodiments, $R^4$ is $R^6$ or —O$R^6$; and $R^6$ is selected from the group consisting of $C_{6-10}$ aryl (e.g. phenyl) and 5- to 10-membered heteroaryl (e.g. 5- to 6-membered heteroaryl such as pyridinyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-1, the moiety of Formula M-1 of Formula I-1 is a moiety of Formula M-1 b; $R^4$ is $R^6$ or —O$R^6$; and $R^6$ is selected from the group consisting of $C_{6-10}$ aryl (e.g. phenyl) and 5- to 10-membered heteroaryl (e.g. 5- to 6-membered heteroaryl such as pyridinyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some further embodiments, $R^4$ is —O$R^6$.

In some embodiments of the compound of Formula I-2 or I-2A, the moiety of Formula M-1 of Formula I-2 or I-2A is a moiety of Formula M-1b; $R^4$ is $R^6$ or —O$R^6$; and $R^6$ is selected from the group consisting of $C_{6-10}$ aryl (e.g. phenyl) and 5- to 10-membered heteroaryl (e.g. 5- to 6-membered heteroaryl such as pyridinyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some further embodiments, $R^4$ is —$OR^6$.

In some embodiments, the moiety of Formula M-1 of Formula I (including the moiety of Formula M-1 of Formula I-1, Formula I-2, or Formula I-2A) is a moiety of Formula M-1c; and $R^4$ is selected from the group consisting of $R^6$, —C(=O)—$R^6$, —S(=O)$_2R^6$, and —SO$_2NR^5R^6$. In some further embodiments, $R^4$ is —C(=O)—$R^6$. In some yet further embodiments, $R^6$ is selected from the group consisting of $C_{6-10}$ aryl (e.g. phenyl) and 5- to 10-membered heteroaryl (e.g. 5- to 6-membered heteroaryl such as pyridinyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments, the moiety of Formula M-1 of Formula I (including the moiety of Formula M-1 of Formula I-1, Formula I-2, or Formula I-2A) is a moiety of Formula M-1d; and $R^4$ is selected from the group consisting of $R^6$, —N($R^5$)(C(=O)$R^6$), —N($R^5$)(S(=O)$_2R^6$), —C(=O)—$R^6$, —S(=O)$_2R^6$, —NR$^5R^6$, —SO$_2NR^5R^6$, and —OR$^6$. In some further embodiments, $R^4$ is selected from the group consisting of $R^6$, —N($R^5$)(C(=O)$R^6$), and —N($R^5$)(S(=O)$_2R^6$). In some yet further embodiments, $R^5$ is H or $C_{1-4}$ alkyl; and $R^6$ is selected from the group consisting of $C_{1-6}$ alkyl, $C_{3-10}$ cycloalkyl, 4- to 10-membered heterocycloalkyl, $C_{6-10}$ aryl (e.g. phenyl), 5- to 10-membered heteroaryl (e.g. 5- or 6-membered heteroaryl), ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some still further embodiments, $R^5$ is H or $C_{1-4}$ alkyl; and $R^6$ is selected from the group consisting of $C_{6-10}$ aryl (e.g. phenyl), 5- to 10-membered heteroaryl (e.g. 5- or 6-membered heteroaryl such as pyridinyl or thiazolyl), and ($C_{3-10}$ cycloalkyl)-$C_{1-4}$ alkyl-; wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-1, the moiety of Formula M-1 of Formula I-1 is a moiety of Formula M-1d; and $R^4$ is selected from the group consisting of $R^6$, —N($R^5$)(C(=O)$R^6$), and —N($R^5$)(S(=O)$_2R^6$). In some further embodiments, $R^5$ is H or $C_{1-4}$ alkyl; and $R^6$ is selected from the group consisting of $C_{6-10}$ aryl (e.g. phenyl), 5- to 10-membered heteroaryl (e.g. 5- or 6-membered heteroaryl such as pyridinyl or thiazolyl), and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some still further embodiments, $R^4$ is $R^6$; and $R^6$ is selected from the group consisting of $C_{6-10}$ aryl (e.g. phenyl) and 5- to 10-membered heteroaryl (e.g. 5- or 6-membered heteroaryl such as pyridinyl or thiazolyl), wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-2 or I-2A, the moiety of Formula M-1 of Formula I-2 or I-2A is a moiety of Formula M-1d; and $R^4$ is selected from the group consisting of $R^6$, —N($R^5$)(C(=O)$R^6$), and —N($R^5$)(S(=O)$_2R^6$). In some further embodiments, $R^5$ is H or $C_{1-4}$ alkyl; and $R^6$ is selected from the group consisting of $C_{6-10}$ aryl (e.g. phenyl), 5- to 10-membered heteroaryl (e.g. 5- or 6-membered heteroaryl such as pyridinyl or thiazolyl), and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some still further embodiments, $R^4$ is $R^6$; and $R^6$ is selected from the group consisting of $C_{6-10}$ aryl (e.g. phenyl) and 5- to 10-membered heteroaryl (e.g. 5- or 6-membered heteroaryl such as pyridinyl or thiazolyl), wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-1, the moiety of Formula M-1 of Formula I-1 is a moiety of Formula M-1d; and $R^4$ is selected from the group consisting of —N($R^5$)(C(=O)$R^6$) and —N($R^5$)(S(=O)$_2R^6$). In some further embodiments, $R^5$ is H or $C_{1-4}$ alkyl; and $R^6$ is selected from the group consisting of $C_{6-10}$ aryl (e.g. phenyl), 5- to 10-membered heteroaryl (e.g. 5- or 6-membered heteroaryl such as pyridinyl or thiazolyl), and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-2 or I-2A, the moiety of Formula M-1 of Formula I-2 or I-2A is a moiety of Formula M-1d; and $R^4$ is selected from the group consisting of —N($R^5$)(C(=O)$R^6$) and —N($R^5$)(S(=O)$_2R^6$). In some further embodiments, $R^5$ is H or $C_{1-4}$ alkyl; and $R^6$ is selected from the group consisting of $C_{6-10}$ aryl (e.g. phenyl), 5- to 10-membered heteroaryl (e.g. 5- or 6-membered heteroaryl such as pyridinyl or thiazolyl), and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments, the moiety of Formula M-1 of Formula I (including the moiety of Formula M-1 of Formula I-1, Formula I-2, or Formula I-2A) is a moiety of Formula M-1e; and $R^4$ is selected from the group consisting of $R^6$, —C(=O)—$R^6$, —S(=O)$_2R^6$, and —SO$_2NR^5R^6$. In some further embodiments, $R^4$ is selected from the group consisting of $R^6$, —C(=O)—$R^6$, and —S(=O)$_2R^6$. In some yet further embodiments, $R^4$ is selected from the group consisting of $R^6$ and —S(=O)$_2R^6$.

In some embodiments, the moiety of Formula M-1 of Formula I (including the moiety of Formula M-1 of Formula I-1, Formula I-2, or Formula I-2A) is a moiety of Formula M-1e; and $R^4$ is —S(=O)$_2R^6$. In some further embodiments, $R^6$ is selected from the group consisting of $C_{6-10}$ aryl (e.g. phenyl) and 5- to 10-membered heteroaryl (e.g. 5- or 6-membered heteroaryl such as pyridinyl, piperazinyl, or thiazolyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some yet further embodiments, $R^6$ is 5- to 10-membered heteroaryl (e.g. 5- or 6-membered heteroaryl such as pyridinyl, piperazinyl, or thiazolyl), optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-1, the moiety of Formula M-1 of Formula I-1 is a moiety of Formula M-1e; and $R^4$ is —S(=O)$_2R^6$. In some further embodiments, $R^6$ is selected from the group consisting of $C_{6-10}$ aryl (e.g. phenyl) and 5- to 10-membered heteroaryl (e.g. 5- or 6-membered heteroaryl such as pyridinyl, piperazinyl, or thiazolyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some yet further embodiments, $R^6$ is 5- to 10-membered heteroaryl (e.g. 5- or 6-membered heteroaryl such as pyridinyl, piperazinyl, or thiazolyl), optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-2 or I-2A, the moiety of Formula M-1 of Formula I-2 or I-2A is a moiety of Formula M-1e; and $R^4$ is —S(=O)$_2R^6$. In some further embodiments, $R^6$ is selected from the group consisting of $C_{6-10}$ aryl (e.g. phenyl) and 5- to 10-membered heteroaryl (e.g. 5- or 6-membered heteroaryl such as pyridinyl, piperazinyl, or thiazolyl), wherein each of the selections is optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy. In some yet further embodiments, $R^6$ is 5- to 10-membered heteroaryl (e.g. 5- or 6-membered heteroaryl such as pyridinyl, piperazinyl, or thiazolyl), optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments, the moiety of Formula M-1 of Formula I (including the moiety of Formula M-1 of Formula I-1, Formula I-2, or Formula I-2A) is a moiety of Formula M-1e; and $R^4$ is $R^6$. In some further embodiments, $R^6$ is (4- to 10-membered heterocycloalkyl)-$C_{1-4}$ alkyl- [for example, (5- to 6-membered heterocycloalkyl)-$C_{1-4}$ alkyl-] optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-1, the moiety of Formula M-1 of Formula I-1 is a moiety of Formula M-1e; and $R^4$ is $R^6$. In some further embodiments, $R^6$ is (4- to 10-membered heterocycloalkyl)-$C_{1-4}$ alkyl- [for example, (5- to 6-membered heterocycloalkyl)-$C_{1-4}$ alkyl-] optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments of the compound of Formula I-2 or I-2A, the moiety of Formula M-1 of Formula I-2 or I-2A is a moiety of Formula M-1e; and and $R^4$ is $R^6$. In some further embodiments, $R^6$ is (4- to 10-membered heterocycloalkyl)-$C_{1-4}$ alkyl- [for example, (5- to 6-membered heterocycloalkyl)-$C_{1-4}$ alkyl-] optionally substituted with one or more (e.g. 0, 1, 2, 3, or 4) substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

In some embodiments, the present invention provides a compound selected from Examples 1 to 53 in the EXAMPLES section or a pharmaceutically acceptable salt thereof (or the parent compound thereof where the exemplary compound, for example, is a salt) herein below.

In some embodiments, the present invention provides a compound selected from the group consisting of:

1,1,1,3,3,3-hexafluoropropan-2-yl 4-[(4-fluorophenyl)sulfonyl]-1-oxa-4,9-diazaspiro[5.5]undecane-9-carboxylate;

1,1,1,3,3,3-hexafluoropropan-2-yl 4-(tetrahydro-2H-pyran-3-ylmethyl)-1-oxa-4,9-diazaspiro[5.5]undecane-9-carboxylate;

1-[({4-[(4-fluorophenyl)sulfonyl]-1-oxa-4,9-diazaspiro[5.5]undec-9-yl}carbonyl)oxy]pyrrolidine-2,5-dione;

1,1,1,3,3,3-hexafluoropropan-2-yl(3R)-3-[methyl(phenylsulfonyl)amino]-1-oxa-8-azaspiro[4.5]decane-8-carboxylate;

N-[(3R)-8-{[(2,5-dioxopyrrolidin-1-yl)oxy]carbonyl}-1-oxa-8-azaspiro[4.5]dec-3-yl]-N-methylbenzenesulfonamide;

1,1,1,3,3,3-hexafluoropropan-2-yl 3-(4-cyanophenyl)-1-oxa-8-azaspiro[4.5]decane-8-carboxylate;

1,1,1,3,3,3-hexafluoropropan-2-yl 2-{[6-(difluoromethyl)pyridin-3-yl]oxy}-7-azaspiro[3.5]nonane-7-carboxylate;

1,1,1,3,3,3-hexafluoropropan-2-yl 4-(pyrazin-2-ylsulfonyl)-1-oxa-4,9-diazaspiro[5.5]undecane-9-carboxylate;

1,1,1,3,3,3-hexafluoropropan-2-yl (3R)-3-[(phenylsulfonyl)amino]-1-oxa-8-azaspiro[4.5]decane-8-carboxylate;

1-cyclopropyl-N-[(3R)-8-{[(2,5-dioxopyrrolidin-1-yl)oxy]carbonyl}-1-oxa-8-azaspiro[4.5]dec-3-yl]-N-methylmethanesulfonamide;

1,1,1,3,3,3-hexafluoropropan-2-yl (3R)-3-{[(cyclopropylmethyl)sulfonyl](methyl)amino}-1-oxa-8-azaspiro[4.5]decane-8-carboxylate;

1,1,1,3,3,3-hexafluoropropan-2-yl 3-[methyl(1,3-thiazol-2-ylsulfonyl)amino]-1-oxa-8-azaspiro[4.5]decane-8-carboxylate;

1,1,1,3,3,3-hexafluoropropan-2-yl 3-[3-(trifluoromethoxy)phenyl]-1-oxa-8-azaspiro[4.5]decane-8-carboxylate; and 1-{[(2-{[6-(difluoromethyl)pyridin-3-yl]oxy}-7-azaspiro [3.5]non-7-yl)carbonyl]oxy}pyrrolidine-2,5-dione, or a pharmaceutically acceptable salt thereof.

The present invention includes any subset of any embodiment described herein.

The present invention includes combinations of two or more embodiments described hereinabove, or any subset thereof.

The present invention further provides the compound of Formula I or a pharmaceutically acceptable salt thereof (including all embodiments and combinations of two or more embodiments described herein or any subcombination thereof) for use in the treatment of a MAGL-mediated disease or disorder described herein.

The present invention further provides use of the compound of Formula I or a pharmaceutically acceptable salt thereof (including all embodiments and combinations of two or more embodiments described herein or any subcombination thereof) for treating a MAGL-mediated disease or disorder disorder described herein.

The present invention further provides a method for treating a MAGL-mediated disease or disorder in a patient (e.g., a mammal such as a human) comprising administering to the patient a therapeutically effective amount of the compound of Formula I or a pharmaceutically acceptable salt thereof (including all embodiments and combinations of two or more embodiments described herein or any subcombination thereof).

The present invention further provides use of the compound of Formula I or a pharmaceutically acceptable salt thereof (including all embodiments and combinations of two or more embodiments described herein or any subcombination thereof) in the manufacture of a medicament for use in the treatment of a MAGL-mediated disease or disorder described herein.

The compound of Formula I or a pharmaceutically acceptable salt thereof of the present invention (or a metabolite thereof) is a MAGL inhibitor. Thus, the present invention further provides a method for inhibiting MAGL (i.e., an activity of MAGL either in vitro or in vivo), comprising contacting (including incubating) the MAGL with the compound of Formula I or a pharmaceutically acceptable salt thereof (such as one selected from Examples 1-53 herein) described herein.

As used herein, the term "contacting" refers to the bringing together of indicated moieties in an in vitro system or an in vivo system. For example, "contacting" MAGL with a compound of the invention includes the administration of a compound of the present invention to an individual or patient, such as a human, having the MAGL, as well as, for example, introducing a compound of the invention into a sample containing a cellular or purified preparation containing the MAGL.

The amount of the compound of Formula I or a pharmaceutically acceptable salt thereof used in any one of the methods (or uses) of the present invention is effective in inhibiting MAGL.

MAGL-mediated diseases or disorders include, for example, a metabolic disorder (e.g., obesity); vomiting or emesis; nausea; an eating disorder (e.g anorexia or bulimia); neuropathy (e.g., diabetic neuropathy, pellagric neuropathy, alcoholic neuropathy, Beriberi neuropathy); burning feet syndrome; a neurodegenerative disorder [multiple sclerosis (MS), Parkinson's disease (PD), Huntington's disease, Alzheimer's disease, amyotrophic lateral sclerosis (ALS), epilepsy, a sleep disorder, Creutzfeldt-Jakob disease (CJD), or prion disease]; a cardiovascular disease (e.g., hypertension, dyslipidemia, atherosclerosis, cardiac arrhythmias, or cardiac ischemia); osteoporosis; osteoarthritis; schizophrenia; depression; bipolar disease; tremor; dyskinesia; dystonia; spasticity; Tourette's syndrome; sleep apnea; hearing loss; an eye disease (e.g., glaucoma, ocular hypertension, macular degeneration, or a disease arising from elevated intraocular pressure); cachexia; insomnia; meningitis; sleeping sickness; progressive multifocal leukoencephalopathy; De Vivo disease; cerebral edema; cerebral palsy; withdrawal syndrome [alcohol withdrawal syndrome, antidepressant discontinuation syndrome, antipsychotic withdrawal syndrome, benzodiazepine withdrawal syndrome, cannabis withdrawal, neonatal withdrawal, nicotine withdrawal, or opioid withdrawal]; traumatic brain injury; spinal cord injury; seizures; excitotoxin exposure; ischemia [stroke, hepatic ischemia or reperfusion, CNS ischemia or reperfusion]; liver fibrosis, iron overload, cirrhosis of the liver; a lung disorder [asthma, allergies, COPD, chronic bronchitis, emphysema, cystic fibrosis, pneumonia, tuberculosis, pulmonary edema, lung cancers, acute respiratory distress syndrome, intersitital lung disease (ILD), sarcoidosis, idiopathic pulmonary fibrosis, pulmonary embolism, pleural effusion, or mesothelioma]; a liver disorder [acute liver failure, Alagille syndrome, hepatitis, enlarged liver, Gilbert's syndrome, liver cysts, liver hemangioma, fatty liver disease, steatohepatitis, primary sclerosing cholangitis, fascioliasis, primary bilary cirrhosis, Budd-Chiari syndrome, hemochromatosis, Wilson's disease, or transthyretin-related hereditary amyloidosis], stroke [e.g., ischemic stroke; hemorrhagic stroke]; subarachnoid hemorrhage; vasospasm; AIDS wasting syndrome; renal ischemia; a disorder associated with abnormal cell growth or proliferation [e.g., a benign tumor or cancer such as benign skin tumor, brain tumor, papilloma, prostate tumor, cerebral tumor (glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, bladder cancer, brain cancer, glioblastoma (GBM), gastrointestinal cancer, leukemia or blood cancer]; an autoimmune disease [e.g., psoriasis, lupus erythematosus, Sjogren's syndrome, ankylosing spondylitis, undifferentiated spondylitis, Behcet's disease, hemolytic anemia, graft rejection]; an inflammatory disorder [e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, IBS, pelvic inflammatory disease, sarcoidosis, HIV encephalitis, rabies, brain abscess, neuroinflammation, inflammation in the central nervous system (CNS)]; a disorder of the immune system (e.g., transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); Asperger's syndrome; pain [e.g., acute pain; chronic pain; inflammatory pain; visceral pain; post-operative pain; migraine; lower back pain; joint pain; abdominal pain; chest pain; postmastectomy pain syndrome; menstrual pain; endometriosis pain; pain due to physical trauma; headache; sinus headache; tension headache arachnoiditis, herpes virus pain, diabetic pain; pain due to a disorder selected from: osteoarthritis, rheumatoid arthritis, osteoarthritis, spondylitis, gout, labor, musculoskeletal disease, skin disease, toothache, pyresis, burn, sunburn, snake bite, venomous snake bite, spider bite, insect sting, neurogenic bladder, interstitial cystitis, urinary tract infection (UTI), rhinitis, contact dermatitis/hypersensitivity, itch, eczema, pharyngitis, mucositis, enteritis, irritable bowel syndrome (IBS), cholecystitis, and pancreatitis; neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy from chemotherapeutic agent, or sciatica pain)]; a demyelinating disease [e.g., multiple sclerosis (MS), Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis]; and cognitive impairment [e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)].

The term "therapeutically effective amount" as used herein refers to that amount of the compound (including a pharmaceutically acceptable salt thereof) being administered which will relieve to some extent one or more of the symptoms of the disorder being treated. In reference to the treatment of a MAGL-mediated disease or disorder (e.g., Alzheimer's disease, inflammation, or pain), a therapeutically effective amount refers to that amount which has the effect of relieving to some extent (or, for example, eliminating) one or more symptoms associated with the MAGL-mediated disease or disorder (e.g., psychotic symptom of Alzheimer's disease).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

As used herein, the term "n-membered", where n is an integer, typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual sub-combination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). For yet another example, the term "$C_{1-4}$ alkyl" refers to linear or branched aliphatic hydrocarbon chains of 1 to 4 carbon atoms; the term "$C_{1-3}$ alkyl" refers to linear or branched aliphatic hydrocarbon chains of 1 to 3 carbon atoms; the term "$C_{1-2}$ alkyl" refers to methyl and/or ethyl; and the term "$C_1$ alkyl" refers to methyl. An alkyl group optionally can be substituted by one or more (e.g., 1 to 5) suitable substituents.

As used herein, the term "alkenyl" refers to aliphatic hydrocarbons having at least one carbon-carbon double bond, including straight chains and branched chains having at least one carbon-carbon double bond. In some embodiments, the alkenyl group has 2 to 20 carbon atoms, 2 to 10 carbon atoms, 2 to 6 carbon atoms, 3 to 6 carbon atoms, or 2 to 4 carbon atoms. For example, as used herein, the term "$C_{2-6}$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. When the compounds of Formula I contain an alkenyl group, the alkenyl group may exist as the pure E form, the pure Z form, or any mixture thereof.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl), decahydronaphthalenyl, etc.). The cycloalkyl group has 3 to 15 (e.g. 3 to 14, 3 to 10, 3 to 6, 3 to 4, or 4 to 6) carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_{3-10}$ cycloalkyl" refers to saturated or unsaturated, non-aromatic, monocyclic or polycyclic (such as bicyclic) hydrocarbon rings of 3 to 10 ring-forming carbon atoms (e.g., cyclopropyl, cyclobutyl, cyclopentyl, cyclohexyl, bicyclo[1.1.1]pentanyl, or cyclodecanyl); the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, bicyclo[1.1.1]pentan-1-yl, or bicyclo[1.1.1]pentan-2-yl); and the term "$C_{3-6}$ cycloalkyl" refers to saturated or unsaturated, non-aromatic, monocyclic or polycyclic (such as bicyclic) hydrocarbon rings of 3 to 6 ring-forming carbon atoms. For another example, the term "$C_{4-7}$ cycloalkyl" refers to saturated or unsaturated, non-aromatic, monocyclic or polycyclic (such as bicyclic) hydrocarbon rings of 4 to 7 ring-forming carbon atoms; the term "$C_{4-6}$ cycloalkyl" refers to saturated or unsaturated, non-aromatic, monocyclic or polycyclic (such as bicyclic) hydrocarbon rings of 4 to 6 ring-forming carbon atoms; and the term "$C_4$ cycloalkyl" refers to cyclobutyl. For yet another example, the term "$C_{3-4}$ cycloalkyl" refers to cyclopropyl or cyclobutyl. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-inden-1-yl, or 1H-inden-2(3H)-one-1-yl). The cycloalkyl group optionally can be substituted by 1 or more (e.g., 1 to 5) suitable substituents.

As used herein, the term "aryl" refers to all-carbon monocyclic or fused-ring polycyclic aromatic groups having a conjugated pi-electron system. The aryl group has 6 or 10 carbon atoms in the ring(s). Most commonly, the aryl group has 6 carbon atoms in the ring. For example, as used herein, the term "$C_{6-10}$ aryl" means aromatic ring radicals containing from 6 to 10 carbon atoms such as phenyl or naphthyl. The aryl group optionally can be substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono (i.e., =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the monocyclic heteroaryl ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like. The heteroaryl group optionally can be substituted by 1 or more (e.g., 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 12-membered ring system, 5- to 10-membered ring system, 4- to 7-membered ring system, 4- to 6-membered ring system, or 5- to 6-membered ring system), including 1 to 14 ring-forming carbon atoms and 1 to 10 ring-forming heteroatoms each independently selected from O, S and N (and optionally P or B when present). The heterocycloalkyl group can also optionally contain one or more oxo (i.e., =O) or thiono (i.e., =S) groups. For example, the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N; and the term "4- to 7-membered heterocycloalkyl" refers to a monocyclic or polycyclic, saturated or unsaturated, non-aromatic 4- to 7-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N; and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. The heterocycloalkyl group optionally can be substituted by 1 or more (e.g., 1 to 5) suitable substituents.

Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g., 2-oxaspiro[3.3]hept-6-yl}, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g., tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-6}$ haloalkyl" refers to a $C_{1-6}$ alkyl group having one or more halogen substituents (up to perhaloalkyl, i.e., every hydrogen atom of the alkyl group has been replaced by a halogen atom). For another example, the term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom); the term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom); and the term "$C_{1-2}$ haloalkyl" refers to a $C_{1-2}$ alkyl group (i.e., methyl or ethyl) having one or more halogen substituents (up to perhaloalkyl, i.e., every hydrogen atom of the alkyl group has been replaced by a halogen atom). For yet another example, the term "$C_1$ haloalkyl" refers to a methyl group having one, two, or three halogen substituents. Examples of haloalkyl groups include $CF_3$, $C_2F_5$, $CHF_2$, $CH_2F$, $CH_2CF_3$, $CH_2Cl$ and the like.

As used herein, the term "hydroxylalkyl" or "hydroxyalkyl" refers to an alkyl group having one or more (e.g., 1, 2, or 3) OH substituents. The term "$C_{1-6}$ hydroxylalkyl" or "$C_{1-6}$ hydroxyalkyl" refers to a $C_{1-6}$ alkyl group having one or more (e.g., 1, 2, or 3) OH substituents. The term "$C_{1-4}$ hydroxylalkyl" or "$C_{1-4}$ hydroxyalkyl" refers to a $C_{1-4}$ alkyl group having one or more (e.g., 1, 2, or 3) OH substituents; the term "$C_{1-3}$ hydroxylalkyl" or "$C_{1-3}$ hydroxyalkyl" refers to a $C_{1-3}$ alkyl group having one or more (e.g., 1, 2, or 3) OH substituents; and the term "$C_{1-2}$ hydroxylalkyl" or "$C_{1-2}$ hydroxyalkyl" refers to a $C_{1-2}$ alkyl group having one or more (e.g., 1, 2, or 3) OH substituents. An example of hydroxylalkyl is —$CH_2OH$ or —$CH_2CH_2OH$.

As used herein, the term "alkoxy" or "alkyloxy" refers to an —O-alkyl group. For example, the term "$C_{1-6}$ alkoxy" or "$C_{1-6}$ alkyloxy" refers to an —O—($C_{1-6}$ alkyl) group; and the term "$C_{1-4}$ alkoxy" or "$C_{1-4}$ alkyloxy" refers to an —O—($C_{1-4}$ alkyl) group; For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

As used here, the term "haloalkoxy" refers to an —O-haloalkyl group. For example, the term "$C_{1-6}$ haloalkoxy" refers to an —O—($C_{1-6}$ haloalkyl) group. For another example, the term "$C_{1-4}$ haloalkoxy" refers to an —O—($C_{1-4}$ haloalkyl) group; and the term "$C_{1-2}$ haloalkoxy" refers to an —O—($C_{1-2}$ haloalkyl) group. For yet another example, the term "$C_1$ haloalkoxy" refers to a methoxy group having one, two, or three halogen substituents. An example of haloalkoxy is —$OCF_3$ or —$OCHF_2$.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is optionally substituted, then up to 3 hydrogen atoms on the carbon atom can be replaced with substituent groups.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

As used herein, the point of attachment of a substituent can be specified to indicate the position where the substituent is attached to another moiety. For example, "($C_{3-7}$ cycloalkyl)-$C_{1-2}$ alkyl-" means the point of attachment occurs at the "$C_{1-2}$ alkyl" part of the "($C_{3-7}$ cycloalkyl)-$C_{1-2}$ alkyl-." For another example, "($C_{6-10}$ aryl)-$C_{1-2}$ alkyl-" means the point of attachment occurs at the "$C_{1-2}$ alkyl" part of the "($C_{6-10}$ aryl)-$C_{1-2}$ alkyl-."

As used herein, when a bond to a substituent is shown to cross a ring (or a bond connecting two atoms in a ring), then such substituent may be bonded to any of the ring-forming atoms in that ring that are substitutable (i.e., bonded to one or more hydrogen atoms), unless otherwise specified or otherwise implicit from the context. For example, as shown in Formula M-100 below, $R^3$ may be bonded to any of ring-forming atoms of ring $A^1$ (e.g. a nitrogen or carbon) that bears a hydrogen atom (e.g. NH or $CH_2$). For another example, as shown in Moiety M-200 below, an $R^3$ may be bonded to any ring-forming atom of the tetrahydrofuran ring that is substitutable (i.e., one of the carbon atoms of the —$CH_2$—$CHR^4$—$CH_2$— moiety of the tetrahydrofuran ring); but not on the piperidine ring of Moiety M-200 because the bond does not cross the piperidine ring. For yet another example, as shown in the structure of M-300, $R^{55}$ may be bonded to the nitrogen of (the NH) or one of the carbon atoms.

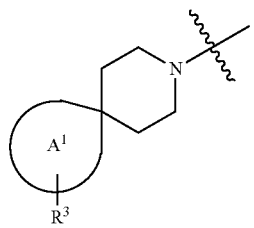

M-100

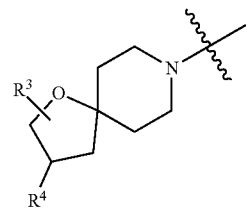

M-200

-continued

M-300
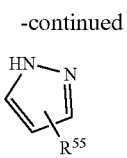

When a substituted or optionally substituted moiety is described without indicating the atom via which such moiety is bonded to a substituent, then the substituent may be bonded via any appropriate atom in such moiety. For example in a substituted arylalkyl, a substituent on the arylalkyl [e.g., $(C_{6-10}$ aryl)-$C_{1-4}$ alkyl-] can be bonded to any carbon atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I" or "Formula I or a pharmaceutically acceptable salt thereof" are defined to include all forms of the compound of Formula I or pharmaceutically salt thereof, including hydrates, solvates, isomers (including for example rotational stereoisomers), crystalline and non-crystalline forms, isomorphs, polymorphs, metabolites, and prodrugs thereof.

As is known to the person skilled in the art, amine compounds (i.e., those comprising one or more nitrogen atoms), for example tertiary amines, can form N-oxides (also known as amine oxides or amine N-oxides). An N-oxide has the formula of $(R^{100})(R^{200})(R^{300})N^+$—$O^-$ wherein the parent amine $(R^{100})(R^{200})(R^{300})N$ can be, for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100})(R^{200})(R^{300})N$ together forms 1-alkylpiperidine, 1-alkylpyrrolidine, 1-benzylpyrrolidine, or pyridine]. For instance, an imine nitrogen, especially a heterocyclic or heteroaromatic imine nitrogen, or pyridine-type nitrogen

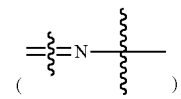

atom [such as a nitrogen atom in pyridine, pyridazine, or pyrazine], can be N-oxidized to form the N-oxide comprising the group

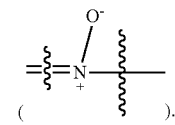

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

Compounds of Formula I and their salts described herein further include N-oxides thereof.

In the description herein below, unless otherwise specified, compounds of Formula I (or compounds of the invention) include salts of the compounds and the N-oxides of the compounds or the salts.

As is also known to the person skilled in the art, tertiary amine compounds (i.e., those comprising one or more tertiary amine nitrogen atoms) can form quaternary ammonium salts. In the description herein below, unless otherwise specified, compounds of Formula I (or compounds of the invention) further include their quaternary ammonium salts.

Compounds of Formula I may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components, which may be in stoichiometric or non-stoichiometric amounts. The resulting complexes may be ionized, partially ionized, or non-ionized. Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, Chem. Commun. 2004, 17, 1889-1896. For a general review of multi-component complexes, see J. K. Haleblian, J. Pharm. Sci. 1975, 64, 1269-1288.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of Formula I may themselves act as prodrugs of other compounds of Formula I.

Also included within the scope of the invention are metabolites of compounds of Formula I, that is, compounds formed in vivo upon administration of the drug.

The compounds of Formula I include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I (including salts thereof) may have asymmetric carbon atoms. The carbon-carbon bonds of the compounds of Formula I may be depicted herein using a solid line (—) a wavy line (∼∼∼), a solid wedge (◢), or a dotted wedge (⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. The use of a wavy line to depict bonds to asymmetric carbon atoms is meant to indicate that the stereochemistry is unknown (unless otherwise specified). It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of different types are possible. One type is the racemic compound (true racemate) wherein one homogeneous form of crystal is produced containing both enantiomers in equimolar amounts. Another type is a racemic mixture or conglomerate wherein two forms of crystal are produced in equal or different molar amounts each comprising a single enantiomer.

The compounds of Formula I may exhibit the phenomena of tautomerism and structural isomerism. For example, the compounds of Formula I may exist in several tautomeric forms, including the enol and imine form, the amide and imidic acid form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I. For example, when one of the following two tautomers (wherein R can be, for example, phenyl that is further substituted) is disclosed, those skilled in the art would readily recognize the other tautomer.

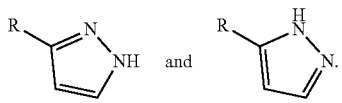

The present invention includes all pharmaceutically acceptable isotopically labelled compounds of Formula I or salts thereof wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically labelled compounds of Formula 1, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron-emitting isotopes, such as $^{11}$C, $^{18}$F, $^{15}$O and $^{13}$N, can be useful in Positron Emission Topography (PET) studies for examining substrate receptor occupancy.

Isotopically labeled compounds of Formula I can generally be prepared by conventional techniques known to those skilled in the art or by processes analogous to those described in the accompanying Examples and Preparations using an appropriate isotopically labeled reagent in place of the non-labeled reagent previously employed.

The present invention also provides compositions (e.g., pharmaceutical compositions) comprising a novel compound of Formula I. Accordingly, in one embodiment, the invention provides a pharmaceutical composition comprising (a therapeutically effective amount of) a novel compound of Formula I or a pharmaceutically acceptable salt thereof and optionally comprising a pharmaceutically acceptable carrier. In one further embodiment, the invention provides a pharmaceutical composition comprising (a therapeutically effective amount of) a compound of Formula I or a pharmaceutically acceptable salt thereof, optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I or salt thereof and a pharmaceutically acceptable carrier.

Compounds of Formula I (including salts thereof) are MAGL inhibitors. In some embodiments, the $IC_{50}$ of a compound of Formula I (or its metabolite) is less than about 10 µM, 5 µM, 2 µM, 1 µM, 500 nM, 200 nM, 100 nM, 50, 40, 30, 20, 10, 5, 2, or 1 nM as determined by the method in Example AA described herein below.

Administration of the compounds of Formula I (including salts thereof) may be effected by any method that enables delivery of the compounds to the site of action. These methods include, for example, enteral routes (e.g., oral routes, buccal routes, sublabial routes, sublingual routes), oral routes, intranasal routes, inhaled routes, intraduodenal routes, parenteral injection (including intravenous, subcutaneous, intramuscular, intravascular or infusion), intrathecal routes, epidural routes, intracerebral routes, intracerbroventricular routes, topical, and rectal administration.

In one embodiment of the present invention, the compounds of Formula I may be administered/effected by parenteral injection routes (e.g., intravenous injection route).

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with an at least one additional pharmaceutical or medicinal agent (e.g., an anti-schizophrenia agent), either sequentially or simultaneously.

The present invention includes the use of a combination of a compound of Formula I (including a salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including a pharmaceutically acceptable salt thereof); (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-ß (or fragments thereof), such as $Aß_{1-15}$ conjugated to pan HLA DR-binding epitope (PADRE) and ACC-001 (Elan/Wyeth);

(iii) antibodies to amyloid-ß (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-la (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 or M4 subtype) agonists such as bethanechol chloride (DUVOID, URECHOLINE);

(xxvi) neuroprotective drugs such as 2,3,4,9-tetrahydro-1H-carbazol-3-one oxime;
(xxvii) nicotinic receptor agonists such as epibatidine;
(xxviii) norepinephrine (noradrenaline) reuptake inhibitors such as atomoxetine (STRATTERA);
(xxix) phosphodiesterase (PDE) inhibitors, for example, PDE9 inhibitors such as BAY 73-6691 (Bayer AG) and PDE 10 (e.g., PDE10A) inhibitors such as papaverine;
(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));
(xxxi) quinolines such as quinine (including its hydrochloride, dihydrochloride, sulfate, bisulfate and gluconate salts);
(xxxii) β-secretase inhibitors such as WY-25105;
(xxxiii) γ-secretase inhibitors such as LY-411575 (Lilly);
(xxxiv) serotonin (5-hydroxytryptamine) 1A (5-HT$_{1A}$) receptor antagonists such as spiperone;
(xxxv) serotonin (5-hydroxytryptamine) 4 (5-HT$_4$) receptor agonists such as PRX-03140 (Epix);
(xxxvi) serotonin (5-hydroxytryptamine) 6 (5-HT$_6$) receptor antagonists such as mianserin (TORVOL, BOLVIDON, NORVAL);
(xxxvii) serotonin (5-HT) reuptake inhibitors such as alaproclate, citalopram (CELEXA, CIPRAMIL);
(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;
(xxxix) antihemorrhagic (i.e., hemostatic) agents such as rivaroxaban or apixaban;
and the like.

The compound of Formula I (including a salt thereof) is optionally used in combination with another active agent. Such an active agent may be, for example, an atypical antipsychotic or an anti-Parkinson's disease agent or an anti-Alzheimer's agent. Accordingly, another embodiment of the invention provides methods of treating a MAGL-mediated disease or disorder in a mammal, comprising administering to the mammal an effective amount of a compound of Formula I (including a pharmaceutically acceptable salt thereof) and further comprising administering another active agent.

As used herein, the term "another active agent" refers to any therapeutic agent, other than the compound of Formula I (including or a pharmaceutically acceptable salt thereof) that is useful for the treatment of a subject disorder. Examples of additional therapeutic agents include antidepressants, antipsychotics (such as anti-schizophrenia), anti-pain, anti-Parkinson's disease agents, anti-LID (levodopa-induced dyskinesia), anti-Alzheimer's, anti-anxiety, and antihemorrhagic agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical antidepressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine A$_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TAS- MAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NOR-FLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NOR-PRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional "another active agent" examples include rivastigmine (Exelon), Clozapine, Levodopa, Rotigotine, Aricept, Methylphenidate, memantine. milnacipran, guanfacine, bupropion, and atomoxetine. Examples of antihemorrhagic agents (including, e.g., coagulation factors, activators, or stabilizers) include Factor Xa inhibitors (e.g., rivaroxaban or apixaban) and recombinant Coagulation Factor VIIa (e.g., NovoSeven®).

As noted above, the compounds of Formula I or salts thereof may be used in combination with one or more additional anti-Alzheimer's agents which are described herein. When a combination therapy is used, the one or more additional anti-Alzheimer's agents may be administered sequentially or simultaneously with the compound of the invention. In one embodiment, the additional anti-Alzheimer's agent(s) is(are) administered to a mammal (e.g., a human) prior to administration of the compound of the invention. In another embodiment, the additional anti-Alzheimer's agent(s) is(are) administered to the mammal after administration of the compound of the invention. In another embodiment, the additional anti-Alzheimer's agent(s) is(are) administered to the mammal (e.g., a human) simultaneously with the administration of the compound of the invention (or a pharmaceutically acceptable salt thereof).

The invention also provides a pharmaceutical composition for the treatment of an inflammatory disorder (e.g., nueroinflammation) in a mammal, including a human, which comprises an amount of a compound of Formula I (including a salt thereof), as defined above (including hydrates, solvates and polymorphs of said compound or pharmaceutically acceptable salts thereof), in combination with one or more (for example one to three) anti-inflammation agents, wherein the amounts of the active agent and the combination when taken as a whole are therapeutically effective for treating the inflammatory disorder.

The invention also provides a pharmaceutical composition for treating a MAGL-mediated disease or disorder in a mammal, including a human, which comprises an amount of a compound of Formula I (including a salt thereof), as defined above (including hydrates, solvates and polymorphs of said compound or a salt thereof), in combination with one or more (for example one to three) other agents for treating the MAGL-mediated disease or disorder, wherein the amount of the active agents and the combination when taken as a whole are therapeutically effective for treating the MAGL-mediated disease or disorder.

It will be understood that the compounds of Formula I depicted above are not limited to a particular stereoisomer (e.g., enantiomer or diasteroisomer) shown, but also include all stereoisomers and mixtures thereof.

DETAILED DESCRIPTION OF THE INVENTION

Compounds of the invention, including salts of the compounds, can be prepared using known organic synthesis techniques and can be synthesized according to any of numerous possible synthetic routes. The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high-performance liquid chromatography (HPLC) or thin layer chromatography (TLC).

Compounds of Formula I, salts and intermediates thereof may be prepared according to the following reaction schemes and accompanying discussion. Unless otherwise indicated, $R^1$, $R^{1A}$, $R^{1B}$, $R^2$, $R^3$, $R^4$, $R^5$, $R^S$, ring $A^1$, t1, t2, t3, q1, and structural Formula I (including, e.g., I-1, I-2, I-2A) in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1 refers to synthesis of compounds of Formula I. A compound of Formula I (wherein $R^1$ is $R^{1A}$, i.e., 1,1,1,3,3,3-hexafluoropropan-2-yl-), also shown as a compound of Formula 1-4, can be prepared by reacting an amine of Formula 1-1 with a compound of Formula 1-2 [where $Lg^1$ a leaving group such as pentafluorophenoxy], in the presence of a base such as trimethylamine in a solvent such as acetonitrile. Alternatively, the amine of Formula 1-1 may be converted to the compound of Formula 1-4 by reaction with hexafluoroisopropanol (HFIP) of Formula 1-3 using standard methods of carbamate formation well known to those skilled in the art, for example, using a reagent such as phosgene, triphosgene, or a suitably activated carbonate reagent such as bis(pentafluorophenyl)carbonate or N,N'-disuccinimidyl carbonate.

Also shown in Scheme 1, a compound of Formula I (wherein $R^1$ is $R^{1B}$, i.e., 2,5-dioxopyrrolidin-1-yl-, which is optionally substituted with 1, 2, 3, or 4 substituents independently selected from the group consisting of the group consisting of halogen, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy), also shown as a compound of Formula 1-6, may be prepared by treatment of a compound of Formula 1-1 with an optionally substituted N,N'-disuccinimidyl carbonate 1-5 in the presence of a base such as N-methyl morpholine in a suitable solvent (e.g. a non-protic solvent such as dichloromethane). The amine of Formula 1-1 may be obtained commercially, synthesized by methods described herein, or made by other methods well known to those skilled in the art.

Scheme 2 refers to a synthesis of a spiromorpholine of Formula 2-6 (wherein $Pg^1$ is a suitable amine protecting group such as Boc), which can be used as an example of a compound of Formula 3-1 in Scheme 3. Referring to Scheme 2, reaction of a suitably protected 4-oxo-piperidine of Formula 2-1 with nitromethane in the presence of a base such as a mild base, for example, triethylamine affords a compound of Formula 2-2. Reduction of the nitro group of the compound of Formula 2-2 to obtain an aminoalcohol of Formula 2-3 can be achieved by using a method such as palladium-catalyzed hydrogenation, for example, utilizing 10% palladium on carbon in an alcoholic solvent under an atmosphere of hydrogen. Acetylation of the compound of Formula 2-3 can be achieved by treatment with chloroacetyl chloride in the presence of a suitable base such as potassium carbonate. Ring closure of the chloride compound of Formula 2-4 can be achieved by treatment with a suitable base (e.g., potassium tert-butoxide) in a non-protic solvent (e.g., THF) under reflux conditions to furnish a compound of Formula 2-5. The spiromorpholine compound of Formula 2-6 may be obtained by reduction of the amide (or the oxo) functionality in the compound of Formula 2-5, for example, using a suitable reducing agent (e.g. borane-dimethyl sulfide complex in THF).

Scheme 1

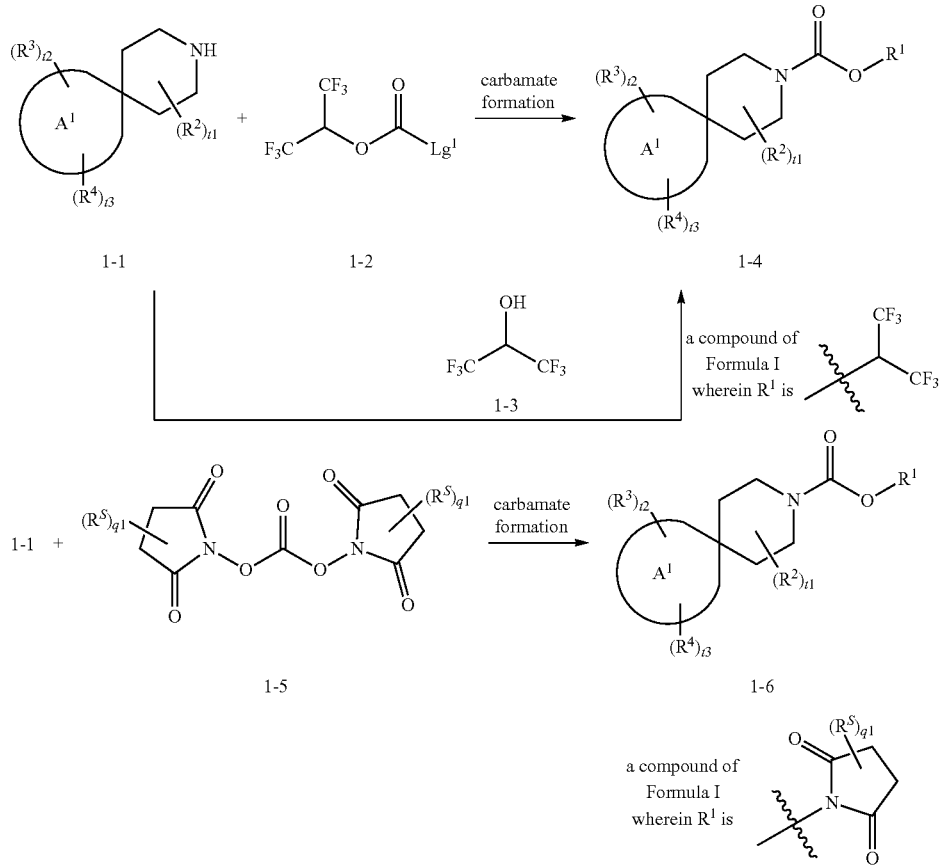

Scheme 2

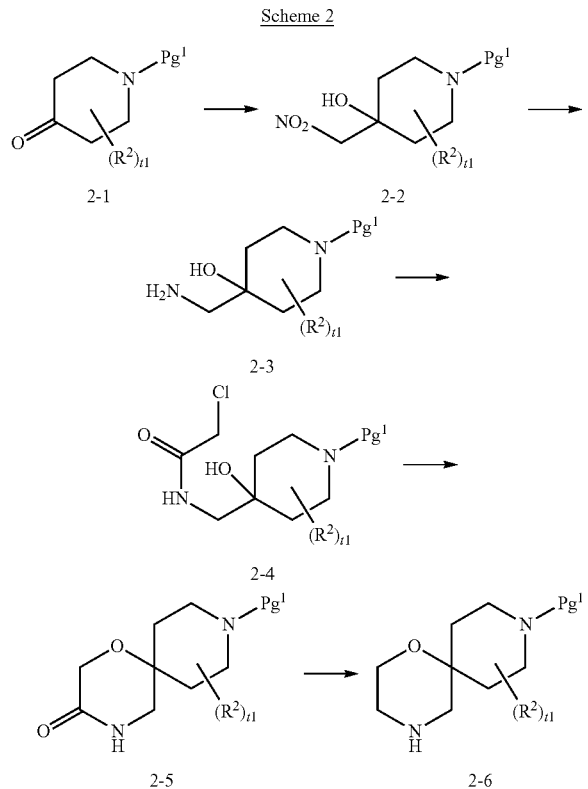

Scheme 3 refers to synthesis of an amine compound of Formula 3-4 or 3-7 from an amine of Formula 3-1. The amine of Formula 2-6 of Scheme 2 can be used as an example of the amine of Formula 3-1.

A compound of Formula 3-3 can be prepared by reacting the amine of Formula 3-1 with an aldehyde of Formula 3-2 [wherein $R^{64}$ can be, for example, selected from the group consisting of $C_{1-6}$ alkyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections is optionally substituted, for example, with 1, 2, 3, or 4 substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy] under reductive amination conditions well known to those skilled in the art. For example, treatment with titanium(IV) isopropoxide and a reducing agent such as sodium borohydride can be employed. Reaction of an amine of Formula 3-1 with a compound of Formula 3-5 (wherein $X^1$ is leaving group, for example, Cl) in the presence of a suitable base (such as pyridine or sodium bicarbonate) affords a sulfonamide of Formula 3-6. The compound of Formula 3-3 or 3-6, can be converted to a compound of Formula 3-4 or 3-7, respectively, by appropriate deprotection. For example, when $Pg^1$ is Boc, the deprotection can be achieved by treatment with an acid such as trifluoroacetic acid. The compound of Formula 3-4 or 3-7 can be used as as the amine of Formula 1-1 for synthesis of a compound of Formula I as described in Scheme 1.

Scheme 3

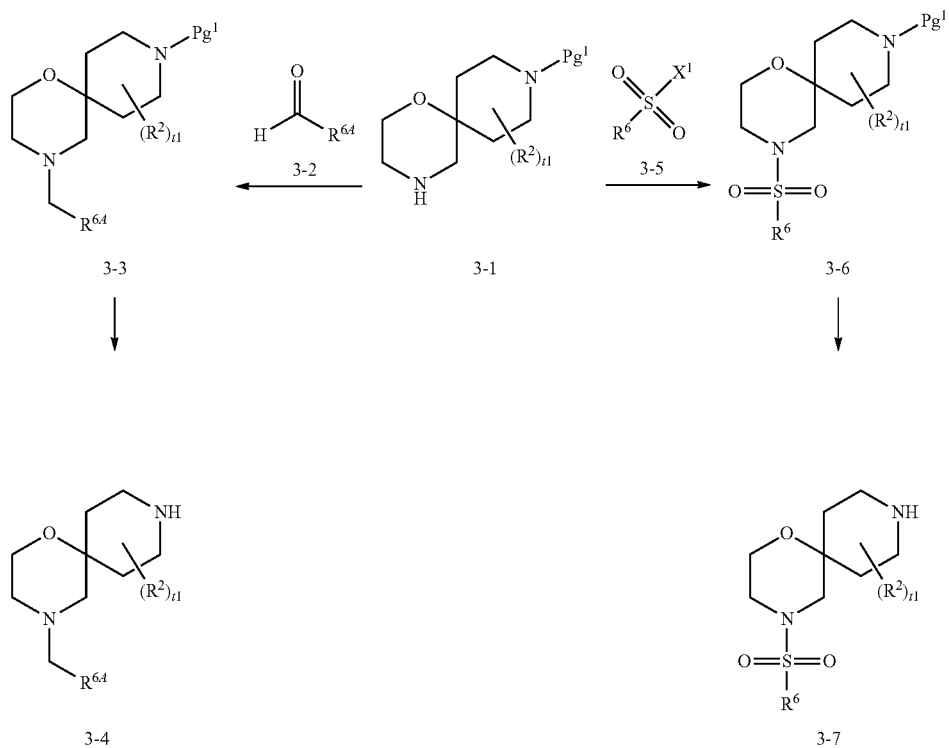

Scheme 4 refers to synthesis of an amine of Formula 4-9, which may be used as an amine compound of Formula 1-1 in Scheme 1. Referring to Scheme 4, a ketone of Formula 4-1 [wherein Pg$^1$ is a suitable amine protecting group such as Boc] may converted to an amine of Formula 4-2 using, for example, a biotransformation reaction, such as using a transaminase enzyme catalyst, an amine source, and an appropriate co-factor in aqueous buffer. For example, treatment of a solution of ketone of Formula 4-1 (in 4% DMSO/water solution) with Codex® ATA-200 transaminase catalyst, propan-2-amine, pyridoxal 5'-phosphate monohydrate in a pH 8 buffer solution (e.g. 0.1 M potassium phosphate, magnesium chloride) at a temperature such as 35° C. provides an amine of Formula 4-2. Appropriate selection of transaminase catalyst may afford a specific enantiomer of the amine of Formula 4-2. One skilled in the art may be able to prepare the compound of Formula 4-2 by alternative methods, one example of which can be conversion of a compound of Formula 6-3 in scheme 6 to a compound of Formula 4-2 by azide displacement and subsequent reduction. The compound of Formula 4-2 [wherein Pg$^2$ is another amine protecting group such as Alloc, which is preferably orthogonal to Pg$^1$] may be converted to a compound of Formula 4-3 under appropriate conditions depending on the nature of Pg$^2$ (and Pg$^1$) selected. For example, when Pg$^2$ is Alloc and Pg$^1$ is Boc, Pg$^2$ can be removed in an orthogonal manner to Pg$^1$. Optional alkylation of the compound of Formula 4-3 with a compound of Formula 4-4, for example, a halide compound (where X$^2$ is Cl, Br, or I) such as MeI, in the presence of a base such as sodium hydride, in an aprotic solvent such as DMF, gives a compound of Formula 4-5. Depending on the choice of protecting groups, Pg$^2$ may be removed by treatment with an appropriate reagent. For example, when Pg$^2$ is Alloc and Pg$^1$ is Boc, then the compound of Formula 4-5 may be treated with Tetrakis(triphenylphosphine)palladium(0) in the presence of 1,3-dimethylpyrimidine-2,4,6(1H,3H,5H)-trione, in a solvent such as THF to give a compound of Formula 4-6. Sulfonylation of the compound of Formula 4-6 with a compound of Formula 4-7 (wherein X$^1$ can be, for example, a halide such as chloride) in a suitable solvent (e.g., dichloromethane) in the presence of a suitable base (e.g., sodium bicarbonate) affords a compound of Formula 4-8. Pg$^1$ may be removed using a reagent, such as trifluoroacetic acid when Pg$^1$ is Boc, to give the compound of Formula 4-9.

Scheme 4

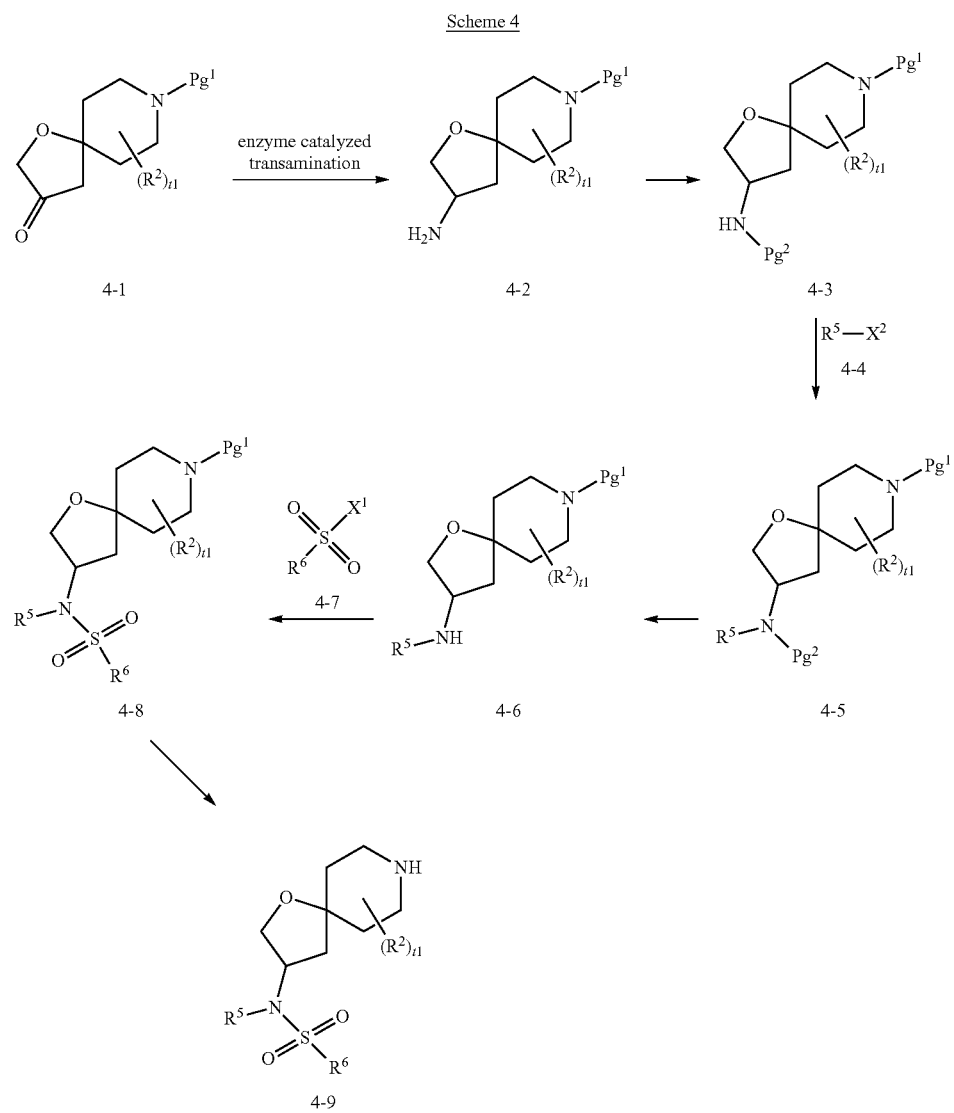

Scheme 5 refers to preparation of a compound of Formula 5-4, which can be used as an example of an amine of Formula 1-1 in Scheme 1. Referring to Scheme 5, a compound of Formula 5-1 [where Pg$^1$ is an amine protecting group (e.g., BOC)] can be obtained commercially, readily synthesized as described in Scheme 4, or using methods well known to those skilled in the art. A compound of Formula 5-3 can be obtained by reaction of a compound of Formula 5-1 with a compound of Formula 5-2 (wherein Lg$^2$ is a leaving group, for example, halide such as chloride) in a suitable solvent (e.g., dichloromethane) in the presence of a suitable base (e.g., sodium bicarbonate). Deprotection of the compound of Formula 5-3 using appropriate conditions well known to those skilled in the art provides the compound of Formula 5-4.

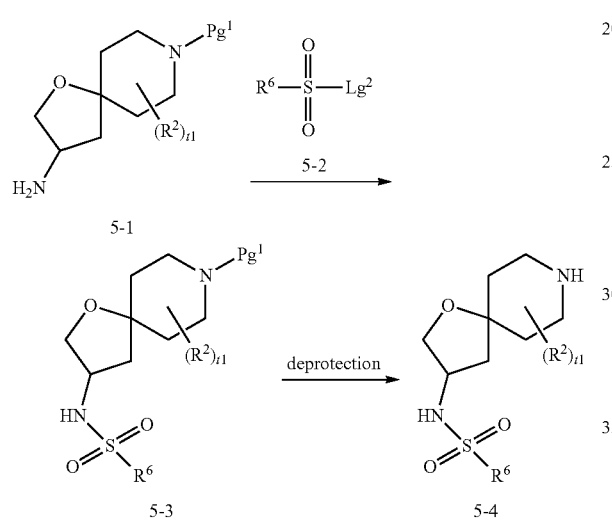

Scheme 6 refers to a method for synthesizing an amine compound of Formula 6-6, which may be used as an example of an amine of Formula 1-1 in Scheme 1. Bromination of an alkene of Formula 6-2 [where Pg$^1$ is an amine protecting group such as Boc] using Br$_2$ in a solvent such as dichloromethane gives a dibromide of Formula 6-2. Cyclization of the dibromide of Formula 6-2 to afford an bromide of Formula 6-3 may be achieved by treatment of the compound of Formula 6-2 with a base such as potassium carbonate, in a polar protic solvent such as methanol. Coupling of a boronic acid of Formula 6-4 [where each R is independently, for example, an optionally substituted alkyl; or two OR groups, together with the B atom to which they are attached, form an optionally substituted heterocylic ring] to the bromide of Formula 6-3 to form a compound of Formula 6-5 can be accomplished by using a catalyst such as nickel iodide and a strong base such as sodium bis (trimethylsilyl)amide, in the presence of a ligand such as trans-2-aminocyclohexanol. The reaction can be carried out in a protic solvent such as 2-propanol, at an elevated temperature (e.g. 60° C.). The protecting group can be removed from the compound of Formula 6-5 to give a compound of Formula 6-6, for example, by treatment with an organic acid such as trifluoroacetic acid when Pg$^1$ is Boc.

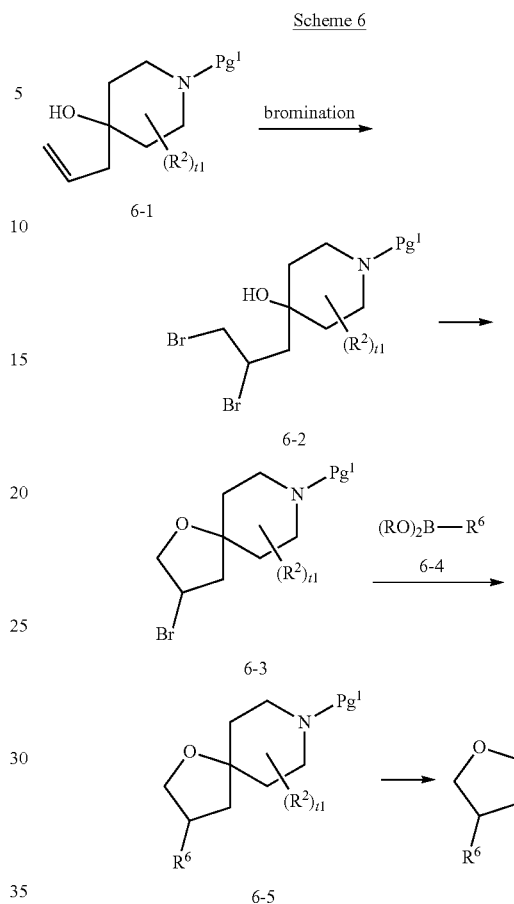

Scheme 7 refers to a method of preparation of an amine of Formula 7-4, which may be used as an example of a compound of Formula 1-1 in Scheme 1. Treatment of a compound of Formula 7-1 [where Pg$^1$ is an amine protecting group such as Boc; Y$^1$ is a leaving group such as Br, mesylate, or tosylate; and m is 1 or 2] with a 1H-pyrazole compound of Formula 7-2 (which is un-substituted on the 1-position, but is optionally substituted on the 3-, 4-, and/or 5-position; wherein t10 is 0, 1, 2, or 3; and each R$^{30}$ is, for example, independently selected from the group consisting of —CN, halogen, C$_{1-4}$ alkyl, C$_{3-6}$ cycloalkyl, C$_{1-4}$ alkoxy, C$_{1-4}$ haloalkyl, and C$_{1-4}$ haloalkoxy) in the presence of a base such as cesium carbonate, in a solvent such as DMF at an appropriate temperature (e.g. 80° C.) affords a compound of Formula 7-3. The protecting group Pg$^1$ may be cleaved under standard conditions to give the amine of Formula 7-4.

Scheme 7

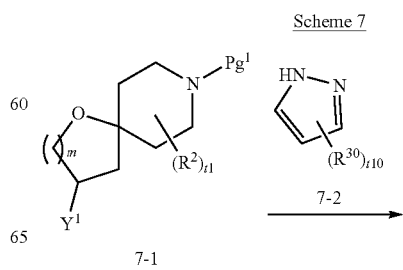

-continued

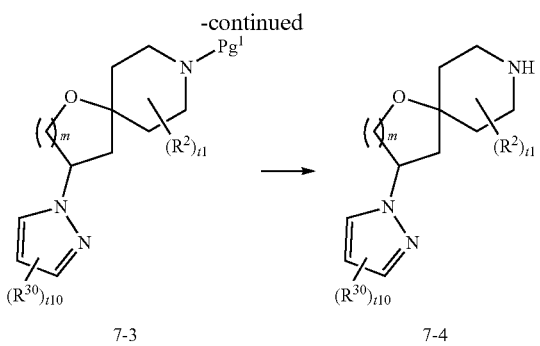

7-3     7-4

Scheme 8 refers to a synthesis of a heteroaryl ether or aryl ether of Formula 8-4. Mitsunobu reaction of an aryl or heteroaryl alcohol of Formula 8-2 with an alcohol of Formula 8-1 affords a compound of Formula 8-3 (wherein $Pg^1$ is an amine protecting group, e.g. Boc). Example Mitsunobu conditions include treatment with diisopropyl azodicarboxylate and triphenylphospine in an aprotic solvent such as THF, at an appropriate temperature, e.g. room temperature. Removal of $Pg^1$ from the compound Formula 8-3 then results in formation of the compound of Formula 8-4.

Scheme 8

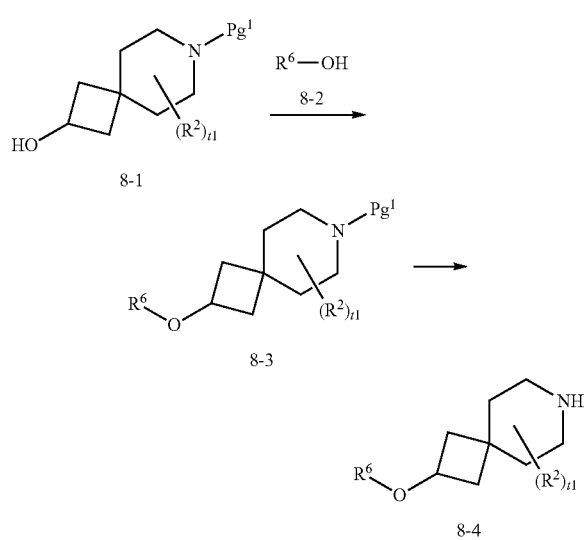

Additional starting materials and intermediates useful for making the compounds of the present invention can be obtained from chemical vendors such as Sigma-Aldrich or can be made according to methods described in the chemical art.

Those skilled in the art can recognize that in all of the schemes described herein, if there are functional (reactive) groups present on a part of the compound structure such as a substituent group, for example $R^1$, $R^{1A}$, $R^{1B}$, $R^2$, $R^3$, $R^4$, $R^5$, $R^S$, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion (CN⁻). For another example, an —S— can be oxidized to —S(=O)— and/or —S(=O)₂—. For yet another example, an unsaturated bond such as C=C or C≡C can be reduced to a saturated bond by hydrogenation. For yet another example, an amino group can be converted to an amide or sulfonamide group. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^1$, $R^2$, $R^3$, $R^4$, $R^5$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Cbz) or BOC/Boc group; conversion back to the $NH_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., Stereochemistry of Organic Compounds by E. L. Eliel and S. H. Wilen (Wiley, New York, 1994), the disclosure of which is incorporated herein by reference in its entirety. Suitable stereoselective techniques are well known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxpaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula I-a or I-b) may be prepared by, e.g., one or more of three methods:

(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s)

of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention (including pharmaceutically acceptable salts thereof) may be administered orally. Oral administration may involve swallowing, so that the compound enters the gastrointestinal tract, and/or buccal, lingual, or sublingual administration by which the compound enters the bloodstream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast-dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxides thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line,* 25(2), 1-14 (2001). The use of chewing gum to achieve controlled release is described in WO 00/35298.

The compounds of the invention (including pharmaceutically acceptable salts thereof) may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methyl cellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 μg to 200 mg, which may be administered in a single dose or, more usually, as divided doses throughout the day.

The compounds of the invention (including pharmaceutically acceptable salts thereof) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof, or a salt of such compound or prodrug; and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen on which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "pmol" means micromoles, "eq." means equivalent, "° C." means degrees Celsius, "MHz" means megahertz, "HPLC" means high-performance liquid chromatography.

EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers or diastereomers of certain compounds of the invention or their precursors/intermediates. In some examples, the separated enantiomers are designated as ENT-1 and ENT-2, according to their order of elution. In some examples, the separated diastereomers are designated as DIAST 1 and DIAST 2, according to their order of elution; and where desigations are determined for some precursors/intermediates, these designations are carried over to their subsequent products respectively. In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Abbreviations

The following are abbreviations which may appear in the experimental procedures or Schemes described herein:
BOC (or Boc)—tert-butoxycarbonyl
HPLC—high-performance liquid chromatography
Alloc—allyloxycarbonyl Preparations Preparations P1-P6 describe preparations of some starting materials or intermediates used for preparation of certain compounds of the invention.

Preparation P1 tert-Butyl 1-oxa-4,9-diazaspiro[5.5]undecane-9-carboxylate (P1)

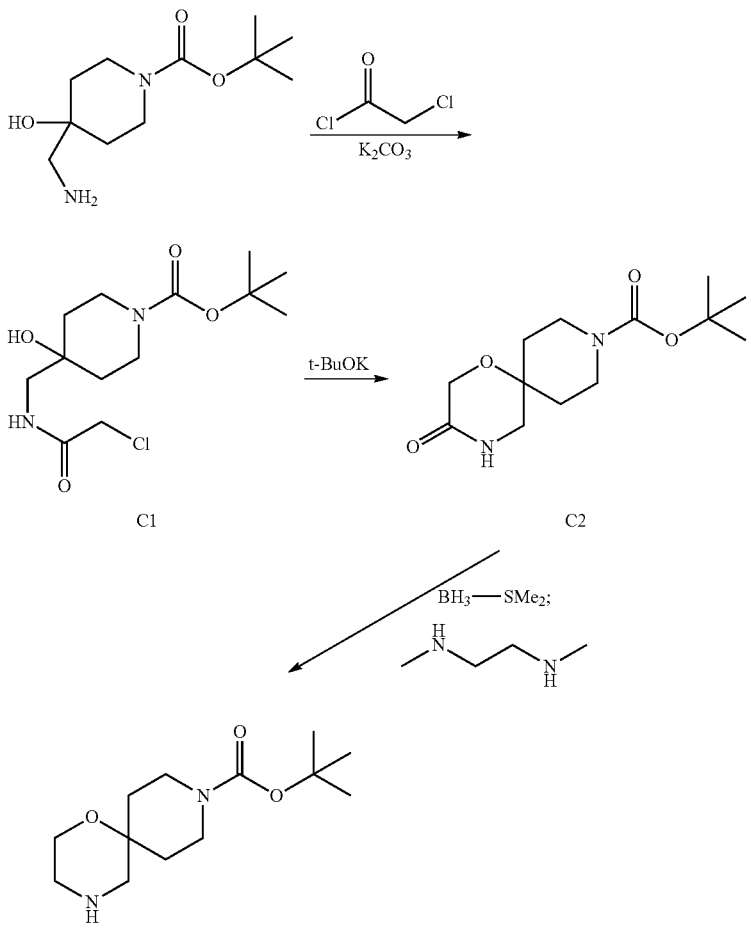

Step 1. Synthesis of tert-butyl 4-{[(chloroacetyl) amino]methyl}-4-hydroxypiperidine-1-carboxylate (C1)

A solution of potassium carbonate (1.32 kg, 9.55 mol) in water (11 L) was added to a solution of tert-butyl 4-(aminomethyl)-4-hydroxypiperidine-1-carboxylate (1.10 kg, 4.78 mol) in ethyl acetate (11 L). The mixture was cooled to 0° C., and then treated in a drop-wise manner with chloroacetyl chloride (595 g, 5.27 mol). After completion of the addition, the reaction mixture was warmed to 25° C. and allowed to stir for 16 hours. The aqueous layer was extracted with ethyl acetate (3×10 L), and the combined organic layers were dried over sodium sulfate, filtered, and concentrated in vacuo; trituration of the residue with tert-butyl methyl ether (10 L) afforded the product (1040 g). The filtrate from the trituration was concentrated and triturated with a mixture of tert-butyl methyl ether and petroleum ether (1:1; 300 mL) to provide additional product (123 g) as a white solid. Combined yield: 1.16 kg, 3.78 mol, 79%. $^1$H NMR (400 MHz, CDCl$_3$) δ 7.02 (br t, J=5 Hz, 1H), 4.09 (s, 2H), 3.88-3.70 (br m, 2H), 3.43-3.28 (br s, 2H), 3.20 (br dd, J=11, 11 Hz, 2H), 2.71 (s, 1H), 1.62-1.46 (m, 4H), 1.45 (s, 9H).

Step 2. Synthesis of tert-butyl 3-oxo-1-oxa-4,9-diazaspiro[5.5]undecane-9-carboxylate (C2)

This reaction was carried out in two similar batches. To a solution of C1 (540 g, 1.76 mol) in 2-propanol (20 L) was added potassium tert-butoxide (1.98 kg, 17.6 mol) at 25° C., and the reaction mixture was stirred at 25° C. for 16 hours. After removal of solvent in vacuo, the residue was partitioned between ethyl acetate (15 L) and water (20 L). The aqueous layer was extracted with ethyl acetate (2×15 L), and the combined organic layers were washed with saturated aqueous sodium chloride solution (15 L), dried over sodium sulfate, filtered, and concentrated under reduced pressure. The residue was triturated with tert-butyl methyl ether (2 L) at 25° C. for 3 hours to afford the product as a white solid. Combined yield from the two batches: 540 g, 2.00 mmol, 57%. $^1$H NMR (400 MHz, CDCl$_3$) δ 6.78-6.59 (br m, 1H), 4.16 (s, 2H), 3.96-3.74 (br s, 2H), 3.24 (d, J=2.6 Hz, 2H), 3.11 (br dd, J=12, 12 Hz, 2H), 1.89 (br d, J=13 Hz, 2H), 1.58-1.48 (m, 2H), 1.46 (s, 9H).

Step 3. Synthesis of tert-butyl 1-oxa-4,9-diazaspiro [5.5]undecane-9-carboxylate (P1)

This reaction was carried out in 12 batches, as follows. Borane-dimethyl sulfide complex (10 M in dimethyl sulfide, 75 mL, 750 mmol) was added in a drop-wise manner to a solution of C2 (50 g, 180 mmol) in tetrahydrofuran (1.5 L). The reaction mixture was heated at reflux (70° C.) for 6 hours and subsequently allowed to stir at 25° C. for 10 hours. It was then quenched with methanol (500 mL), stirred for 30 minutes at 25° C., and concentrated under reduced pressure. The resulting white solid was dissolved in methanol (1 L), treated with N,N'-dimethylethane-1,2-diamine (65 g, 740 mmol), and heated at reflux (70° C.) for 16 hours. The 12 reaction mixtures were combined and concentrated in vacuo to provide a light yellow oil; this was dissolved in dichloromethane (4 L), washed with aqueous ammonium chloride solution (4×2 L), dried over sodium sulfate, filtered, and concentrated under reduced pressure. The residue was triturated with petroleum ether (500 mL) at 25° C. for 30 minutes to provide the product (304 g) as a white solid. The filtrate from the trituration was concentrated in vacuo, and the residue was triturated with petroleum ether (200 mL) at 25° C. for 36 hours, affording additional product (135 g) as a white solid. Combined yield: 439 g, 1.71 mol, 77%. LCMS m/z 257.2 [M+H]$^+$. $^1$H NMR (400 MHz, CDCl$_3$) δ 3.85-3.59 (m, 4H), 3.14 (br dd, J=11, 11 Hz, 2H), 2.84 (dd, J=4.9, 4.6 Hz, 2H), 2.68 (s, 2H), 2.02-1.84 (br m, 2H), 1.47-1.33 (m, 2H), 1.45 (s, 9H).

Preparation P2 tert-Butyl (3R)-3-[(phenylsulfonyl)amino]-1-oxa-8-azaspiro[4.5]decane-8-carboxylate (P2)

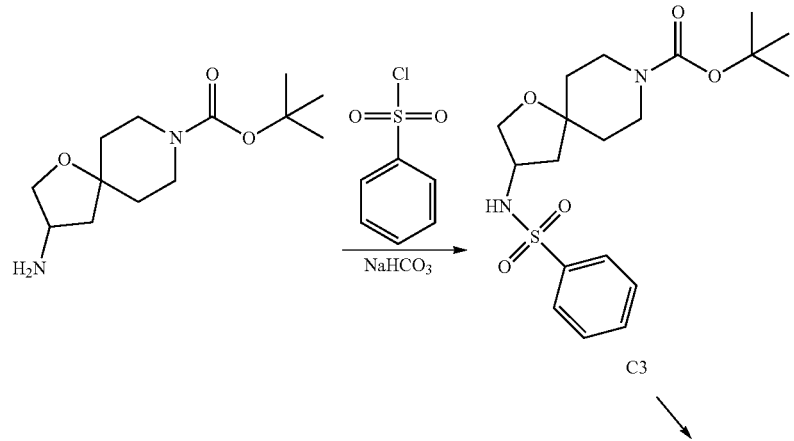

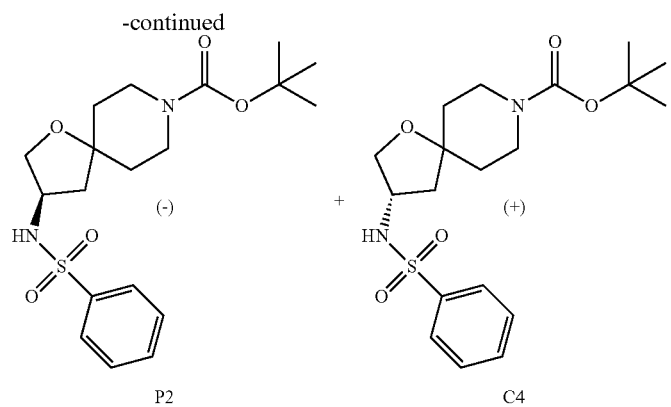

Step 1. Synthesis of tert-butyl 3-[(phenylsulfonyl)amino]-1-oxa-8-azaspiro[4.5]decane-8-carboxylate (C3)

A solution of tert-butyl 3-amino-1-oxa-8-azaspiro[4.5]decane-8-carboxylate (1.98 g, 7.72 mmol) in dichloromethane (80 mL) was treated with saturated aqueous sodium bicarbonate solution (20 mL). Benzenesulfonyl chloride (1.49 mL, 11.7 mmol) was added drop-wise, and the reaction mixture was stirred for 23 hours at room temperature. The aqueous layer was extracted with dichloromethane, and the combined organic layers were washed with saturated aqueous sodium chloride solution, dried over sodium sulfate, filtered, and concentrated in vacuo. This racemic material was purified using silica gel chromatography (Gradient: 20% to 50% ethyl acetate in heptane) to afford the product as a white solid. Yield: 2.88 g, 7.26 mmol, 94%. LCMS m/z 395.4 [M–H$^+$]. $^1$H NMR (400 MHz, CDCl$_3$) δ 7.90-7.86 (m, 2H), 7.64-7.58 (m, 1H), 7.57-7.51 (m, 2H), 5.00 (br d, J=7.8 Hz, 1H), 3.99-3.89 (m, 1H), 3.81 (dd, J=9.6, 5.7 Hz, 1H), 3.58-3.48 (m, 3H), 3.30-3.19 (m, 2H), 1.96 (dd, J=13.4, 7.7 Hz, 1H), 1.66-1.48 (m, 4H), 1.47-1.38 (m, 1H), 1.44 (s, 9H).

Step 2. Isolation of tert-butyl (3R)-3-[(phenylsulfonyl)amino]-1-oxa-8-azaspiro[4.5]decane-8-carboxylate (P2) and tert-butyl (3S)-3-[(phenylsulfonyl)amino]-1-oxa-8-azaspiro[4.5]decane-8-carboxylate (C4)

Compound C3 (from the previous step; 2.88 g, 7.26 mmol) was separated into its component enantiomers via supercritical fluid chromatography [Column: Phenomenex Lux Cellulose-3, 5 µm; Eluent: 7.5% (1:1 methanol/acetonitrile) in carbon dioxide]. The first-eluting product, obtained as a tacky white solid that exhibited a negative (–) rotation, was designated as P2. Yield: 1.35 g, 3.40 mmol, 45%. LCMS m/z 395.5 [M–H$^+$]. $^1$H NMR (400 MHz, CDCl$_3$) δ 7.90-7.86 (m, 2H), 7.64-7.59 (m, 1H), 7.57-7.52 (m, 2H), 4.81 (d, J=7.9 Hz, 1H), 4.00-3.91 (m, 1H), 3.81 (dd, J=9.7, 5.7 Hz, 1H), 3.59-3.48 (m, 3H), 3.30-3.19 (m, 2H), 1.97 (dd, J=13.4, 7.7 Hz, 1H), 1.67-1.49 (m, 4H), 1.48-1.38 (m, 1H), 1.44 (s, 9H).

The second-eluting product, obtained as a tacky white solid that exhibited a positive (+) rotation, was designated as C4. Yield: 1.15 g, 2.90 mmol, 38%. LCMS m/z 395.5 [M–H$^+$]. $^1$H NMR (400 MHz, CDCl$_3$) δ 7.90-7.86 (m, 2H), 7.64-7.59 (m, 1H), 7.57-7.52 (m, 2H), 4.79 (d, J=8.0 Hz, 1H), 4.00-3.91 (m, 1H), 3.81 (dd, J=9.7, 5.7 Hz, 1H), 3.59-3.48 (m, 3H), 3.30-3.19 (m, 2H), 1.97 (dd, J=13.4, 7.7 Hz, 1H), 1.67-1.49 (m, 4H), 1.47-1.38 (m, 1H), 1.44 (s, 9H).

The absolute configurations shown were established as follows: a portion of this batch of P2 was recrystallized from dichloromethane/tert-butyl methyl ether, and its absolute configuration was determined via single crystal X-ray structure determination:

Single-Crystal X-Ray Structural Determination of P2

Data collection was performed on a Bruker APEX diffractometer at room temperature. Data collection consisted of omega and phi scans.

The structure was solved by direct methods using SHELX software suite in the space group P2$_1$2$_1$2$_1$. The structure was subsequently refined by the full-matrix least squares method. All non-hydrogen atoms were found and refined using anisotropic displacement parameters. The hydrogen atom located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correct is 100.0. The Hooft parameter is reported as 0.015 with an esd of 0.09.

The final R-index was 4.2%. A final difference Fourier revealed no missing or misplaced electron density.

Pertinent crystal, data collection and refinement information is summarized in Table 1. Atomic coordinates, bond lengths, bond angles, and displacement parameters are listed in Tables 2-5.

Software and References

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE 1

Crystal data and structure refinement for P2.

| | |
|---|---|
| Empirical formula | $C_{19}H_{28}N_2O_5S$ |
| Formula weight | 396.50 |
| Temperature | 276(2) K |
| Wavelength | 1.54178 Å |
| Crystal system | Orthorhombic |
| Space group | $P2_12_12_1$ |
| Unit cell dimensions | a = 9.79150(10) Å    α = 90° |
| | b = 11.11580(10) Å   β = 90° |
| | c = 18.6694(2) Å     γ = 90° |
| Volume | 2031.98(4) Å³ |
| Z | 4 |
| Density (calculated) | 1.296 Mg/m³ |
| Absorption coefficient | 1.686 mm⁻¹ |
| F(000) | 848 |
| Crystal size | 0.260 × 0.180 × 0.140 mm³ |
| Theta range for data collection | 4.630 to 68.568° |
| Index ranges | −11 <= h <= 11, −13 <= k <= 13, −20 <= l <= 22 |
| Reflections collected | 9404 |
| Independent reflections | 3633 [$R_{int}$ = 0.0247] |
| Completeness to theta = 70.31° | 99.3% |
| Absorption correction | None |
| Refinement method | Full-matrix least-squares on $F^2$ |
| Data/restraints/parameters | 3633/1/251 |
| Goodness-of-fit on $F^2$ | 1.067 |
| Final R indices [I > 2sigma(I)] | R1 = 0.0418, wR2 = 0.1074 |
| R indices (all data) | R1 = 0.0441, wR2 = 0.1098 |
| Absolute structure parameter | 0.017(9) |
| Extinction coefficient | n/a |
| Largest diff. peak and hole | 0.428 and −0.457 e. Å⁻³ |

TABLE 2

Atomic coordinates (×10⁴) and equivalent isotropic displacement parameters (Å² × 10³) for P2.

| | x | y | z | U(eq) |
|---|---|---|---|---|
| S(1) | −3733(1) | 10920(1) | 849(1) | 53(1) |
| N(1) | −3045(3) | 9602(2) | 839(2) | 59(1) |
| N(2) | 3033(2) | 7292(2) | 1366(2) | 52(1) |
| O(1) | −5113(3) | 10761(2) | 1075(1) | 74(1) |
| O(2) | −2848(3) | 11724(2) | 1218(1) | 68(1) |
| O(3) | 29(3) | 8787(2) | 1780(1) | 68(1) |
| O(4) | 5295(2) | 7383(2) | 1100(1) | 53(1) |
| O(5) | 4386(2) | 5806(2) | 1709(1) | 55(1) |
| C(1) | −4868(3) | 11071(3) | −483(2) | 63(1) |
| C(2) | −4920(4) | 11465(4) | −1195(2) | 76(1) |
| C(3) | −3910(5) | 12188(3) | −1452(2) | 77(1) |
| C(4) | −2853(5) | 12532(4) | −1029(2) | 80(1) |
| C(5) | −2775(3) | 12136(3) | −315(2) | 64(1) |
| C(6) | −3796(3) | 11406(2) | −54(2) | 49(1) |
| C(7) | −1575(3) | 9468(3) | 927(2) | 49(1) |
| C(8) | −1069(4) | 9583(4) | 1697(2) | 77(1) |
| C(9) | 248(3) | 8100(3) | 1135(2) | 48(1) |
| C(10) | −1087(3) | 8216(3) | 724(2) | 51(1) |
| C(11) | 601(3) | 6821(3) | 1356(2) | 62(1) |
| C(12) | 1914(4) | 6735(3) | 1772(2) | 67(1) |
| C(13) | 2776(3) | 8526(3) | 1137(2) | 55(1) |
| C(14) | 1463(3) | 8609(3) | 722(2) | 49(1) |
| C(15) | 4329(3) | 6873(2) | 1372(2) | 46(1) |
| C(16) | 5650(3) | 5100(3) | 1749(2) | 50(1) |
| C(17) | 6713(4) | 5783(4) | 2169(2) | 69(1) |
| C(18) | 6126(5) | 4758(4) | 1005(2) | 82(1) |
| C(19) | 5191(4) | 3991(3) | 2158(2) | 62(1) |

U(eq) is defined as one-third of the trace of the orthogonalized $U^{ij}$ tensor.

TABLE 3

Bond lengths [Å] and angles [°] for P2.

| | |
|---|---|
| S(1)—O(2) | 1.423(3) |
| S(1)—O(1) | 1.426(2) |
| S(1)—N(1) | 1.613(2) |
| S(1)—C(6) | 1.772(3) |
| N(1)—C(7) | 1.456(4) |
| N(2)—C(15) | 1.353(4) |
| N(2)—C(13) | 1.459(4) |
| N(2)—C(12) | 1.468(4) |
| O(3)—C(8) | 1.400(4) |
| O(3)—C(9) | 1.441(4) |
| O(4)—C(15) | 1.214(4) |
| O(5)—C(15) | 1.344(3) |
| O(5)—C(16) | 1.467(3) |
| C(1)—C(6) | 1.372(5) |
| C(1)—C(2) | 1.400(5) |
| C(2)—C(3) | 1.362(6) |
| C(3)—C(4) | 1.358(6) |
| C(4)—C(5) | 1.405(5) |
| C(5)—C(6) | 1.376(4) |
| C(7)—C(10) | 1.520(4) |
| C(7)—C(8) | 1.525(5) |
| C(9)—C(11) | 1.520(4) |
| C(9)—C(10) | 1.521(4) |
| C(9)—C(14) | 1.526(4) |
| C(11)—C(12) | 1.506(5) |
| C(13)—C(14) | 1.503(4) |
| C(16)—C(17) | 1.508(5) |
| C(16)—C(18) | 1.514(5) |
| C(16)—C(19) | 1.518(4) |
| O(2)—S(1)—O(1) | 120.73(17) |
| O(2)—S(1)—N(1) | 108.79(15) |
| O(1)—S(1)—N(1) | 106.64(15) |
| O(2)—S(1)—C(6) | 106.86(14) |
| O(1)—S(1)—C(6) | 106.70(15) |
| N(1)—S(1)—C(6) | 106.29(15) |
| C(7)—N(1)—S(1) | 120.3(2) |
| C(15)—N(2)—C(13) | 119.2(2) |
| C(15)—N(2)—C(12) | 123.4(2) |
| C(13)—N(2)—C(12) | 114.8(3) |
| C(8)—O(3)—C(9) | 110.9(2) |
| C(15)—O(5)—C(16) | 122.1(2) |
| C(6)—C(1)—C(2) | 119.8(3) |
| C(3)—C(2)—C(1) | 119.6(4) |
| C(4)—C(3)—C(2) | 120.9(4) |
| C(3)—C(4)—C(5) | 120.4(4) |
| C(6)—C(5)—C(4) | 118.7(3) |
| C(1)—C(6)—C(5) | 120.6(3) |
| C(1)—C(6)—S(1) | 119.9(2) |
| C(5)—C(6)—S(1) | 119.4(3) |
| N(1)—C(7)—C(10) | 112.1(3) |
| N(1)—C(7)—C(8) | 114.8(3) |
| C(10)—C(7)—C(8) | 102.1(3) |
| O(3)—C(8)—C(7) | 107.5(3) |
| O(3)—C(9)—C(11) | 107.7(3) |
| O(3)—C(9)—C(10) | 104.4(2) |
| C(11)—C(9)—C(10) | 114.3(3) |
| O(3)—C(9)—C(14) | 109.9(3) |
| C(11)—C(9)—C(14) | 107.9(2) |
| C(10)—C(9)—C(14) | 112.6(2) |
| C(7)—C(10)—C(9) | 102.8(2) |
| C(12)—C(11)—C(9) | 113.1(3) |
| N(2)—C(12)—C(11) | 110.1(3) |
| N(2)—C(13)—C(14) | 110.9(3) |
| C(13)—C(14)—C(9) | 112.6(2) |
| O(4)—C(15)—O(5) | 125.2(3) |
| O(4)—C(15)—N(2) | 124.5(3) |
| O(5)—C(15)—N(2) | 110.3(2) |
| O(5)—C(16)—C(17) | 109.8(3) |
| O(5)—C(16)—C(18) | 110.3(3) |
| C(17)—C(16)—C(18) | 113.0(3) |
| O(5)—C(16)—C(19) | 102.1(2) |
| C(17)—C(16)—C(19) | 110.6(3) |
| C(18)—C(16)—C(19) | 110.4(3) |

Symmetry transformations used to generate equivalent atoms.

TABLE 4

Anisotropic displacement parameters ($Å^2 \times 10^3$) for P2. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| S(1) | 48(1) | 42(1) | 69(1) | 2(1) | 10(1) | 8(1) |
| N(1) | 44(1) | 42(1) | 91(2) | 9(1) | 4(1) | 3(1) |
| N(2) | 41(1) | 49(1) | 67(2) | 17(1) | 2(1) | 2(1) |
| O(1) | 57(1) | 69(1) | 95(2) | 19(1) | 28(1) | 18(1) |
| O(2) | 80(2) | 52(1) | 70(1) | −7(1) | −6(1) | 9(1) |
| O(3) | 66(2) | 88(2) | 49(1) | −8(1) | −5(1) | 24(1) |
| O(4) | 43(1) | 49(1) | 68(1) | 7(1) | 4(1) | 0(1) |
| O(5) | 46(1) | 46(1) | 73(1) | 16(1) | 1(1) | 4(1) |
| C(1) | 45(2) | 51(2) | 92(2) | 0(2) | −4(2) | −4(1) |
| C(2) | 66(2) | 78(2) | 84(2) | −6(2) | −20(2) | 2(2) |
| C(3) | 85(3) | 77(2) | 69(2) | 6(2) | −1(2) | 2(2) |
| C(4) | 77(2) | 83(3) | 81(2) | 12(2) | 15(2) | −22(2) |
| C(5) | 53(2) | 65(2) | 75(2) | 1(2) | 2(2) | −18(2) |
| C(6) | 40(1) | 36(1) | 70(2) | −2(1) | 5(1) | 4(1) |
| C(7) | 42(1) | 44(1) | 60(2) | 2(1) | 4(1) | 4(1) |
| C(8) | 78(2) | 83(2) | 70(2) | −22(2) | −9(2) | 27(2) |
| C(9) | 47(2) | 49(2) | 48(2) | −1(1) | 3(1) | 6(1) |
| C(10) | 46(1) | 49(1) | 57(2) | −5(1) | 1(1) | 7(1) |
| C(11) | 44(2) | 54(2) | 91(2) | 21(2) | 9(2) | 1(1) |
| C(12) | 50(2) | 69(2) | 83(2) | 35(2) | 10(2) | 9(2) |
| C(13) | 48(2) | 48(2) | 68(2) | 10(1) | −2(1) | 0(1) |
| C(14) | 51(2) | 45(1) | 51(2) | 5(1) | 1(1) | 5(1) |
| C(15) | 44(1) | 43(1) | 50(1) | 2(1) | −1(1) | 2(1) |
| C(16) | 51(2) | 51(2) | 48(2) | 5(1) | 1(1) | 13(1) |
| C(17) | 56(2) | 80(2) | 70(2) | 17(2) | −7(2) | −6(2) |
| C(18) | 120(4) | 71(2) | 56(2) | 4(2) | 14(2) | 37(2) |
| C(19) | 71(2) | 51(2) | 64(2) | 12(1) | −4(2) | 10(2) |

TABLE 5

Hydrogen coordinates ($\times 10^4$) and isotropic displacement parameters ($Å^2 \times 10^3$) for P2.

| | x | y | z | U(eq) |
|---|---|---|---|---|
| H(1X) | −3660(30) | 8980(20) | 932(17) | 57(9) |
| H(1) | −5558 | 10584 | −302 | 75 |
| H(2) | −5639 | 11234 | −1490 | 91 |
| H(3) | −3946 | 12450 | −1925 | 92 |
| H(4) | −2177 | 13033 | −1212 | 96 |
| H(5) | −2047 | 12362 | −25 | 77 |
| H(7) | −1107 | 10063 | 628 | 59 |
| H(8A) | −776 | 10401 | 1791 | 92 |
| H(8B) | −1794 | 9380 | 2029 | 92 |
| H(10A) | −938 | 8151 | 212 | 61 |
| H(10B) | −1738 | 7606 | 872 | 61 |
| H(11A) | −137 | 6501 | 1645 | 75 |
| H(11B) | 674 | 6326 | 929 | 75 |
| H(12A) | 1811 | 7141 | 2229 | 81 |
| H(12B) | 2127 | 5898 | 1865 | 81 |
| H(13A) | 3526 | 8801 | 840 | 66 |
| H(13B) | 2726 | 9045 | 1554 | 66 |
| H(14A) | 1562 | 8173 | 275 | 59 |
| H(14B) | 1285 | 9446 | 607 | 59 |
| H(17A) | 7038 | 6448 | 1888 | 103 |
| H(17B) | 7462 | 5258 | 2281 | 103 |
| H(17C) | 6316 | 6080 | 2605 | 103 |
| H(18A) | 5376 | 4423 | 741 | 124 |
| H(18B) | 6844 | 4173 | 1040 | 124 |
| H(18C) | 6460 | 5461 | 763 | 124 |
| H(19A) | 4803 | 4229 | 2609 | 93 |
| H(19B) | 5962 | 3476 | 2242 | 93 |
| H(19C) | 4519 | 3565 | 1883 | 93 |

Preparation P3 tert-Butyl 3-bromo-1-oxa-8-azaspiro[4.5]decane-8-carboxylate (P3)

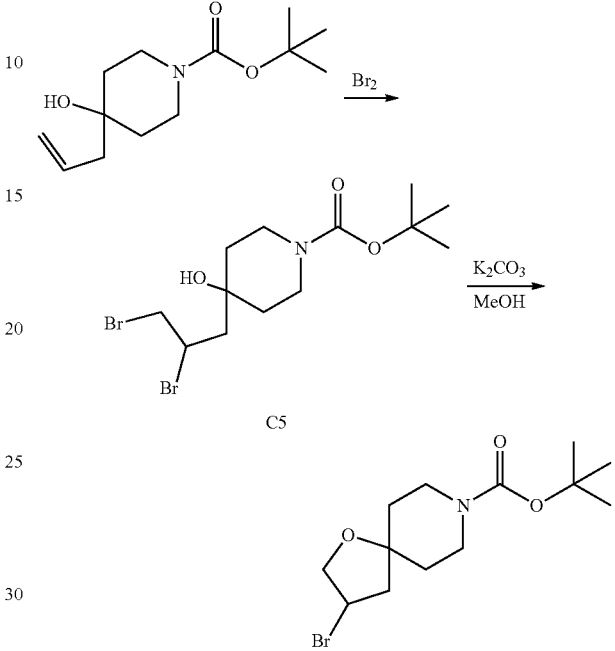

Step 1. Synthesis of tert-butyl 4-(2,3-dibromopropyl)-4-hydroxypiperidine-1-carboxylate (C5)

This reaction was carried out in two identical batches. A solution of tert-butyl 4-hydroxy-4-(prop-2-en-1-yl)piperidine-1-carboxylate (209 g, 0.866 mol) in dichloromethane (1.2 L) was cooled in a cold water bath. A solution of bromine (152 g, 0.951 mol) in dichloromethane (250 mL) was added at such a rate that the color of the reaction mixture did not become intense. At the conclusion of the addition, an aqueous solution containing sodium thiosulfate and sodium bicarbonate was added to the reaction mixture, and stirring was continued until the mixture had completely decolorized. At this point, the two batches were combined. The aqueous layer was extracted with dichloromethane (3×400 mL), and the combined organic layers were washed with saturated aqueous sodium chloride solution (2×200 mL), dried over sodium sulfate, filtered, and concentrated in vacuo to afford the product as a red gum. Yield: 600 g, 1.5 mol, 87%. $^1$H NMR (400 MHz, CDCl$_3$) δ 4.43-4.33 (m, 1H), 3.96-3.74 (m, 2H), 3.91 (dd, J=10.3, 4.0 Hz, 1H), 3.66 (dd, J=10.0, 9.8 Hz, 1H), 3.27-3.13 (m, 2H), 2.47 (dd, half of ABX pattern, J=15.8, 2.8 Hz, 1H), 2.13 (dd, half of ABX pattern, J=15.7, 8.9 Hz, 1H), 1.78-1.68 (m, 2H), 1.65-1.53 (m, 2H, assumed; partially obscured by water peak), 1.47 (s, 9H).

Step 2. Synthesis of tert-butyl 3-bromo-1-oxa-8-azaspiro[4.5]decane-8-carboxylate (P3)

Potassium carbonate (119 g, 861 mmol) was added to a cooled solution of C5 (230 g, 573 mmol) in methanol (1.5

L), and the reaction mixture was stirred at 10° C. to 15° C. for 16 hours. The crude reaction mixture was combined with the crude reaction mixtures from two similar reactions using C5 (350 g, 873 mmol; and 20 g, 50 mmol) and filtered. The filtrate was concentrated in vacuo, and the resulting red oil was recrystallized from petroleum ether (150 mL) at 0° C. to provide a light yellow solid (360 g). This was subjected to silica gel chromatography (Eluent: dichloromethane), and the purified material was recrystallized from petroleum ether (120 mL) and washed with petroleum ether (3×40 mL) to afford the product as a white solid (180 g). The mother liquors from recrystallization were concentrated under reduced pressure and purified using silica gel chromatography (Gradient: 0% to 20% ethyl acetate in petroleum ether). The resulting material was recrystallized from petroleum ether (100 mL) and washed with petroleum ether (3×40 mL), affording additional product as a white solid (95 g). Combined yield: 275 g, 0.859 mol, 57%. $^1$H NMR (400 MHz, DMSO-$d_6$) δ 4.71-4.63 (m, 1H), 4.12 (dd, J=10.4, 4.9 Hz, 1H), 3.90 (dd, J=10.5, 3.8 Hz, 1H), 3.52-3.40 (m, 2H), 3.3-3.15 (m, 2H), 2.41 (dd, J=14.3, 7.3 Hz, 1H), 2.10 (dd, J=14.0, 4.0 Hz, 1H), 1.79-1.71 (m, 1H), 1.65 (br ddd, half of ABXY pattern, J=13, 10, 4 Hz, 1H), 1.55-1.41 (m, 2H), 1.39 (s, 9H).

Preparation P4 tert-Butyl (3R)-3-amino-1-oxa-8-azaspiro[4.5]decane-8-carboxylate, (2R)-5-oxopyrrolidine-2-carboxylate salt (P4)

Step 1. Synthesis of tert-butyl (3R)-3-amino-1-oxa-8-azaspiro[4.5]decane-8-carboxylate (C6)

A pH 8.0 buffer solution was prepared, containing 0.1 M aqueous potassium phosphate and 2 mM magnesium chloride. A stock solution of substrate was prepared as follows: tert-butyl 3-oxo-1-oxa-8-azaspiro[4.5]decane-8-carboxylate (18.0 g, 70.5 mmol) was dissolved in water containing 4% dimethyl sulfoxide (14.4 mL). Warming and stirring were required for dissolution, and the resulting solution was maintained at 40° C.

Propan-2-amine, hydrochloride salt (16.8 g, 176 mmol) was added to a mixture of pyridoxal 5'-phosphate monohydrate (1.87 g, 7.05 mmol) and the pH 8.0 buffer (300 mL). The resulting pH was approximately 6.5; the pH was adjusted to 8 via addition of aqueous potassium hydroxide solution (6 M; approximately 4 mL). The stock solution of substrate was added via syringe, in 5 mL portions, resulting in a suspension, still at pH 8. Codex® ATA-200 transaminase (1.4 g) was almost completely dissolved in pH 8 buffer (20 mL), and poured into the reaction mixture. Additional pH 8 buffer (25.6 mL) was used to ensure complete transfer of the enzyme. The reaction mixture was stirred at 35° C. with a nitrogen sweep (32 mL/minute) through a needle placed approximately 0.5 cm above the reaction surface. Due to difficulties in stirring, vacuum (220 Torr, 300 mbar) was applied after 3 hours, to remove the acetone generated by the transamination reaction. The suspended solids were broken up manually, which improved the stirring of the reaction mixture. After 26 hours, the reaction mixture was

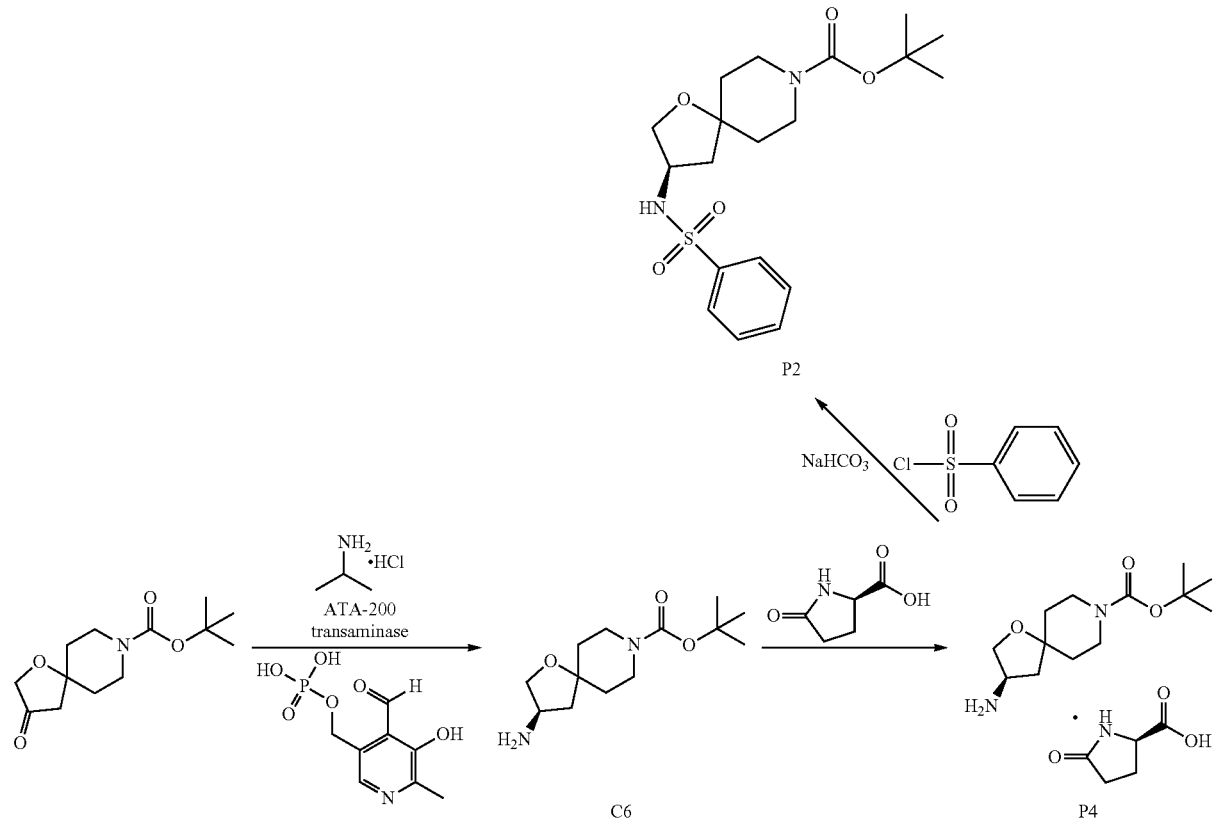

allowed to cool to room temperature, and aqueous hydrochloric acid (6 M, 5 mL) was added, to bring the pH from 8 to 6.5. After addition of ethyl acetate (200 mL), the mixture was vigorously stirred for 5 minutes and then filtered through diatomaceous earth (43 g; this filter aid had been slurried in water prior to being introduced into the filter funnel. The water was then removed, providing a tightly packed bed). The filter pad was washed sequentially with water (120 mL) and ethyl acetate (100 mL), and the aqueous layer of the combined filtrates was adjusted to pH 9-9.5 with aqueous potassium hydroxide solution (6 M; approximately 10 mL). The aqueous layer was then treated with dichloromethane (200 mL), and the resulting mixture was vigorously stirred for 5 minutes before being filtered through a pad of diatomaceous earth. The filter pad was washed with dichloromethane (100 mL), and the aqueous layer of the combined filtrates was extracted twice with dichloromethane, in the same manner as that described above, with adjustment of the pH to 9-10 (this required approximately 2 mL of the 6 M aqueous potassium hydroxide solution in both cases). All of the dichloromethane extracts were combined and dried over sodium sulfate with vigorous stirring. Filtration and concentration in vacuo afforded the product as an oily yellow solid (14.76 g). A fourth extraction was carried out in the same manner, but in this case the aqueous layer was adjusted to a pH of >10. The product obtained from this extraction was a white solid (1.9 g). Combined yield: 16.61 g, 64.79 mmol, 92%. $^1$H NMR (500 MHz, CDCl$_3$) δ 3.95 (dd, J=9.0, 5.6 Hz, 1H), 3.69-3.63 (m, 1H), 3.62-3.52 (m, 3H), 3.38-3.27 (m, 2H), 2.6-2.2 (v br s, 2H), 2.07 (dd, J=13.0, 7.6 Hz, 1H), 1.78-1.71 (m, 1H), 1.69-1.56 (m, 2H), 1.55-1.47 (m, 2H), 1.45 (s, 9H).

Step 2. Synthesis of tert-butyl (3R)-3-amino-1-oxa-8-azaspiro[4.5]decane-8-carboxylate, (2R)-5-oxopyrrolidine-2-carboxylate salt (P4)

A solution of C6 (16.61 g, 64.79 mmol) in ethanol (400 mL) was heated to 63° C. and treated portion-wise with (2R)-5-oxopyrrolidine-2-carboxylic acid (7.78 g, 60.3 mmol). The reaction mixture was then removed from the heating bath, and allowed to cool overnight. The mixture was cooled to 12° C. in an ice bath, and filtered. The collected solids were washed with cold ethanol (2×50 mL) and then with diethyl ether (100 mL), affording the product as a pale yellow solid (19.2 g). The combined filtrates were concentrated in vacuo, with removal of approximately 400 mL of solvents. A thin line of solid formed around the inner surface of the flask. This was swirled back into the remaining solvents; diethyl ether (100 mL) was added, and the mixture was cooled in an ice bath with stirring. After approximately 15 minutes, the mixture was filtered and the collected solids were washed with diethyl ether (100 mL), affording additional product as a yellow solid (1.5 g). Combined yield: 20.7 g, 53.7 mmol, 89%. $^1$H NMR (500 MHz, D$_2$O) δ 4.16 (dd, J=8.9, 5.9 Hz, 1H), 4.11 (dd, half of ABX pattern, J=10.4, 5.8 Hz, 1H), 4.09-4.03 (m, 1H), 3.93 (dd, J=10.3, 3.1 Hz, 1H), 3.61-3.46 (m, 2H), 3.46-3.30 (m, 2H), 2.53-2.36 (m, 4H), 2.06-1.97 (m, 1H), 1.85 (dd, J=14.1, 4.6 Hz, 1H), 1.82-1.72 (m, 2H), 1.72-1.65 (m, 1H), 1.59 (ddd, half of ABXY pattern, J=18, 9, 4.5 Hz, 1H), 1.43 (s, 9H).

Conversion of P4 to P2, for Confirmation of Absolute Stereochemistry.

A small sample of P4 was derivatized via reaction with benzenesulfonyl chloride and saturated aqueous sodium bicarbonate solution for 1 hour at 40° C. The reaction mixture was extracted with ethyl acetate, and the solvent was removed from the extract under a stream of nitrogen. Supercritical fluid chromatographic analysis (Column: Chiral Technologies Chiralcel OJ-H, 5 µm; Mobile phase A: carbon dioxide; Mobile phase B: methanol; Gradient: 5% to 60% B) revealed the product to have an enantiomeric excess of >99%. Injection, under the same conditions, of samples of P2 and C4 (See Preparation P2) established the derivatization product as identical to P2, the absolute configuration of which was determined via X-ray crystallographic analysis (see above).

Improved synthesis of tert-butyl (3R)-3-amino-1-oxa-8-azaspiro[4.5]decane-8-carboxylate (C6)

A pH 8.0 buffer solution was prepared, containing 0.1 M aqueous potassium phosphate. A stock solution of substrate was prepared as follows: tert-butyl 3-oxo-1-oxa-8-azaspiro[4.5]decane-8-carboxylate (4.00 g, 15.7 mmol) was dissolved in dimethyl sulfoxide (4 mL); some warming was required to effect dissolution.

An aqueous solution of propan-2-amine, hydrochloride salt (4.0 M; 9.80 mL, 39.2 mmol) was combined with the potassium phosphate buffer (63.8 mL). The substrate solution was then added slowly, over 2 minutes. After this mixture had stirred overnight, Codex® ATA-200 transaminase (batch D11099; 320 mg) and pyridoxal 5'-phosphate monohydrate (40 mg, 0.16 mmol) were added, and the reaction mixture was stirred for 24 hours at 35° C. with a nitrogen sweep (50 mL/minute) through a needle placed above the reaction surface. The pH was then adjusted to 3.2 by addition of aqueous hydrochloric acid (12 M, approximately 500 µL), and the resulting mixture was treated with diatomaceous earth (2.6 g) and ethyl acetate (50 mL), and stirred for 30 minutes. The mixture was filtered through a pad of diatomaceous earth (previously wetted with 1.3 g water), and the aqueous layer of the filtrate was adjusted to pH 10.2 by addition of aqueous sodium hydroxide solution (25%; approximately 3.5 mL). This was repeatedly extracted with tert-butyl methyl ether (50 mL), with the aqueous layer being readjusted to pH 10.2 between extractions. After 4 extractions, the organic layers were combined, dried over sodium sulfate, and filtered. {Solutions of this type, either in tert-butyl methyl ether or 2-methyltetrahydrofuran, were normally utilized directly in subsequent reactions; the concentration of C6 was determined via solvent removal from a specific volume of solution and determination of the mass of the residue.} Concentration in vacuo afforded the product as a white solid. Yield: 1.85 g, 7.22 mmol, 46%. $^1$H NMR (400 MHz, CDCl$_3$) δ 3.94 (dd, J=8.8, 5.7 Hz, 1H), 3.67-3.51 (m, 3H), 3.49 (dd, J=8.8, 5.3 Hz, 1H), 3.39-3.26 (m, 2H), 2.06 (dd, J=12.9, 7.4 Hz, 1H), 1.77-1.42 (m, 5H), 1.45 (s, 9H).

Preparation P5

1,1,1,3,3,3-Hexafluoropropan-2-yl 3-(methylamino)-1-oxa-8-azaspiro[4.5]decane-8-carboxylate (P5)

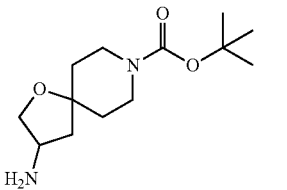
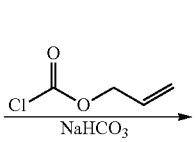
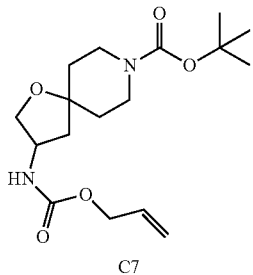
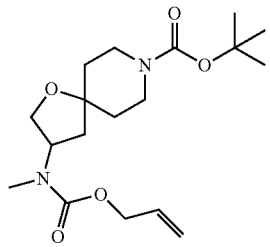

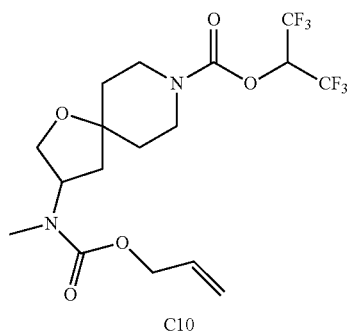

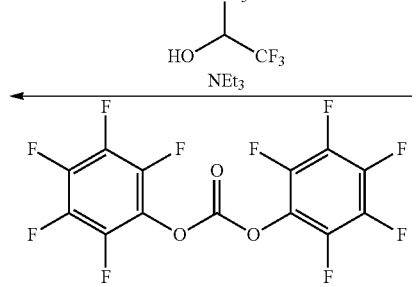

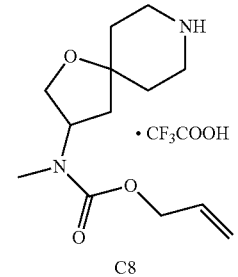

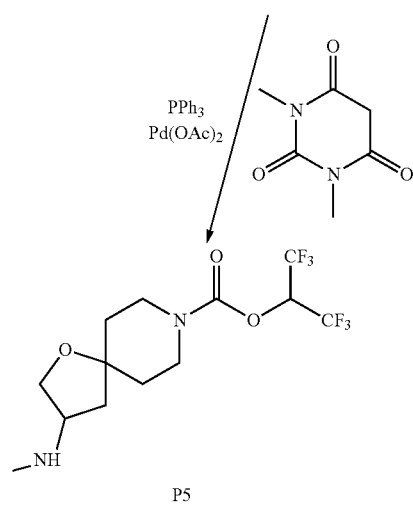

Step 1. Synthesis of tert-butyl 3-{[(prop-2-en-1-yloxy)carbonyl]amino}-1-oxa-8-azaspiro[4.5]decane-8-carboxylate (C7)

Prop-2-en-1-yl carbonochloridate (8.06 g, 66.9 mmol) was added drop-wise to a 0° C. solution of tert-butyl 3-amino-1-oxa-8-azaspiro[4.5]decane-8-carboxylate (15.3 g, 59.7 mmol) in a mixture of tetrahydrofuran (240 mL) and aqueous sodium bicarbonate solution (80 mL), and the reaction mixture was allowed to slowly warm to room temperature over 2.5 hours. The reaction mixture was combined with a similar reaction carried out using tert-butyl 3-amino-1-oxa-8-azaspiro[4.5]decane-8-carboxylate (1.0 g, 3.9 mmol), and the mixture was concentrated under reduced pressure to remove tetrahydrofuran. The aqueous residue was extracted with ethyl acetate (250 mL), and the organic layer was washed sequentially with water (2×150 mL) and saturated aqueous sodium chloride solution (100 mL), dried over sodium sulfate, filtered, and concentrated in vacuo. Silica gel chromatography (Gradient: 0% to 20% ethyl acetate in petroleum ether) afforded the product as a white solid. Combined yield: 14.0 g, 41.1 mmol, 65%. $^1$H NMR (400 MHz, CDCl$_3$) δ 5.98-5.86 (m, 1H), 5.35-5.27 (m, 1H), 5.26-5.20 (m, 1H), 4.94-4.84 (br m, 1H), 4.56 (br d, J=5.5 Hz, 2H), 4.38-4.27 (br m, 1H), 4.00 (dd, J=9.5, 5.5 Hz, 1H), 3.67 (br dd, J=9.8, 4.3 Hz, 1H), 3.66-3.54 (br m, 2H), 3.37-3.25 (m, 2H), 2.14 (dd, J=13.0, 7.5 Hz, 1H), 1.73-1.57 (m, 4H, assumed; partially obscured by water peak), 1.56-1.47 (m, 1H), 1.46 (s, 9H).

Step 2. Synthesis of tert-butyl 3-{methyl[(prop-2-en-1-yloxy)carbonyl]amino}-1-oxa-8-azaspiro[4.5]decane-8-carboxylate (C8)

Sodium hydride (60% dispersion in mineral oil; 2.11 g, 52.8 mmol) was added to a 0° C. solution of C7 (9.0 g, 26 mmol) in N,N-dimethylformamide (250 mL). The mixture was stirred at 0° C. for 30 minutes, whereupon iodomethane (9.38 g, 66.1 mmol) was added in a drop-wise manner, and the reaction mixture was allowed to warm from 0° C. to room temperature over 1.5 hours. It was then combined with a similar reaction mixture derived from C7 (100 mg, 0.29 mmol), poured into ice water (400 mL), and extracted with ethyl acetate (3×200 mL). The combined organic layers were washed sequentially with water (3×150 mL) and with saturated aqueous sodium chloride solution (200 mL), dried over sodium sulfate, and filtered. The filtrate was concentrated in vacuo and the residue was purified using silica gel chromatography (Eluent: 4:1 petroleum ether/ethyl acetate), affording the product as a pale brown oil. Combined yield: 9.0 g, 25 mmol, 95%. $^1$H NMR (400 MHz, CDCl$_3$) δ 6.00-5.89 (m, 1H), 5.34-5.27 (m, 1H), 5.25-5.20 (m, 1H), 5.10-4.86 (br m, 1H), 4.60 (ddd, J=5.5, 1.5, 1.0 Hz, 2H), 3.94 (dd, half of ABX pattern, J=9.5, 7.5 Hz, 1H), 3.76 (dd, half of ABX pattern, J=9.8, 5.3 Hz, 1H), 3.68-3.53 (br m, 2H), 3.38-3.23 (m, 2H), 2.88 (s, 3H), 2.09 (dd, J=13.0, 9.0 Hz, 1H), 1.75-1.61 (m, 4H), 1.52-1.42 (m, 1H), 1.46 (s, 9H).

Step 3. Synthesis of prop-2-en-1-yl methyl(1-oxa-8-azaspiro[4.5]dec-3-yl)carbamate, trifluoroacetate salt (C9)

Trifluoroacetic acid (20 mL) was added to a 0° C. solution of C8 (6.0 g, 17 mmol) in dichloromethane (60 mL), and the reaction mixture was stirred at room temperature for 18 hours. Removal of solvent in vacuo afforded the product (6.2 g) as a pale brown gum, a portion of which was used directly in the next step. LCMS m/z 255.2 [M+H]$^+$.

Step 4. Synthesis of 1,1,1,3,3,3-hexafluoropropan-2-yl 3-{methyl[(prop-2-en-1-yloxy)carbonyl]amino}-1-oxa-8-azaspiro[4.5]decane-8-carboxylate (C10)

Bis(pentafluorophenyl) carbonate (6.10 g, 15.5 mmol) was added to a 0° C. solution of 1,1,1,3,3,3-hexafluoropropan-2-ol (2.60 g, 15.5 mmol) in acetonitrile (60 mL). Triethylamine (7.83 g, 77.4 mmol) was added, and the reaction mixture was stirred at 0° C. for 30 minutes, then at 28° C. for 2 hours, providing Solution A.

Meanwhile, triethylamine (2.5 g, 25 mmol) was slowly added to a 0° C. solution of C9 (from the previous step; 3.1 g, mmol) in acetonitrile (30 mL). After this reaction mixture had been stirred for 30 minutes at 0° C., Solution A was added, and the reaction mixture was allowed to stir at 26° C. for 18 hours. It was then concentrated in vacuo and purified via chromatography on silica gel (Gradient: 0% to 10% ethyl acetate in petroleum ether) to afford the product as a pale yellow oil. From analysis of the $^1$H NMR, this material was presumed to exist as a mixture of rotamers. Yield: 3.5 g, 7.8 mmol, 92% over two steps. $^1$H NMR (400 MHz, CDCl$_3$) δ 6.01-5.89 (m, 1H), 5.76 (septet, J=6.2 Hz, 1H), 5.35-5.27 (m, 1H), 5.26-5.20 (m, 1H), 5.08-4.90 (br m, 1H), 4.64-4.58 (m, 2H), 4.01-3.77 (m, 3H), 3.78 (dd, J=10.0, 5.5 Hz, 1H), 3.48-3.27 (m, 2H), [2.89 (s) and 2.88 (s), total 3H], [2.17-2.08 (m) and 2.10 (dd, J=13.6, 9.0 Hz), total 1H], 1.88-1.67 (m, 4H), 1.57-1.44 (m, 1H).

Step 5. Synthesis of 1,1,1,3,3,3-hexafluoropropan-2-yl 3-(methylamino)-1-oxa-8-azaspiro[4.5]decane-8-carboxylate (P5)

To a solution of C10 (3.30 g, 7.36 mmol), 1,3-dimethylpyrimidine-2,4,6(1H,3H,5H)-trione (2.30 g, 14.7 mmol), and triphenylphosphine (579 mg, 2.21 mmol) in dichloromethane (60 mL) was added palladium(II) acetate (165 mg, 0.735 mmol). The reaction mixture was stirred at room temperature for 18 hours, whereupon it was concentrated in vacuo. Purification via silica gel chromatography (Gradient: 0% to 100% ethyl acetate in petroleum, followed by a second chromatographic purification using 0% to 10% methanol in dichloromethane) provided the product as a brown gum. Yield: 2.4 g, 6.6 mmol, 90%. LCMS m/z 365.2 [M+H]$^+$. $^1$H NMR (400 MHz, CDCl$_3$), characteristic peaks: δ 5.75 (septet, J=6.1 Hz, 1H), 4.04-3.91 (m, 1H), 3.90-3.71 (br m, 3H), 2.47 (br s, 3H), 2.15-2.02 (m, 1H), 1.91-1.47 (m, 5H, assumed; partially obscured by water peak).

Preparation P6

1-({[3-(Methylamino)-1-oxa-8-azaspiro[4.5]dec-8-yl]carbonyl}oxy)pyrrolidine-2,5-dione (P6)

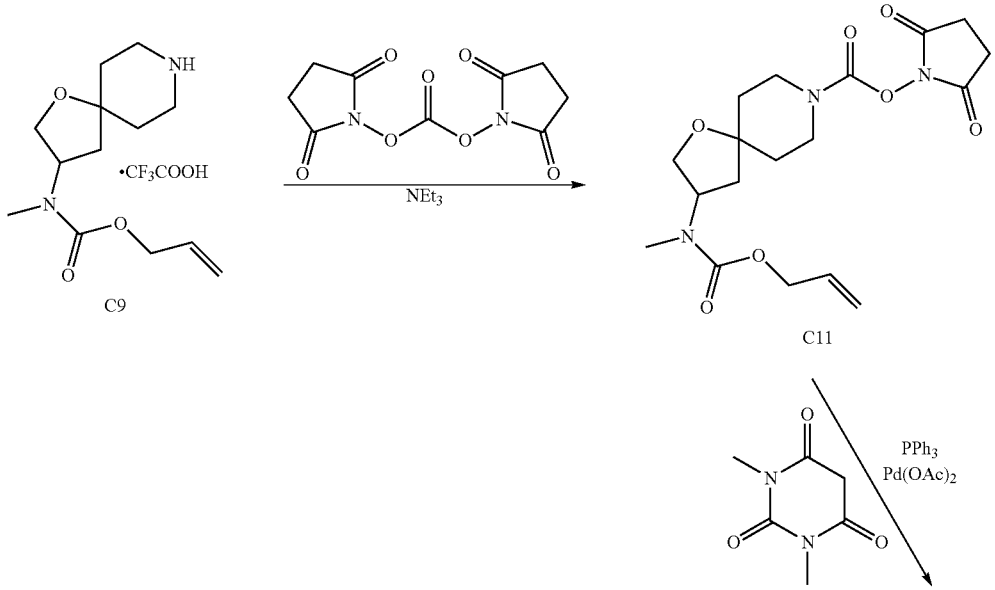

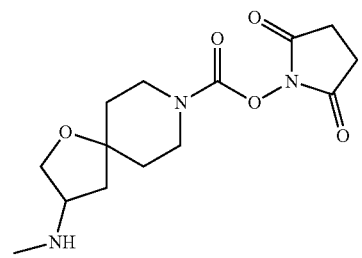

P6

Step 1. Synthesis of prop-2-en-1-yl (8-{[(2,5-di-oxopyrrolidin-1-yl)oxy]carbonyl}-1-oxa-8-azaspiro[4.5]dec-3-yl)methylcarbamate (C11)

To a 0° C. solution of C9 (from step 3 of Preparation P5; 3.1 g, mmol) and triethylamine (2.55 g, 25.2 mmol) in acetonitrile (60 mL) was added N,N'-disuccinimidyl carbonate (3.23 g, 12.6 mmol). The reaction mixture was allowed to warm from 0° C. to room temperature over 18 hours, whereupon it was concentrated in vacuo and purified via chromatography on silica gel (Gradient: 17% to 50% ethyl acetate in petroleum ether). The resulting material was dissolved in ethyl acetate (80 mL), washed sequentially with hydrochloric acid (0.5 M; 4×30 mL), water (30 mL), aqueous sodium bicarbonate solution (2×30 mL), and saturated aqueous sodium chloride solution (30 mL), then dried over sodium sulfate and filtered. The filtrate was concentrated under reduced pressure, affording the product as a white solid. Yield: 3.0 g, 7.6 mmol, 89% over two steps. LCMS m/z 396.1 [M+H]$^+$. $^1$H NMR (400 MHz, CDCl$_3$) δ 6.01-5.89 (m, 1H), 5.35-5.27 (m, 1H), 5.26-5.20 (m, 1H), 5.08-4.88 (br m, 1H), 4.63-4.58 (m, 2H), 3.99-3.74 (m, 4H), 3.55-3.25 (m, 2H), 2.88 (s, 3H), 2.83 (s, 4H), 2.10 (dd, J=13.0, 9.0 Hz, 1H), 1.94-1.59 (m, 4H), 1.72 (dd, J=13.0, 7.0 Hz, 1H).

Step 2. Synthesis of 1-({[3-(methylamino)-1-oxa-8-azaspiro[4.5]dec-8-yl]carbonyl}oxy)pyrrolidine-2,5-dione (P6)

To a solution of C11 (2.8 g, 7.1 mmol), 1,3-dimethylpyrimidine-2,4,6(1H,3H,5H)-trione (2.21 g, 14.2 mmol), and triphenylphosphine (557 mg, 2.12 mmol) in dichloromethane (60 mL) was added palladium(II) acetate (159 mg, 0.708 mmol). The reaction mixture was stirred at room temperature for 18 hours, whereupon it was concentrated in vacuo and purified using chromatography on silica gel (Gradient: 0% to 100% ethyl acetate in petroleum, followed by a second chromatographic purification using 0% to 10% methanol in dichloromethane) to afford the product as an orange solid. By LCMS and $^1$H NMR analysis, this material contained impurities. Yield: 2.0 g, 6.4 mmol, 90%. LCMS m/z 312.2 [M+H]$^+$. $^1$H NMR (400 MHz, CDCl$_3$), characteristic peaks: δ 3.98 (dd, J=9.5, 6.0 Hz, 1H), 2.82 (s, 4H), 2.46 (s, 3H), 2.08 (dd, J=13.0, 7.5 Hz, 1H), 1.89-1.56 (m, 5H, assumed; partially obscured by water peak).

Example 1

1,1,1,3,3,3-Hexafluoropropan-2-yl 4-(phenylsulfonyl)-1-oxa-4,9-diazaspiro[5.5]undecane-9-carboxylate (1)

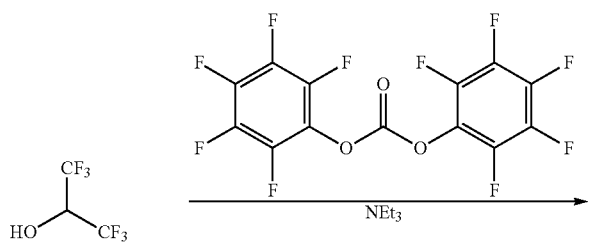
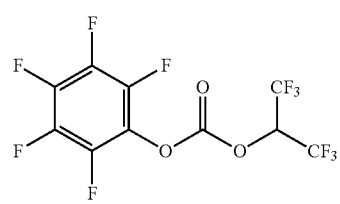

C12

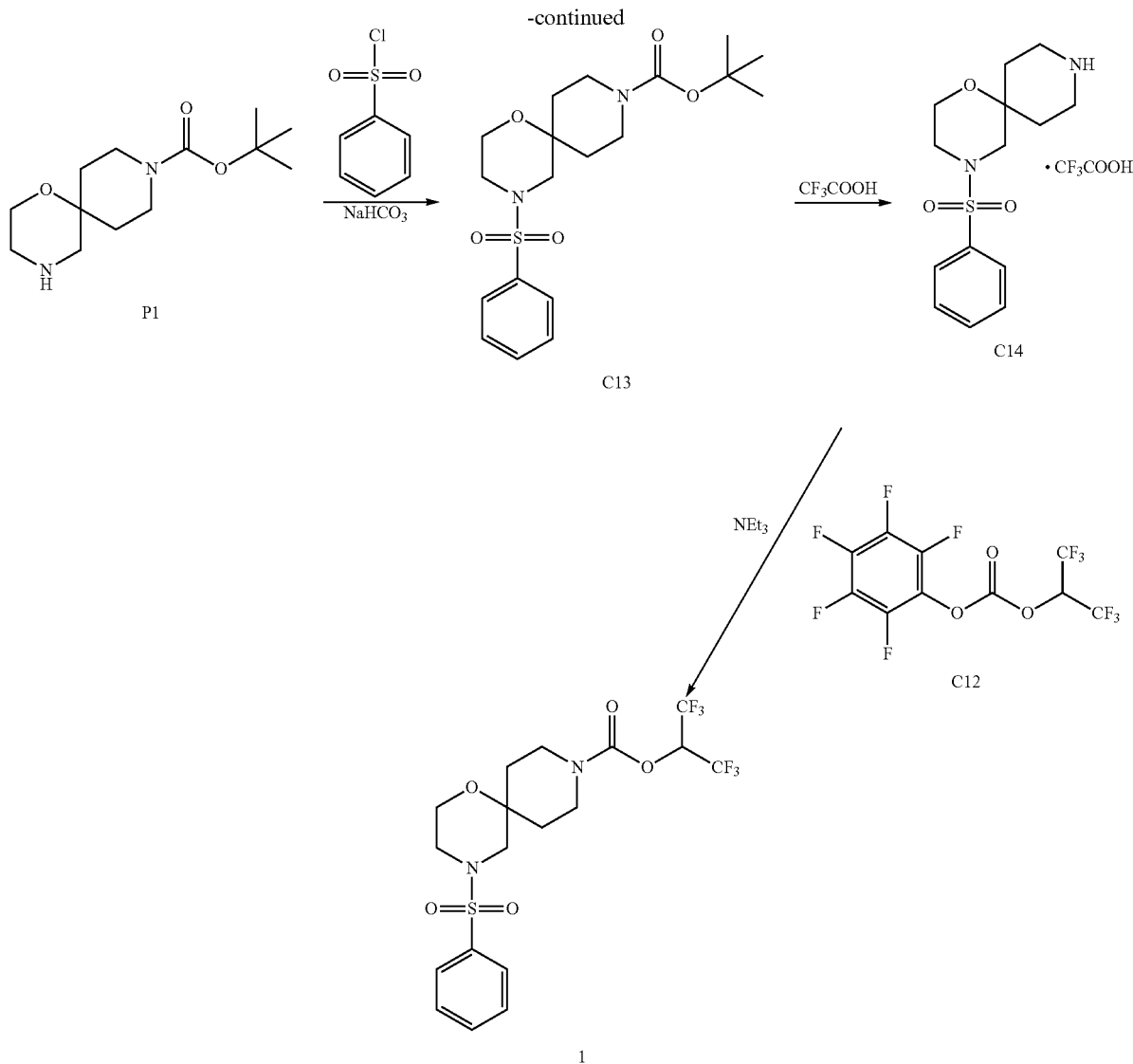

Step 1. Synthesis of 1,1,1,3,3,3-hexafluoropropan-2-yl pentafluorophenyl carbonate (C12)

Bis(pentafluorophenyl) carbonate (112 mg, 0.284 mmol) was added to a 15° C. solution of 1,1,1,3,3,3-hexafluoropropan-2-ol (47.9 mg, 0.285 mmol) in acetonitrile (2 mL), and the mixture was cooled to 0° C. Triethylamine (144 mg, 1.42 mmol) was added at 0° C., and the reaction mixture was stirred at 0° C. for 30 minutes, then stirred at 15° C. for 2 hours. The resulting solution of C12 was used directly in Step 4. For subsequent syntheses described herein that utilize C12, this material was generated at the appropriate scale, and the reaction solution of C12 was used directly in the coupling reaction

Step 2. Synthesis of tert-butyl 4-(phenylsulfonyl)-1-oxa-4,9-diazaspiro[5.5]undecane-9-carboxylate (C13)

Saturated aqueous sodium bicarbonate solution (1.5 mL) and benzenesulfonyl chloride (44.8 mg, 0.254 mmol) were added portion-wise to a solution of P1 (50 mg, 0.20 mmol) in dichloromethane (3 mL). After the reaction mixture had been stirred at 15° C. for 16 hours, it was extracted with dichloromethane (2×3 mL), and the combined organic layers were dried over sodium sulfate, filtered, and concentrated in vacuo. The residue was purified via preparative thin-layer chromatography on silica gel (Eluent: 1:1 petroleum ether/ethyl acetate) to afford the product as a colorless gum. Yield: 76 mg, 0.19 mmol, 95%. LCMS m/z 419.1 [M+Na$^+$]. $^1$H NMR (400 MHz, CDCl$_3$) δ 7.75 (br d, J=7 Hz, 2H), 7.64 (br dd, half of ABX pattern, J=7.5, 7.0 Hz, 1H), 7.57 (br dd, half of ABX pattern, J=7.5, 7.5 Hz, 2H), 3.81-3.65 (br m, 2H), 3.79 (dd, J=5.0, 5.0 Hz, 2H), 3.19-3.08 (m, 2H), 3.10-2.64 (br m, 4H), 1.98-1.79 (br m, 2H), 1.54-1.45 (m, 2H), 1.46 (s, 9H).

Step 3. Synthesis of 4-(phenylsulfonyl)-1-oxa-4,9-diazaspiro[5.5]undecane, trifluoroacetic acid salt (C14)

Trifluoroacetic acid (1 mL) was added to a solution of C13 (74 mg, 0.19 mmol) in dichloromethane (4 mL) and the reaction mixture was stirred at 15° C. for 2 hours. Removal of solvents in vacuo provided the product as a colorless oil, which was taken directly to the following step. LCMS m/z 296.8 [M+H]$^+$.

Step 4. Synthesis of 1,1,1,3,3,3-hexafluoropropan-2-yl 4-(phenylsulfonyl)-1-oxa-4,9-diazaspiro[5.5]undecane-9-carboxylate (1)

To a 0° C. solution of C14 (from the previous step; 0.19 mmol, trifluoroacetic acid salt) in acetonitrile (3 mL) was added triethylamine (96.1 mg, 0.950 mmol), and the mixture was stirred at 0° C. for a few minutes. Compound C12 [from step 1, as the crude reaction mixture in acetonitrile (2 mL); 0.284 mmol] was added drop-wise to the cold solution, and the reaction mixture was stirred at 0° C. for a few minutes, then stirred at 15° C. for 2 days. The reaction mixture was concentrated in vacuo, and purified via reversed-phase HPLC (Column: Agela Durashell, 5 μm; Mobile phase A: 0.225% formic acid in water; Mobile phase B: acetonitrile; Gradient: 58% to 78% B), affording the product as a white solid. Yield: 16.8 mg, 34.3 μmol, 18% over 2 steps. LCMS m/z 491.0 [M+H]$^+$. $^1$H NMR (400 MHz, CDCl$_3$) δ 7.77-7.72 (m, 2H), 7.68-7.62 (m, 1H), 7.61-7.54 (m, 2H), 5.76 (septet, J=6.2 Hz, 1H), 3.94-3.83 (m, 2H), 3.79 (dd, J=5.0, 5.0 Hz, 2H), 3.33-3.18 (m, 2H), 3.07-2.95 (m, 2H), 2.80 (AB quartet, J$_{AB}$=11.5 Hz, Δv$_{AB}$=15.2 Hz, 2H), 2.06-1.95 (m, 2H), 1.59-1.45 (m, 2H).

Example 2

1,1,1,3,3,3-Hexafluoropropan-2-yl 4-[(4-fluorophenyl)sulfonyl]-1-oxa-4,9-diazaspiro[5.5]undecane-9-carboxylate (2)

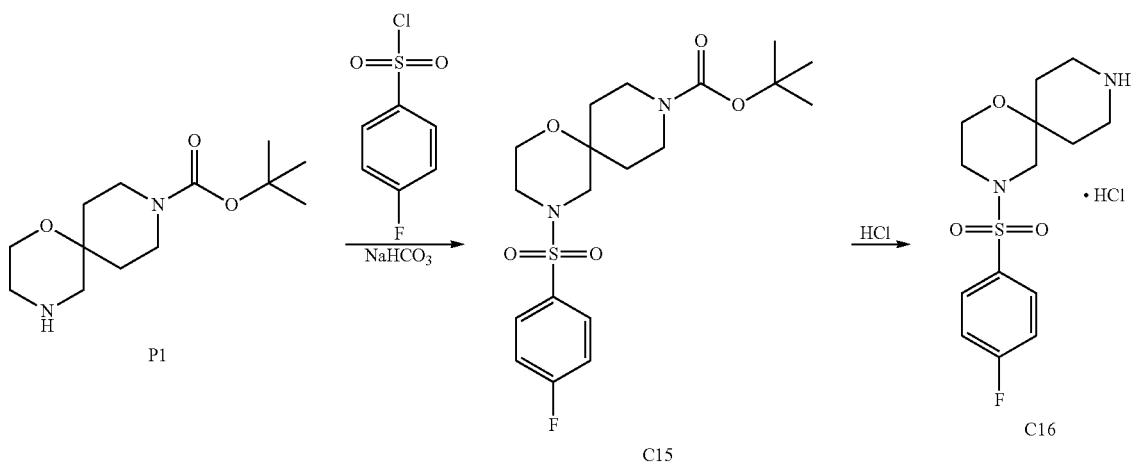

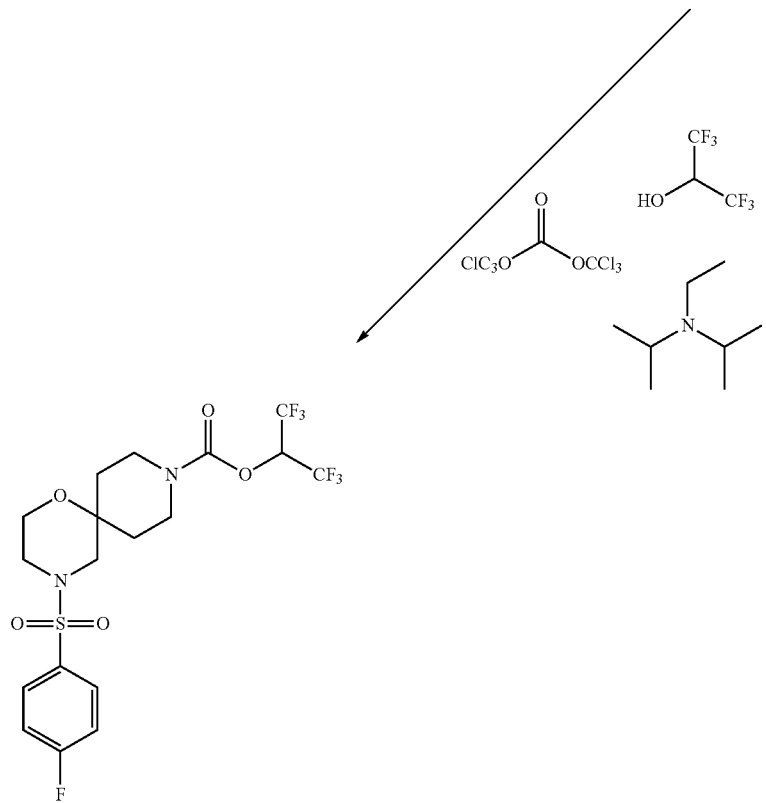

Step 1. Synthesis of tert-butyl 4-[(4-fluorophenyl)sulfonyl]-1-oxa-4,9-diazaspiro[5.5]undecane-9-carboxylate (C15)

4-Fluorobenzenesulfonyl chloride (4.18 g, 21.5 mmol) was added portion-wise to a mixture of P1 (5.0 g, 20 mmol), saturated aqueous sodium bicarbonate solution (55 mL), and dichloromethane (195 mL). The reaction mixture was stirred at room temperature overnight, whereupon the aqueous layer was extracted twice with dichloromethane, and the combined organic layers were dried over magnesium sulfate, filtered, and concentrated in vacuo. Silica gel chromatography (Gradient: 0% to 10% methanol in dichloromethane) afforded the product as a white foam. Yield: 8.4 g, 20 mmol, quantitative. $^1$H NMR (400 MHz, CDCl$_3$) δ 7.79-7.73 (m, 2H), 7.28-7.22 (m, 2H, assumed; partially obscured by solvent peak), 3.8-3.66 (m, 2H), 3.79 (dd, J=5.0, 5.0 Hz, 2H), 3.19-3.08 (m, 2H), 3.08-2.89 (m, 2H), 2.89-2.67 (m, 2H), 1.96-1.82 (m, 2H), 1.54-1.48 (m, 2H), 1.47 (s, 9H).

Step 2. Synthesis of 4-[(4-fluorophenyl)sulfonyl]-1-oxa-4,9-diazaspiro[5.5]undecane, hydrochloride salt (C16)

A mixture of C15 (150 mg, 0.362 mmol) and a solution of hydrogen chloride in ethyl acetate (20 mL) was stirred at room temperature for 1 hour, whereupon the reaction mixture was concentrated in vacuo. The residue was washed with tert-butyl methyl ether (50 mL) to provide the product as a white solid. Yield: 105 mg, 0.299 mmol, 83%. LCMS m/z 315.1 [M+H]$^+$.

Step 3. Synthesis of 1,1,1,3,3,3-hexafluoropropan-2-yl 4-[(4-fluorophenyl)sulfonyl]-1-oxa-4,9-diazaspiro[5.5]undecane-9-carboxylate (2)

1,1,1,3,3,3-Hexafluoropropan-2-ol (3.00 g, 17.9 mmol) was added to a 0° C. solution of bis(trichloromethyl) carbonate (1.75 g, 5.90 mmol) and N,N-diisopropylethylamine (2.99 g, 23.1 mmol) in dichloromethane (20 mL), and the reaction mixture was stirred at 20° C. for 14 hours. A portion of this reaction mixture (1 mL, ~0.6 mmol) was slowly added to a 0° C. solution of C16 (105 mg, 0.299 mmol) and N,N-diisopropylethylamine (45 mg, 0.35 mmol) in dichloromethane (10 mL). More N,N-diisopropylethylamine (45 mg, 0.35 mmol) was slowly added while the reaction mixture remained at 0° C., whereupon the reaction mixture was stirred for 12 hours at room temperature. It was then carefully added to ice water, and the resulting mixture was adjusted to pH 7 by addition of dilute hydrochloric acid and extracted with dichloromethane (3×30 mL). The combined organic layers were washed sequentially with water (15 mL) and saturated aqueous sodium chloride solution (15 mL), dried over sodium sulfate, filtered, and concentrated in vacuo. The residue was purified via reversed-phase HPLC (Column: Phenomenex Gemini C18, 10 μm; Mobile phase A: 0.225% formic acid in water; Mobile phase B: acetonitrile; Gradient: 45% to 75% B) to provide the product as a solid. Yield: 65.0 mg, 0.123 mmol, 41%. LCMS m/z 509.0 [M+H]$^+$. $^1$H NMR (400 MHz, CDCl$_3$) δ 7.79-7.73 (m, 2H), 7.26 (br dd, J=8.6, 8.4 Hz, 2H), 5.76 (septet, J=6.2 Hz, 1H), 3.96-3.84 (m, 2H), 3.80 (dd, J=5.1, 4.8 Hz, 2H), 3.33-3.18 (m, 2H), 3.07-2.95 (m, 2H), 2.80 (AB quartet, J$_{AB}$=11.4 Hz, Δν$_{AB}$=14.5 Hz, 2H), 2.06-1.97 (m, 2H), 1.6-1.45 (m, 2H, assumed; partially obscured by water peak).

Example 3

1,1,1,3,3,3-Hexafluoropropan-2-yl 4-(tetrahydro-2H-pyran-3-ylmethyl)-1-oxa-4,9-diazaspiro[5.5]undecane-9-carboxylate (3)

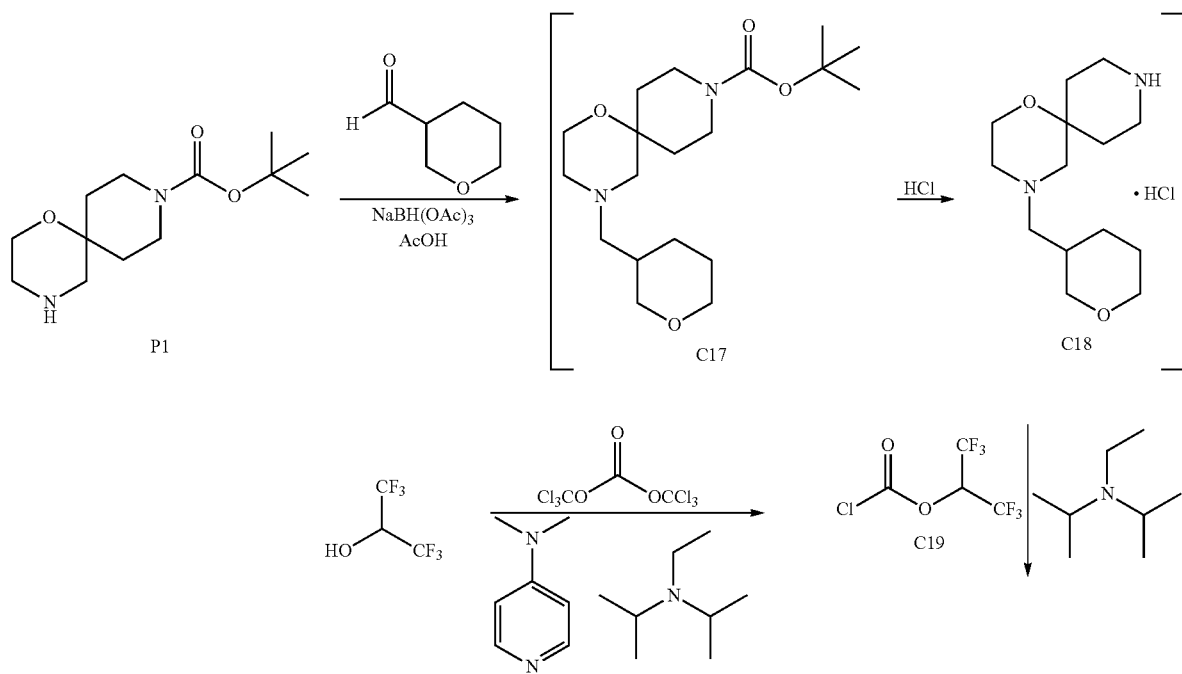

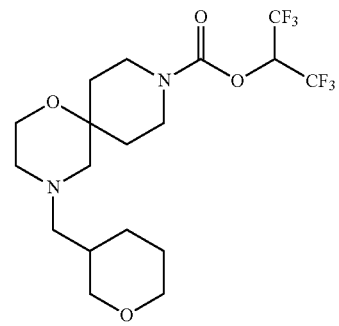

This synthesis was carried out in library format. A mixture of tetrahydro-2H-pyran-3-carbaldehyde (163 μmol, 1.3 equivalents) and P1 [0.125 M solution in (0.0125 M solution of acetic acid in 1,2-dichloroethane); 1.0 mL, 125 μmol, 1.0 equivalent] was shaken at 30° C. for 16 hours in a closed vial, whereupon sodium triacetoxyborohydride (250 μmol, 2.0 equivalents) was added, and shaking was continued at 30° C. for an additional 16 hours. Solvent was removed using a SpeedVac evaporator, and the residue was purified via preparative thin-layer chromatography on silica gel to provide C17 (tert-butyl 4-(tetrahydro-2H-pyran-3-ylmethyl)-1-oxa-4,9-diazaspiro[5.5]undecane-9-carboxylate). This material was dissolved in methanol (500 μL), treated with hydrogen chloride in methanol (4.0 M; 1.0 mL, 4.0 mmol), and shaken at 30° C. for 2 hours. Concentration using a SpeedVac evaporator provided intermediate C18 (4-(tetrahydro-2H-pyran-3-ylmethyl)-1-oxa-4,9-diazaspiro [5.5]undecane, hydrochloride salt). In a separate vial, a solution of bis(trichloromethyl) carbonate (0.33 equivalents) in dichloromethane (1.0 mL) was added to a 0° C. solution of 1,1,1,3,3,3-hexafluoropropan-2-ol (1.0 equivalent), 4-(dimethylamino)pyridine (0.1 equivalents), and N,N-diisopropylethylamine (1.0 equivalent) in dichloromethane (1.0 mL), and the reaction mixture was allowed to stir at 0° C. for 30 minutes, then at 30° C. for 16 hours to afford a solution of C19 (1,1,1,3,3,3-hexafluoropropan-2-yl carbonochloridate).

The C18 synthesized above was dissolved in dichloromethane (1.0 mL) and treated with N,N-diisopropylethylamine (4.0 equivalents). The solution of C19 synthesized above was added, and the reaction mixture was allowed to stir at 30° C. for 16 hours. After removal of volatiles using a SpeedVac evaporator, the residue was purified via reversed-phase HPLC (Column: Phenomenex Gemini C18, 8 μm; Mobile phase A: ammonium hydroxide in water, pH 10; Mobile phase B: acetonitrile; Gradient: 53% to 93% B) to provide the product. Yield: 6.1 mg, 14 μmol, 11%. LCMS m/z 449 [M+H]$^+$. Retention time 2.75 minutes (Analytical conditions, Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

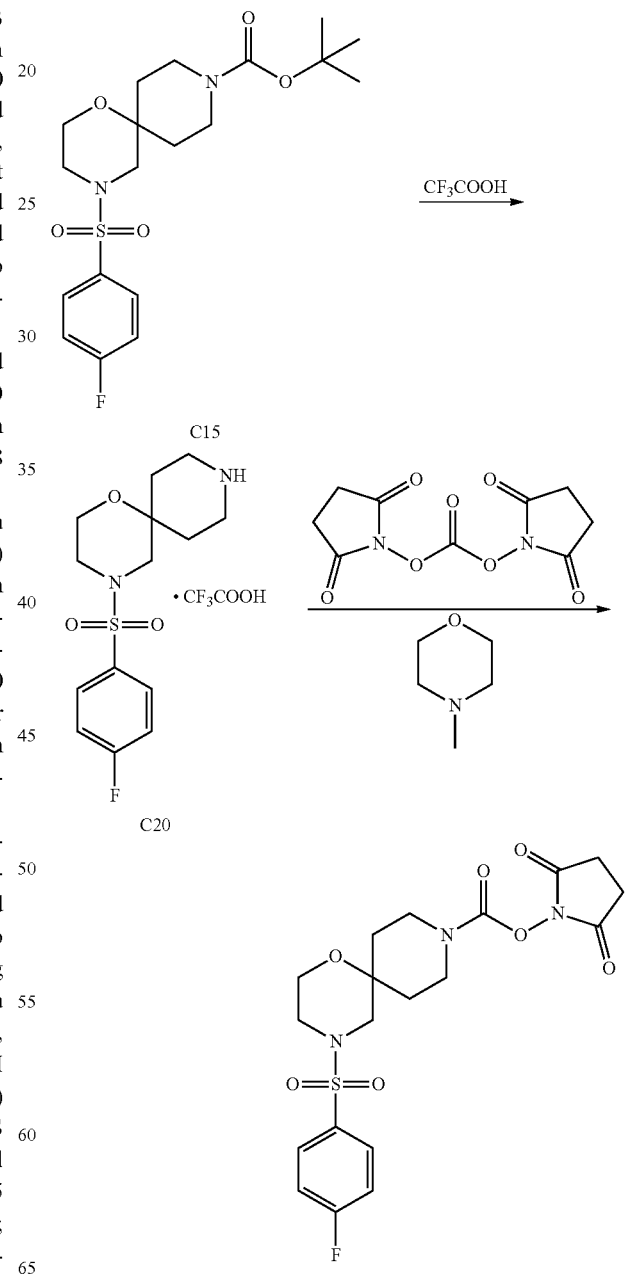

Step 1. Synthesis of 4-[(4-fluorophenyl)sulfonyl]-1-oxa-4,9-diazaspiro[5.5]undecane, trifluoroacetic acid salt (C20)

Trifluoroacetic acid (2 mL) was added to a solution of C15 (100 mg, 0.24 mmol) in dichloromethane (12 mL) at room temperature, and the reaction mixture was stirred at room temperature for 2 hours. Concentration in vacuo provided the product as a yellow gum, a portion of which was used directly in the following step.

Step 2. Synthesis of 1-[({[4-[(4-fluorophenyl)sulfonyl]-1-oxa-4,9-diazaspiro[5.5]undec-9-yl}carbonyl)oxy]pyrrolidine-2,5-dione (4)

4-Methylmorpholine (37 mg, 0.37 mmol) and C20 (half of the material from the previous step; ≤0.12 mmol) were added to a solution of N,N'-disuccinimidyl carbonate (31 mg, 0.12 mmol) in dichloromethane (3 mL). After the reaction mixture had been stirred at room temperature overnight, it was concentrated in vacuo and purified via preparative thin-layer chromatography on silica gel (Eluent: 10:1 dichloromethane/methanol), affording the product as a white solid. Yield: 16 mg, 35 μmol, 29% over two steps. LCMS m/z 477.9 [M+Na⁺]. ¹H NMR (400 MHz, CDCl₃) δ 7.81-7.74 (m, 2H), 7.30-7.22 (m, 2H, assumed; partially obscured by solvent peak), 4.02-3.91 (m, 1H), 3.91-3.82 (m, 1H), 3.80 (dd, J=5.0, 4.5 Hz, 2H), 3.41-3.31 (m, 1H), 3.29-3.19 (m, 1H), 3.07-2.95 (m, 2H), 2.88-2.76 (m, 2H), 2.83 (s, 4H), 2.08-1.97 (m, 2H), 1.70-1.53 (m, 2H, assumed; partially obscured by water peak).

Example 5

1-{[(4-Benzyl-1-oxa-4,9-diazaspiro[5.5]undec-9-yl)carbonyl]oxy}pyrrolidine-2,5-dione (5)

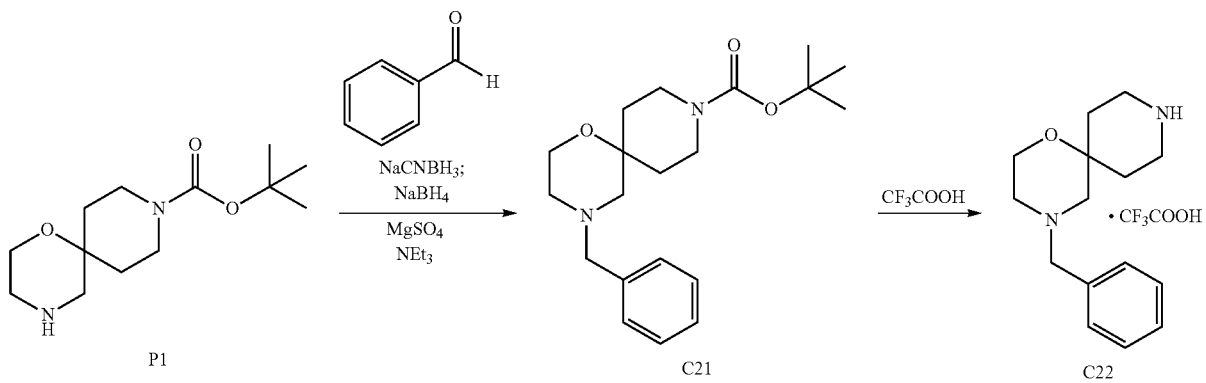

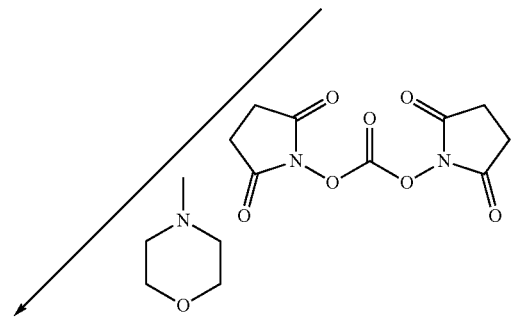

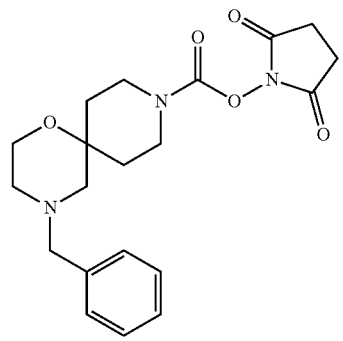

Step 1. Synthesis of tert-butyl 4-benzyl-1-oxa-4,9-diazaspiro[5.5]undecane-9-carboxylate (C21)

To a 28° C. suspension of P1 (80 mg, 0.31 mmol) in ethanol (1.5 mL) were added benzaldehyde (66 mg, 0.62 mmol), magnesium sulfate (113 mg, 0.939 mmol), sodium cyanoborohydride (98.1 mg, 1.56 mmol), and triethylamine (253 mg, 2.50 mmol). The reaction mixture was stirred at 45° C. for 14 hours, whereupon it was treated with additional sodium cyanoborohydride (100 mg, 1.59 mmol) and stirring was continued at 45° C. for 16 hours. At this point, as LCMS analysis indicated persistence of the intermediate imine, sodium borohydride (35.4 mg, 0.936 mmol) was added. After the reaction mixture had been stirred at 45° C. for a further 16 hours, it was filtered. The filtrate was concentrated in vacuo and purified via silica gel chromatography (Gradient: 0% to 10% methanol in dichloromethane), affording impure product as a white solid. This material was taken directly to the following step. LCMS m/z 347.1 [M+H]$^+$.

Step 2. Synthesis of 4-benzyl-1-oxa-4,9-diazaspiro[5.5]undecane, trifluoroacetic acid salt (C22)

Trifluoroacetic acid (3 mL) was added to a 0° C. solution of C21 (from the previous step, ≤0.31 mmol) in dichloromethane (10 mL). The reaction mixture was stirred at 28° C. for 2 hours, whereupon it was concentrated in vacuo to provide the product as a yellow gum. This material was taken directly to the following step. LCMS m/z 278.9 [M+Na]$^+$.

Step 3. Synthesis of 1-{[(4-benzyl-1-oxa-4,9-diazaspiro[5.5]undec-9-yl)carbonyl]oxy}pyrrolidine-2,5-dione (5)

4-Methylmorpholine (117 mg, 1.16 mmol) was added to a 0° C. solution of C22 (from the previous step; ≤0.31 mmol) in dichloromethane (2 mL). N,N'-Disuccinimidyl carbonate (119 mg, 0.464 mmol) was added, and the reaction mixture was allowed to stir at 28° C. for 16 hours, whereupon it was diluted with water (10 mL) and extracted with ethyl acetate (3×15 mL). The combined organic layers were dried over sodium sulfate, filtered, and concentrated in vacuo. Purification via reversed-phase HPLC (Column: Agela Durashell C18, 5 μm; Mobile phase A: 0.05% ammonium hydroxide in water; Mobile phase B: acetonitrile; Gradient: 35% to 55% B) provided the product as a colorless gum. Yield: 4.2 mg, 11 μmol, 4% over 3 steps. LCMS m/z 388.2 [M+H]$^+$. $^1$H NMR (400 MHz, CDCl$_3$) δ 7.35-7.24 (m, 5H), 3.95-3.85 (m, 1H), 3.84-3.76 (m, 1H), 3.75 (dd, J=4.8, 4.8 Hz, 2H), 3.46 (s, 2H), 3.44-3.34 (m, 1H), 3.32-3.22 (m, 1H), 2.81 (s, 4H), 2.49-2.41 (m, 2H), 2.24 (s, 2H), 2.14-2.05 (m, 2H), 1.6-1.42 (m, 2H, assumed; partially obscured by water peak).

Example 6

1,1,1,3,3,3-Hexafluoropropan-2-yl (3R)-3-[methyl(phenylsulfonyl)amino]-1-oxa-8-azaspiro[4.5]decane-8-carboxylate (6)

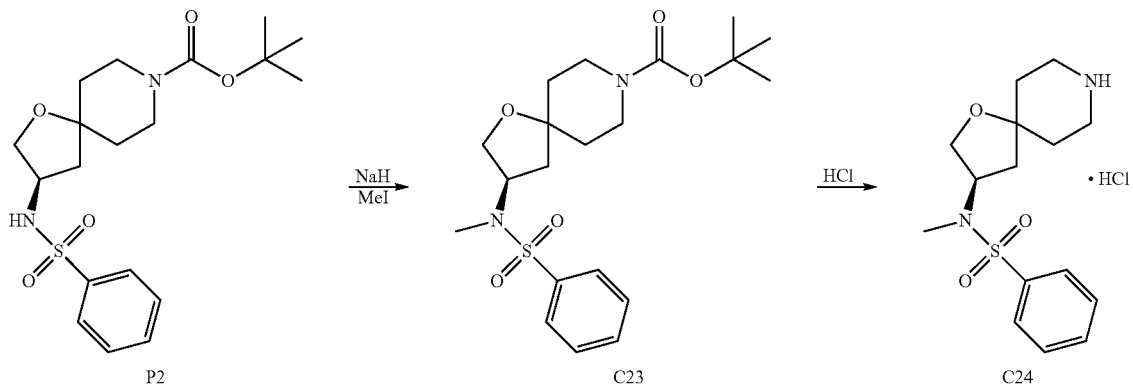

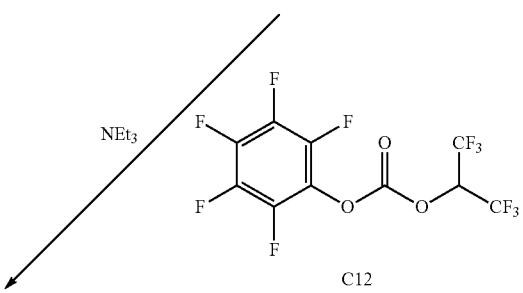

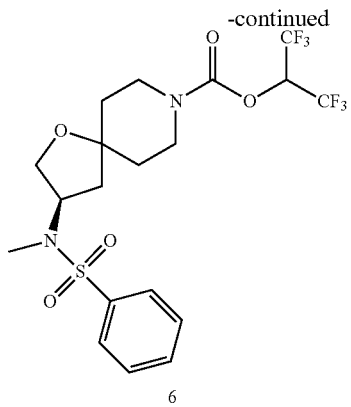

6

Step 1. Synthesis of tert-butyl (3R)-3-[methyl(phenylsulfonyl)amino]-1-oxa-8-azaspiro[4.5]decane-8-carboxylate (C23)

Sodium hydride (60% dispersion in mineral oil; 80.7 mg, 2.02 mmol) was added to a 0° C. solution of P2 (400 mg, 1.01 mmol) in N,N-dimethylformamide (10 mL), and the reaction mixture was stirred at 0° C. for 30 minutes. A solution of iodomethane (186 mg, 1.31 mmol) in N,N-dimethylformamide (0.5 mL) was slowly added to the cold reaction mixture, which was then allowed to stir at room temperature for 16 hours. LCMS of the reaction mixture: m/z 433.1 [M+Na$^+$]. After dilution with water (70 mL), the mixture was extracted with ethyl acetate (4×30 mL), and the combined organic layers were dried over sodium sulfate, filtered, and concentrated in vacuo. Chromatography on silica gel (Gradient: 0% to 50% ethyl acetate in petroleum ether) afforded the product as a white solid. Yield: 390 mg, 0.950 mmol, 94%. $^1$H NMR (400 MHz, CDCl$_3$) δ 7.79 (br d, J=8 Hz, 2H), 7.64-7.58 (m, 1H), 7.54 (br dd, half of ABX pattern, J=7.5, 7.5 Hz, 2H), 4.75-4.65 (m, 1H), 3.79 (dd, J=10.0, 7.5 Hz, 1H), 3.65-3.52 (m, 2H), 3.56 (dd, J=10.0, 5.0 Hz, 1H), 3.28-3.14 (m, 2H), 2.77 (s, 3H), 1.88 (dd, J=13.6, 9.0 Hz, 1H), 1.64-1.55 (m, 3H, assumed; partially obscured by water peak), 1.49-1.42 (m, 1H), 1.44 (s, 9H), 1.42-1.33 (m, 1H).

Step 2. Synthesis of N-methyl-N-[(3R)-1-oxa-8-azaspiro[4.5]dec-3-yl]benzenesulfonamide, hydrochloride salt (C24)

A solution of hydrogen chloride in 1,4-dioxane (2 mL) was added to a solution of C23 (385 mg, 0.938 mmol) in dichloromethane (8 mL) and the reaction mixture was stirred for 1 hour at 20° C. It was then concentrated under reduced pressure to provide crude product (350 mg) as a white solid. Portions of this material were used directly for synthesis of Examples 6 and 7, without further purification. $^1$H NMR (400 MHz, CD$_3$OD) δ 7.86 (m, 2H), 7.71-7.66 (m, 1H), 7.64-7.58 (m, 2H), 4.76-4.68 (m, 1H), 3.82 (dd, J=10.3, 7.3 Hz, 1H), 3.59 (dd, J=10.5, 5.0 Hz, 1H), 3.23-3.12 (m, 4H), 2.77 (s, 3H), 2.01-1.85 (m, 4H), 1.71-1.61 (m, 1H), 1.60 (dd, J=13.6, 7.0 Hz, 1H).

Another portion of the crude product (110 mg) was used for neutralization and purification, as follows. This material was dissolved in methanol (5 mL) and treated with Amberlyst A-21 ion-exchange resin (400 mg; pre-washed with 20 mL of methanol); the resulting mixture was stirred at 23° C. for 2 hours and then filtered. The filtrate was concentrated in vacuo, and the residue was purified via reversed-phase HPLC (Column: Waters XBridge C18 OBD, 5 μm; Mobile phase A: water containing 0.05% ammonium hydroxide; Mobile phase B: acetonitrile; Gradient: 5% to 95% B), affording the free base of C24 as a brown oil. Adjusted total yield, based on purified neutralized product (free base of C24): 60.8 mg, 0.196 mmol, 67%. LCMS of free base of C24: m/z 310.9 [M+H]$^+$. $^1$H NMR of free base of C24: (400 MHz, CD$_3$OD) δ 7.86-7.81 (m, 2H), 7.71-7.65 (m, 1H), 7.64-7.58 (m, 2H), 4.73-4.64 (m, 1H), 3.79 (dd, J=10.3, 7.3 Hz, 1H), 3.54 (dd, J=10.0, 5.0 Hz, 1H), 3.03-2.90 (m, 2H), 2.90-2.81 (m, 2H), 2.76 (s, 3H), 1.92 (dd, J=13.6, 9.0 Hz, 1H), 1.77-1.67 (m, 3H), 1.58-1.49 (m, 1H), 1.49 (dd, J=13.6, 7.0 Hz, 1H).

Step 3. Synthesis of 1,1,1,3,3,3-hexafluoropropan-2-yl (3R)-3-[methyl(phenylsulfonyl)amino]-1-oxa-8-azaspiro[4.5]decane-8-carboxylate (6)

A solution of C24 (from the previous step; 130 mg, ≤0.347 mmol) and triethylamine (240 mg, 2.37 mmol) in acetonitrile (2 mL) was added in a drop-wise manner to a 0° C. solution of C12 (reaction solution in acetonitrile, containing 0.68 mmol). After the reaction mixture had stirred at room temperature for 16 hours, it was treated with additional C12 (reaction solution in acetonitrile, containing 0.68 mmol), and stirring was continued for 20 hours at room temperature. The reaction mixture was then concentrated in vacuo, and the residue was purified via reversed-phase HPLC (Column: Daiso C18, 5 µm; Mobile phase A: 0.225% formic acid in water; Mobile phase B: acetonitrile; Gradient: 30% to 60% B), providing the product as a colorless oil. Yield: 91.6 mg, 0.182 mmol, 52% over 2 steps. LCMS m/z 527.1 [M+Na$^+$]. $^1$H NMR (400 MHz, CD$_3$OD) δ 7.85-7.80 (m, 2H), 7.70-7.64 (m, 1H), 7.63-7.57 (m, 2H), 6.09 (septet, J=6.4 Hz, 1H), 4.74-4.66 (m, 1H), 3.80 (dd, J=10.0, 7.3 Hz, 1H), 3.76-3.66 (m, 2H), 3.55 (dd, J=10.0, 5.0 Hz, 1H), 3.42-3.24 (m, 2H, assumed; partially obscured by solvent peak), 2.76 (s, 3H), 1.92 (dd, J=13.6, 9.0 Hz, 1H), 1.74-1.61 (m, 3H), 1.52 (dd, J=13.6, 6.8 Hz, 1H), 1.51-1.39 (m, 1H).

Example 7

N-[(3R)-8-{[(2,5-Dioxopyrrolidin-1-yl)oxy]carbonyl}-1-oxa-8-azaspiro[4.5]dec-3-yl]-N-methylbenzenesulfonamide (7)

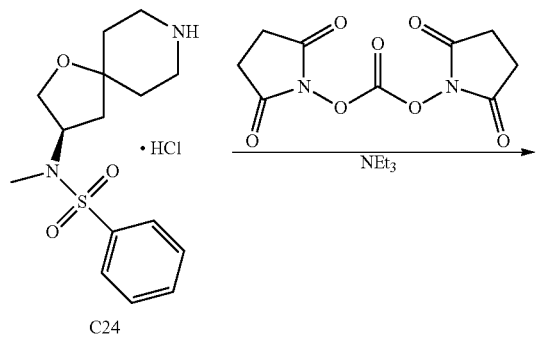

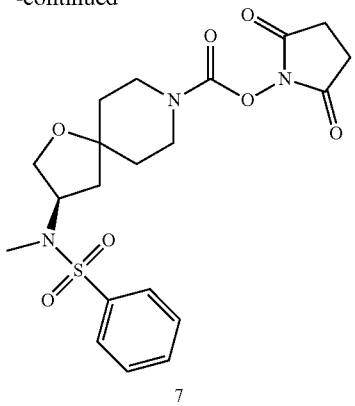

Triethylamine (166 mg, 1.64 mmol) was added to a 0° C. mixture of C24 (from Step 2 in Example 6; 90 mg, ≤0.243 mmol) and N,N'-disuccinimidyl carbonate (66.1 mg, 0.258 mmol) in acetonitrile (3 mL). The reaction mixture was stirred at room temperature for 20 hours, whereupon it was concentrated in vacuo. The residue was purified via reversed-phase HPLC (Column: Daiso C18, 5 µm; Mobile phase A: 0.225% formic acid in water; Mobile phase B: acetonitrile; Gradient: 32% to 62% B), affording the product as a white solid. Yield: 56.3 mg, 0.125 mmol, 51% over 2 steps. LCMS m/z 474.0 [M+Na$^+$]. $^1$H NMR (400 MHz, CD$_3$OD) δ 7.86-7.81 (m, 2H), 7.71-7.65 (m, 1H), 7.64-7.58 (m, 2H), 4.75-4.66 (m, 1H), 3.87-3.75 (br m, 1H), 3.82 (dd, J=10.0, 7.3 Hz, 1H), 3.74-3.65 (br m, 1H), 3.57 (dd, J=10.0, 5.0 Hz, 1H), 3.50-3.3 (br m, 2H, assumed; partially obscured by solvent peak), 2.80 (s, 4H), 2.77 (s, 3H), 1.93 (dd, J=13.6, 9.0 Hz, 1H), 1.81-1.67 (br m, 3H), 1.64-1.47 (br m, 1H), 1.53 (dd, J=13.4, 6.6 Hz, 1H).

Example 8

1,1,1,3,3,3-Hexafluoropropan-2-yl 2-benzoyl-2,8-diazaspiro[4.5]decane-8-carboxylate (8)

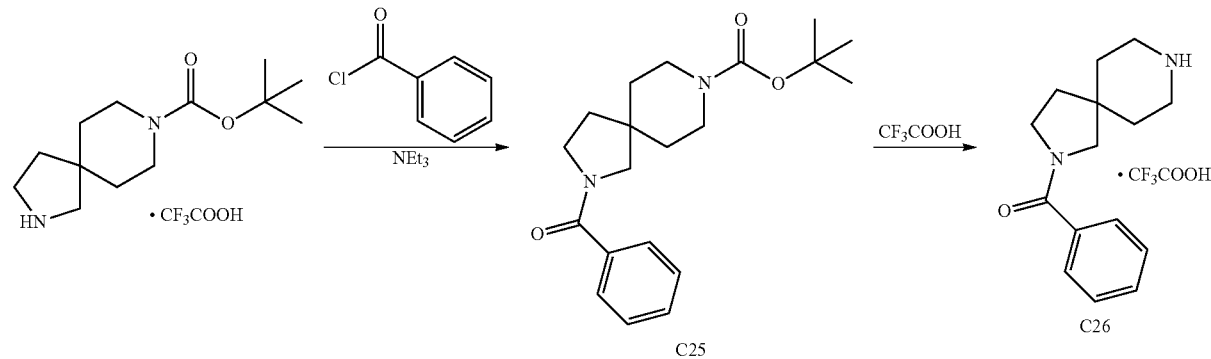

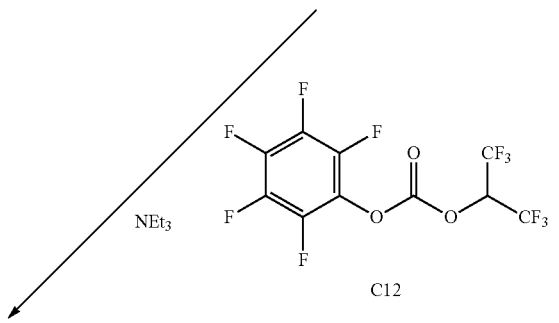

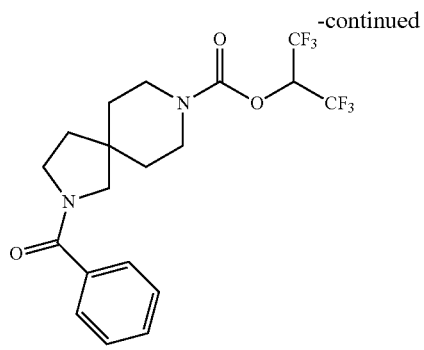

8

Step 1. Synthesis of tert-butyl 2-benzoyl-2,8-diazaspiro[4.5]decane-8-carboxylate (C25)

Benzoyl chloride (155 mg, 1.10 mmol) was added to a 0° C. solution of tert-butyl 2,8-diazaspiro[4.5]decane-8-carboxylate, trifluoroacetate salt (300 mg, 0.847 mmol) and triethylamine (257 mg, 2.54 mmol) in dichloromethane (8 mL), and the reaction mixture was allowed to slowly warm to room temperature and stir for 2.5 hours. After removal of volatiles under reduced pressure, the residue was purified via silica gel chromatography (Gradient: 17% to 33% ethyl acetate in petroleum ether), providing the product as a colorless gum. From analysis of the $^1$H NMR, this material was presumed to exist as a mixture of rotamers. Yield: 250 mg, 0.726 mmol, 86%. $^1$H NMR (400 MHz, CDCl$_3$) δ 7.54-7.47 (m, 2H), 7.46-7.38 (m, 3H), 3.74 (dd, J=7.5, 7.0 Hz, 1H), 3.64-3.49 (m, 3H), 3.42-3.26 (m, 4H), [1.87 (dd, J=7.5, 7.0 Hz) and 1.78 (dd, J=7.0, 7.0 Hz), total 2H], 1.68-1.5 (m, 4H, assumed; partially obscured by water peak), [1.48 (s) and 1.44 (s), total 9H].

Step 2. Synthesis of 2,8-diazaspiro[4.5]dec-2-yl (phenyl)methanone, trifluoroacetic acid salt (C26)

Trifluoroacetic acid (1.0 mL) was added to a 0° C. solution of C25 (150 mg, 0.435 mmol) in dichloromethane (3 mL). The reaction mixture was stirred at room temperature (29° C.) for 5 hours, whereupon it was concentrated in vacuo. The product was obtained as a pale yellow gum, which was used directly in the next step.

Step 3. Synthesis of 1,1,1,3,3,3-hexafluoropropan-2-yl 2-benzoyl-2,8-diazaspiro[4.5]decane-8-carboxylate (8)

Triethylamine (176 mg, 1.74 mmol) was slowly added to a 0° C. solution of C26 (from the previous step; 0.435 mmol) in acetonitrile (5 mL). After the mixture had been stirred for 30 minutes at 0° C., C12 (reaction solution in acetonitrile, containing 0.89 mmol) was added, and the reaction mixture was stirred at 26° C. for 18 hours. It was then concentrated in vacuo, and the residue was dissolved in ethyl acetate (20 mL), washed sequentially with water (2×10 mL) and saturated aqueous sodium chloride solution, dried over sodium sulfate, filtered, and concentrated under reduced pressure. Purification via reversed-phase HPLC (Column: Agela Durashell C18, 5 μm; Mobile phase A: 0.225% formic acid in water; Mobile phase B: acetonitrile; Gradient: 40% to 60% B) provided the product as a colorless gum. From analysis of the $^1$H NMR, this material was presumed to exist as a mixture of rotamers. Yield: 129 mg, 0.294 mmol, 68% over 2 steps. LCMS m/z 439.0 [M+H]$^+$. $^1$H NMR (400 MHz, CDCl$_3$) δ 7.55-7.38 (m, 5H), 5.82-5.67 (m, 1H), 3.81-3.69 (m, 2H), [3.60 (s) and 3.32 (s), total 2H], 3.59-3.39 (m, 4H), [1.91 (dd, J=7.5, 7.5 Hz) and 1.82 (dd, J=7.5, 7.0 Hz), total 2H], 1.77-1.49 (br m, 4H, assumed; partially obscured by water peak).

Example 9

1-{[(2-Benzoyl-2,8-diazaspiro[4.5]dec-8-yl)carbonyl]oxy}pyrrolidine-2,5-dione (9)

To a 0° C. solution of C26 (104 mg, 0.28 mmol) and triethylamine (88.1 mg, 0.871 mmol) in acetonitrile (5 mL) was added N,N'-disuccinimidyl carbonate (112 mg, 0.437 mmol), and the reaction mixture was allowed to slowly warm to room temperature (26° C.) and stir for 18 hours. After solvent had been removed in vacuo, the residue was dissolved in ethyl acetate (20 mL) and sequentially washed with water (2×10 mL) and saturated aqueous sodium chloride solution, dried over sodium sulfate, filtered, and concentrated under reduced pressure. The residue was purified using reversed-phase HPLC (Column: Agela Durashell C18, 5 μm; Mobile phase A: 0.225% formic acid in water; Mobile phase B: acetonitrile; Gradient: 15% to 35% B), affording the product as a white solid. From analysis of the $^1$H NMR, this material was presumed to exist as a mixture of rotamers. Yield: 77.8 mg, 0.202 mmol, 72%. LCMS m/z 386.1 [M+H]$^+$. $^1$H NMR (400 MHz, CDCl$_3$) δ 7.54-7.37 (m, 5H), 3.86-3.65 (m, 2H), 3.62-3.38 (m, 4H), [3.59 (s) and 3.32 (s), total 2H], [2.83 (s) and 2.80 (s), total 4H], [1.91 (dd, J=7.5, 7.0 Hz) and 1.82 (dd, J=7.0, 7.0 Hz), total 2H], 1.8-1.53 (m, 4H, assumed; partially obscured by water peak).

Example 10

4-(8-{[(2,5-Dioxopyrrolidin-1-yl)oxy]carbonyl}-1-oxa-8-azaspiro[4.5]dec-3-yl)benzonitrile (10)

mg, 3.12 mmol), trans-2-aminocyclohexanol (36.0 mg, 0.312 mmol), and nickel iodide (97.6 mg, 0.312 mmol) in 2-propanol (previously dried over activated 4 Å molecular sieves; 10 mL), and the reaction mixture was heated at 60° C. for 16 hours. It was then combined with a similar reaction mixture derived from P3 (30 mg, 94 μmol) and concentrated in vacuo. The residue was purified using silica gel chromatography (Gradient: from 0% to 20% ethyl acetate in petroleum ether) to afford the product as a white solid. Combined yield: 420 mg, 1.23 mmol, 74%. LCMS m/z 286.9 [(M-2-methylprop-1-ene)+H]$^+$. $^1$H NMR (400 MHz, CDCl$_3$) δ 7.61 (br d, J=8.5 Hz, 2H), 7.36 (br d, J=8.0 Hz, 2H), 4.24 (dd, J=8.5, 7.5 Hz, 1H), 3.81 (dd, J=9.0, 8.5 Hz, 1H), 3.72-3.60 (br m, 2H), 3.61-3.51 (m, 1H), 3.41-3.29 (m, 2H), 2.30 (dd, J=12.6, 8.0 Hz, 1H), 1.79 (dd, J=12.6, 10.0 Hz, 1H), [1.78-1.67 (m) and 1.63-1.51 (m), total 4H, assumed; partially obscured by water peak], 1.47 (s, 9H).

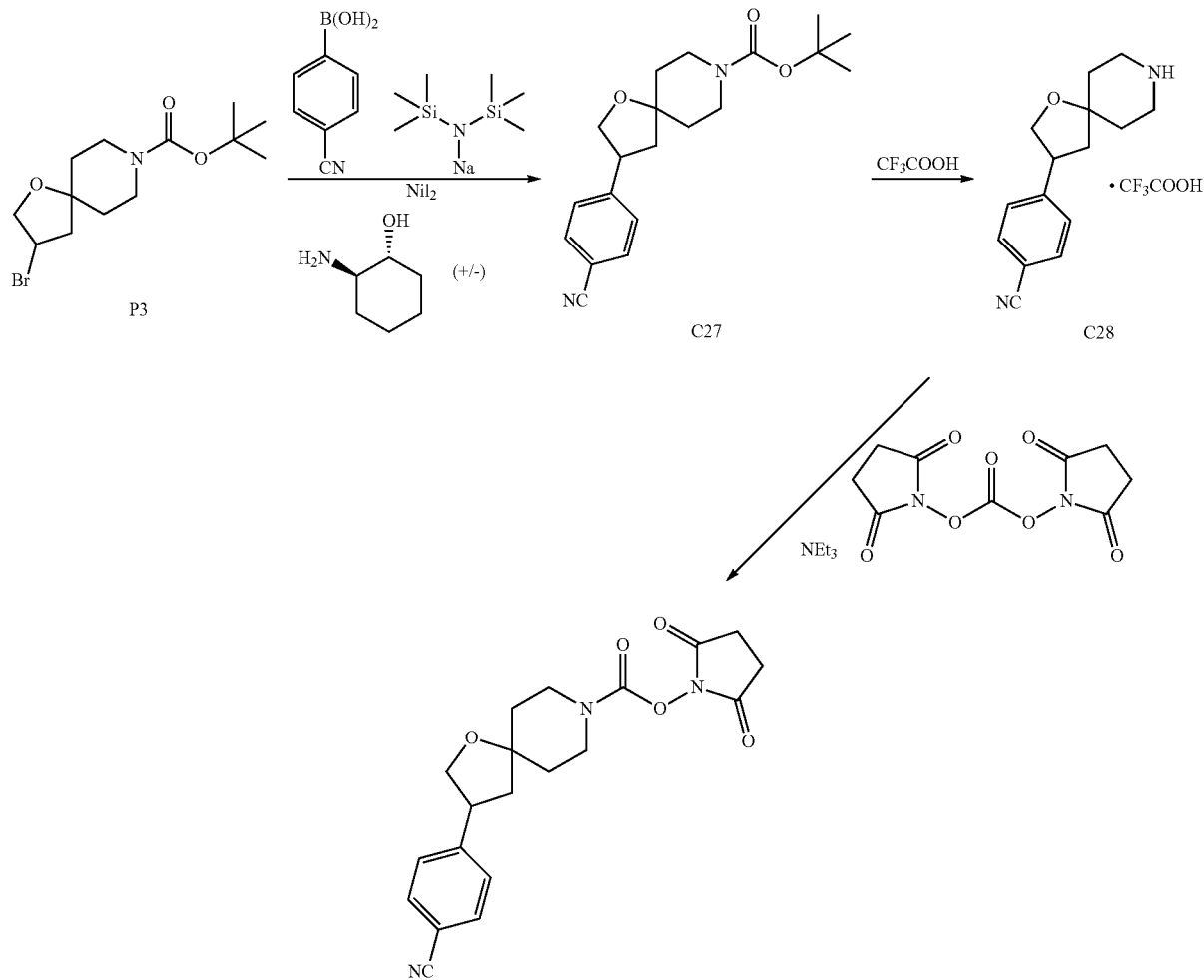

Step 1. Synthesis of tert-butyl 3-(4-cyanophenyl)-1-oxa-8-azaspiro[4.5]decane-8-carboxylate (C27)

Sodium bis(trimethylsilyl)amide (1 M solution in tetrahydrofuran; 3.12 mL, 3.12 mmol) was added to a mixture of P3 (500 mg, 1.56 mmol), (4-cyanophenyl)boronic acid (459

Step 2. Synthesis of 4-(1-oxa-8-azaspiro[4.5]dec-3-yl)benzonitrile, Trifluoroacetic Acid Salt (C28)

Trifluoroacetic acid (1 mL) was added to a 0° C. solution of C27 (90 mg, 0.26 mmol) in dichloromethane (4 mL). The reaction mixture was stirred at 28° C. for 1 hour, whereupon it was concentrated in vacuo to afford the product as a colorless gum; this material was used directly in the following step. LCMS m/z 243.0 [M+H]+.

Step 3. Synthesis of 4-(8-{[(2,5-dioxopyrrolidin-1-yl)oxy)carbonyl}-1-oxa-8-azaspiro[4.5]dec-3-yl)benzonitrile (10)

A 0° C. mixture of C28 (from the previous step; ≤0.26 mmol) in acetonitrile (5 mL) was treated with triethylamine (187 mg, 1.85 mmol), and the mixture was stirred for 10 minutes at 0° C. N,N'-Disuccinimidyl carbonate (81.1 mg, 0.317 mmol) was added, and stirring was continued at 28° C. (room temperature) for 15 hours. The reaction mixture was then concentrated in vacuo and purified via reversed-phase HPLC (Column: Agela Durashell C18, 5 μm; Mobile phase A: 0.225% formic acid in water; Mobile phase B: acetonitrile; Gradient: 25% to 45% B), affording the product as a white solid. Yield: 48.6 mg, 0.127 mmol, 49% over 2 steps. LCMS m/z 384.2 [M+H]+. 1H NMR (400 MHz, CDCl3) δ 7.62 (br d, J=8.4 Hz, 2H), 7.35 (br d, J=8.4 Hz, 2H), 4.25 (dd, J=8.6, 7.7 Hz, 1H), 4.01-3.91 (br m, 1H), 3.91-3.82 (br m, 1H), 3.82 (dd, J=8.8, 8.8 Hz, 1H), 3.63-3.32 (m, 3H), 2.83 (s, 4H), 2.31 (dd, J=12.8, 8.4 Hz, 1H), 1.93-1.65 (br m, 4H), 1.84 (dd, J=12.8, 9.7 Hz, 1H).

Example 11

1,1,1,3,3,3-Hexafluoropropan-2-yl 3-(4-cyanophenyl)-1-oxa-8-azaspiro[4.5]decane-8-carboxylate (11)

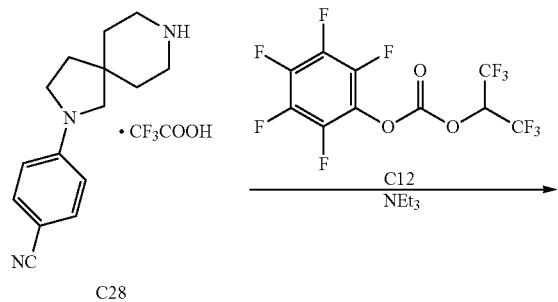

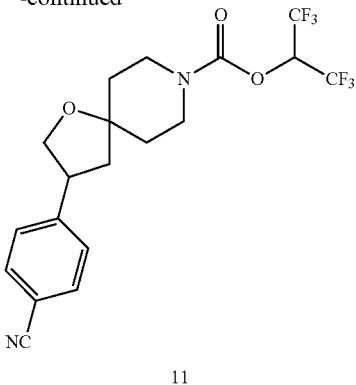

Triethylamine (187 mg, 1.85 mmol) was added to a solution of C28 (94 mg, 0.26 mmol) in acetonitrile (5 mL) and the mixture was stirred for 10 minutes. It was then cooled to 0° C., and treated in a drop-wise manner with C12 (reaction solution in acetonitrile, containing 0.60 mmol), whereupon the reaction mixture was allowed to warm to room temperature (28° C. to 30° C.) and stir for 16 hours. It was then concentrated in vacuo and the residue was purified using reversed-phase HPLC (Column: Agela Durashell C18, 5 μm; Mobile phase A: 0.225% formic acid in water; Mobile phase B: acetonitrile; Gradient: 50% to 70% B), to afford the product as a white solid. Yield: 24.5 mg, 56.1 μmol, 22%. LCMS m/z 437.1 [M+H]+. 1H NMR (400 MHz, CDCl3) 7.62 (br d, J=8.4 Hz, 2H), 7.35 (br d, J=8.4 Hz, 2H), 5.77 (septet, J=6.2 Hz, 1H), 4.25 (br dd, J=8.4, 7.9 Hz, 1H), 3.94-3.82 (m, 2H), 3.82 (dd, J=8.8, 8.8 Hz, 1H), 3.65-3.52 (m, 1H), 3.50-3.33 (m, 2H), 2.31 (dd, J=12.8, 8.4 Hz, 1H), 1.89-1.55 (m, 5H, assumed; partially obscured by water peak).

Example 12

1,1,1,3,3,3-Hexafluoropropan-2-yl (3R)-3-(4-fluoro-1H-pyrazol-1-yl)-1-oxa-8-azaspiro[4.5]decane-8-carboxylate (12)

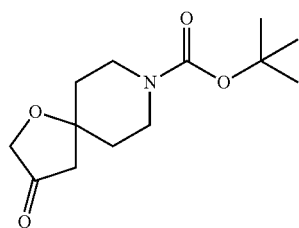

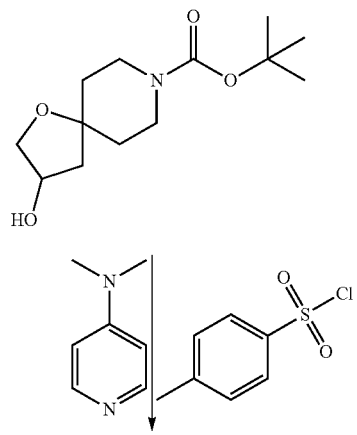

-continued
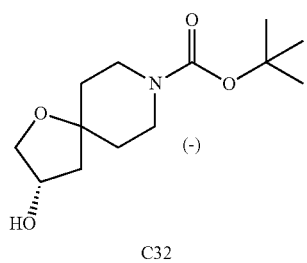
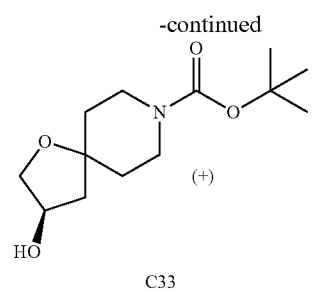
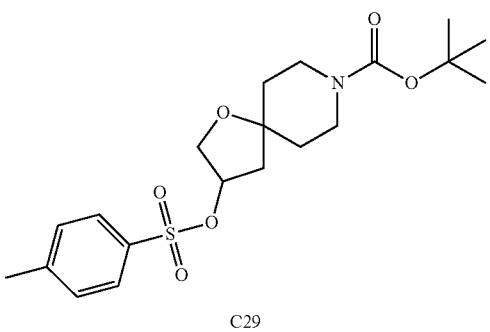
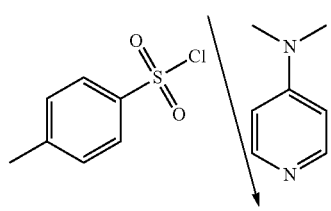
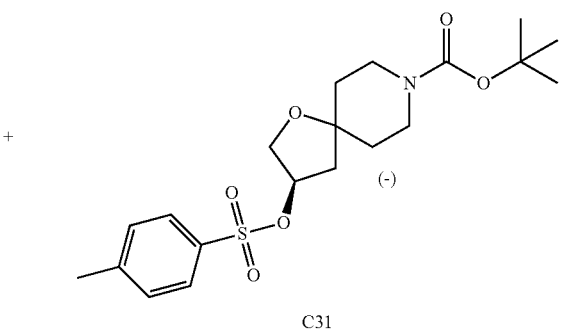
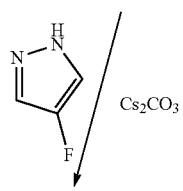
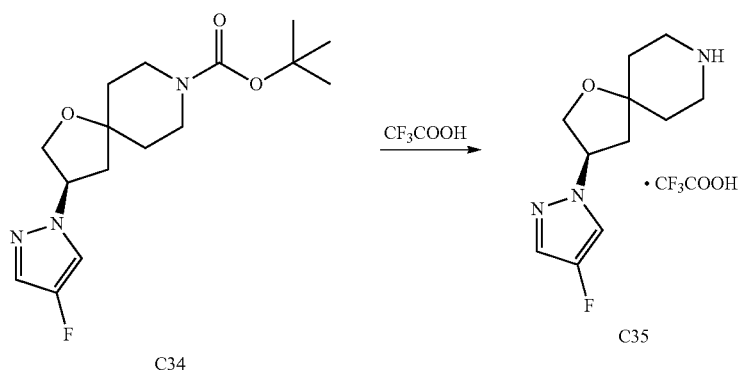

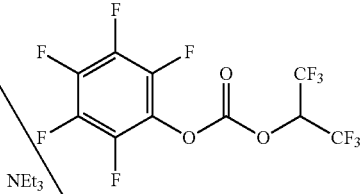

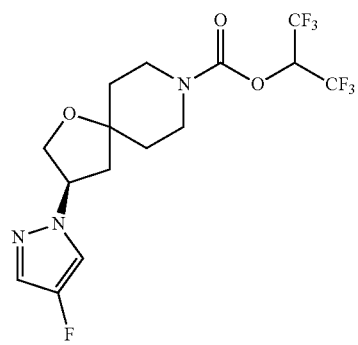

12

Step 1. Synthesis of tert-butyl 3-{[(4-methylphenyl)sulfonyl]oxy}-1-oxa-8-azaspiro[4.5]decane-8-carboxylate (C29)

p-Toluenesulfonyl chloride (359 mg, 1.88 mmol) and 4-(dimethylamino)pyridine (558 mg, 4.57 mmol) were added to a 27° C. solution of tert-butyl 3-hydroxy-1-oxa-8-azaspiro[4.5]decane-8-carboxylate (440 mg, 1.71 mmol) in dichloromethane (10 mL). The reaction mixture was stirred at 25° C. for 16 hours, whereupon it was combined with a similar reaction carried out with tert-butyl 3-hydroxy-1-oxa-8-azaspiro[4.5]decane-8-carboxylate (30 mg, 0.12 mmol) and concentrated in vacuo. The residue was purified using chromatography on silica gel (Gradient: 0% to 30% ethyl acetate in petroleum ether) to provide the product as a colorless gum. Combined yield: 640 mg, 1.56 mmol, 85%. LCMS m/z 434.0 [M+Na$^+$]. $^1$H NMR (400 MHz, CDCl$_3$) δ 7.79 (d, J=8.4 Hz, 2H), 7.36 (d, J=8.4 Hz, 2H), 5.13-5.06 (br m, 1H), 3.97-3.88 (m, 2H), 3.67-3.53 (br m, 2H), 3.31-3.19 (m, 2H), 2.46 (s, 3H), 2.01 (br dd, half of ABX pattern, J=14.3, 2.0 Hz, 1H), 1.93 (dd, half of ABX pattern, J=14.5, 6.6 Hz, 1H), 1.82-1.74 (m, 1H), 1.61-1.48 (m, 3H), 1.45 (s, 9H).

Step 2. Isolation of tert-butyl (3S)-3-{[(4-methylphenyl)sulfonyl]oxy}-1-oxa-8-azaspiro[4.5]decane-8-carboxylate (C30) and tert-butyl (3R)-3-{[(4-methylphenyl)sulfonyl]oxy}-1-oxa-8-azaspiro[4.5]decane-8-carboxylate (C31)

Supercritical fluid chromatography [Column: Chiral Technologies Chiralpak AD, 5 μm; Mobile phase: 3:2 carbon dioxide/(ethanol containing 0.1% ammonium hydroxide)] was used to separate C29 (from the previous step; 640 mg, 1.56 mmol) into its component enantiomers. The first-eluting product, obtained as a colorless gum that exhibited a positive (+) rotation, was designated as C30. The indicated absolute stereochemistry of C30 was established on the basis of an X-ray crystal structure determined on its enantiomer C31 (see below). Yield: 259 mg, 0.629 mmol, 40%. LCMS m/z 434.0 [M+Na$^+$]. $^1$H NMR (400 MHz, CDCl$_3$) δ 7.79 (br d, J=8.0 Hz, 2H), 7.36 (d, J=8.0 Hz, 2H), 5.14-5.06 (br m, 1H), 3.97-3.89 (m, 2H), 3.67-3.54 (br m, 2H), 3.31-3.20 (m, 2H), 2.47 (s, 3H), 2.01 (br dd, half of ABX pattern, J=14.3, 1.8 Hz, 1H), 1.93 (dd, half of ABX pattern, J=14.6, 6.5 Hz, 1H), 1.82-1.74 (m, 1H), 1.60-1.48 (m, 3H), 1.45 (s, 9H). The second-eluting product, also obtained as a colorless gum, exhibited a negative (−) rotation and was designated as C31. Yield: 263 mg, 0.639 mmol, 41%. LCMS m/z 434.1 [M+Na$^+$]. $^1$H NMR (400 MHz, CDCl$_3$) δ 7.79 (br d, J=8.0 Hz, 2H), 7.36 (d, J=8.0 Hz, 2H), 5.13-5.06 (br m, 1H), 3.97-3.89 (m, 2H), 3.68-3.53 (br m, 2H), 3.31-3.20 (m, 2H), 2.46 (s, 3H), 2.01 (br dd, half of ABX pattern, J=14.3, 1.8 Hz, 1H), 1.93 (dd, half of ABX pattern, J=14.6, 6.5 Hz, 1H), 1.82-1.74 (m, 1H), 1.61-1.48 (m, 3H), 1.45 (s, 9H).

A sample of C31 was recrystallized from tert-butyl methyl ether/pentane and used to determine the absolute configuration via X-ray crystallography:

Single-Crystal X-Ray Structural Determination of C31

Single Crystal X-Ray Analysis

Data collection was performed on a Bruker D8 Quest diffractometer at room temperature. Data collection consisted of omega and phi scans.

The structure was solved by direct methods using SHELX software suite in the orthorhombic space group P2$_1$2$_1$2$_1$. The structure was subsequently refined by the full-matrix least squares method. All non-hydrogen atoms were found and refined using anisotropic displacement parameters.

The hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek).

Assuming the sample is enantiopure, the results indicate that the absolute structure has been correctly assigned. The method calculates that the probability that the structure is correctly assigned is 100.0. The Hooft parameter is reported as 0.04 with an esd of 0.002.

The final R-index was 6.0%. A final difference Fourier revealed no missing or misplaced electron density.

Pertinent crystal, data collection, and refinement information is summarized in Table 6.

Atomic coordinates, bond lengths, bond angles, and displacement parameters are listed in Tables 7-9.

Software and References

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE 6

Crystal data and structure refinement for C31.

| | |
|---|---|
| Empirical formula | $C_{20}H_{29}NO_6S$ |
| Formula weight | 411.51 |
| Temperature | 296(2) K |
| Wavelength | 1.54178 Å |
| Crystal system | Orthorhombic |
| Space group | $P2_12_12_1$ |
| Unit cell dimensions | a = 6.0597(12) Å   α = 90° |
| | b = 9.7363(17) Å   β = 90° |
| | c = 36.602(6) Å   γ = 90° |
| Volume | 2159.5(7) Å$^3$ |
| Z | 4 |
| Density (calculated) | 1.266 Mg/m$^3$ |
| Absorption coefficient | 1.627 mm$^{-1}$ |
| F(000) | 880 |
| Crystal size | 0.16 × 0.06 × 0.02 mm$^3$ |
| Theta range for data collection | 2.414 to 70.149° |
| Index ranges | −6 <= h <= 6, −11 <= k <= 11, −37 <= l <= 38 |
| Reflections collected | 19628 |
| Independent reflections | 3492 [$R_{int}$ = 0.0878] |
| Completeness to theta = 67.679° | 88.4% |
| Absorption correction | Empirical |
| Refinement method | Full-matrix least-squares on $F^2$ |
| Data/restraints/parameters | 3492/0/257 |
| Goodness-of-fit on $F^2$ | 1.089 |
| Final R indices [I > 2σ(I)] | R1 = 0.0596, wR2 = 0.1092 |
| R indices (all data) | R1 = 0.1215, wR2 = 0.1263 |
| Absolute structure parameter | 0.051(15) |
| Largest diff. peak and hole | 0.174 and −0.149 e. Å$^{-3}$ |

TABLE 7

Atomic coordinates (×10$^4$) and equivalent isotropic displacement parameters (Å$^2$ × 10$^3$) for C31.

| | x | y | z | U(eq) |
|---|---|---|---|---|
| S(1) | 5947(3) | 9247(2) | 4251(1) | 82(1) |
| N(1) | 7765(7) | 7309(4) | 2389(1) | 65(1) |
| O(1) | 7264(8) | 10289(4) | 4410(1) | 98(1) |
| O(2) | 3603(7) | 9332(5) | 4263(1) | 106(1) |
| O(3) | 6491(6) | 9126(4) | 3835(1) | 74(1) |

TABLE 7-continued

Atomic coordinates (×10$^4$) and equivalent isotropic displacement parameters (Å$^2$ × 10$^3$) for C31.

| | x | y | z | U(eq) |
|---|---|---|---|---|
| O(4) | 9650(6) | 7625(3) | 3283(1) | 80(1) |
| O(5) | 4826(7) | 7516(4) | 2018(1) | 95(1) |
| O(6) | 8242(5) | 8058(4) | 1823(1) | 67(1) |
| C(1) | 8816(11) | 7478(7) | 4584(1) | 79(2) |
| C(2) | 9399(12) | 6205(8) | 4717(1) | 88(2) |
| C(3) | 7981(15) | 5107(7) | 4702(2) | 98(2) |
| C(4) | 8699(18) | 3713(8) | 4844(2) | 159(4) |
| C(5) | 5973(15) | 5321(9) | 4549(2) | 111(2) |
| C(6) | 5312(12) | 6579(8) | 4415(2) | 92(2) |
| C(7) | 6761(9) | 7668(6) | 4427(1) | 70(2) |
| C(8) | 8759(10) | 9334(6) | 3703(1) | 72(2) |
| C(9) | 9928(13) | 8002(7) | 3642(2) | 103(2) |
| C(10) | 8621(8) | 8694(5) | 3072(1) | 56(1) |
| C(11) | 8632(10) | 9931(5) | 3328(2) | 74(2) |
| C(12) | 10002(8) | 8919(5) | 2733(1) | 61(2) |
| C(13) | 10002(9) | 7693(6) | 2482(1) | 67(2) |
| C(14) | 6421(10) | 6993(6) | 2707(1) | 76(2) |
| C(15) | 6345(9) | 8214(5) | 2959(1) | 65(2) |
| C(16) | 6789(10) | 7629(5) | 2073(2) | 61(1) |
| C(17) | 7526(9) | 8625(6) | 1472(2) | 66(2) |
| C(18) | 6298(12) | 7567(6) | 1249(2) | 95(2) |
| C(19) | 9684(11) | 9020(7) | 1295(2) | 99(2) |
| C(20) | 6135(12) | 9903(6) | 1540(2) | 93(2) |

U(eq) is defined as one-third of the trace of the orthogonalized $U^{ij}$ tensor.

TABLE 8

Bond lengths [Å] and angles [°] for C31.

| | |
|---|---|
| S(1)—O(1) | 1.416(4) |
| S(1)—O(2) | 1.424(4) |
| S(1)—O(3) | 1.562(4) |
| S(1)—C(7) | 1.738(6) |
| N(1)—C(16) | 1.336(6) |
| N(1)—C(13) | 1.447(7) |
| N(1)—C(14) | 1.453(6) |
| O(3)—C(8) | 1.471(7) |
| O(4)—C(9) | 1.372(6) |
| O(4)—C(10) | 1.438(5) |
| O(5)—C(16) | 1.212(6) |
| O(6)—C(16) | 1.337(6) |
| O(6)—C(17) | 1.463(6) |
| C(1)—C(2) | 1.378(8) |
| C(1)—C(7) | 1.384(8) |
| C(1)—H(1) | 0.9300 |
| C(2)—C(3) | 1.372(9) |
| C(2)—H(2) | 0.9300 |
| C(3)—C(5) | 1.356(10) |
| C(3)—C(4) | 1.517(9) |
| C(4)—H(4A) | 0.9600 |
| C(4)—H(4B) | 0.9600 |
| C(4)—H(4C) | 0.9600 |
| C(5)—C(6) | 1.379(9) |
| C(5)—H(5) | 0.9300 |
| C(6)—C(7) | 1.378(8) |
| C(6)—H(6) | 0.9300 |
| C(8)—C(11) | 1.493(7) |
| C(8)—C(9) | 1.496(7) |
| C(8)—H(8) | 0.9800 |
| C(9)—H(9A) | 0.9700 |
| C(9)—H(9B) | 0.9700 |
| C(10)—C(12) | 1.513(6) |
| C(10)—C(15) | 1.514(7) |
| C(10)—C(11) | 1.526(6) |
| C(11)—H(11A) | 0.9700 |
| C(11)—H(11B) | 0.9700 |
| C(12)—C(13) | 1.506(7) |
| C(12)—H(12A) | 0.9700 |

TABLE 8-continued

Bond lengths [Å] and angles [°] for C31.

| Bond | Value |
|---|---|
| C(12)—H(12B) | 0.9700 |
| C(13)—H(13A) | 0.9700 |
| C(13)—H(13B) | 0.9700 |
| C(14)—C(15) | 1.507(7) |
| C(14)—H(14A) | 0.9700 |
| C(14)—H(14B) | 0.9700 |
| C(15)—H(15A) | 0.9700 |
| C(15)—H(15B) | 0.9700 |
| C(17)—C(19) | 1.510(7) |
| C(17)—C(18) | 1.511(7) |
| C(17)—C(20) | 1.523(7) |
| C(18)—H(18A) | 0.9600 |
| C(18)—H(18B) | 0.9600 |
| C(18)—H(18C) | 0.9600 |
| C(19)—H(19A) | 0.9600 |
| C(19)—H(19B) | 0.9600 |
| C(19)—H(19C) | 0.9600 |
| C(20)—H(20A) | 0.9600 |
| C(20)—H(20B) | 0.9600 |
| C(20)—H(20C) | 0.9600 |
| O(1)—S(1)—O(2) | 120.5(3) |
| O(1)—S(1)—O(3) | 109.6(2) |
| O(2)—S(1)—O(3) | 104.1(2) |
| O(1)—S(1)—C(7) | 108.8(3) |
| O(2)—S(1)—C(7) | 108.9(3) |
| O(3)—S(1)—C(7) | 103.5(2) |
| C(16)—N(1)—C(13) | 123.9(5) |
| C(16)—N(1)—C(14) | 119.6(5) |
| C(13)—N(1)—C(14) | 113.1(4) |
| C(8)—O(3)—S(1) | 120.5(3) |
| C(9)—O(4)—C(10) | 111.9(4) |
| C(16)—O(6)—C(17) | 121.6(4) |
| C(2)—C(1)—C(7) | 119.8(6) |
| C(2)—C(1)—H(1) | 120.1 |
| C(7)—C(1)—H(1) | 120.1 |
| C(3)—C(2)—C(1) | 121.7(6) |
| C(3)—C(2)—H(2) | 119.1 |
| C(1)—C(2)—H(2) | 119.1 |
| C(5)—C(3)—C(2) | 117.3(7) |
| C(5)—C(3)—C(4) | 122.4(7) |
| C(2)—C(3)—C(4) | 120.2(7) |
| C(3)—C(4)—H(4A) | 109.5 |
| C(3)—C(4)—H(4B) | 109.5 |
| H(4A)—C(4)—H(4B) | 109.5 |
| C(3)—C(4)—H(4C) | 109.5 |
| H(4A)—C(4)—H(4C) | 109.5 |
| H(4B)—C(4)—H(4C) | 109.5 |
| C(3)—C(5)—C(6) | 122.9(7) |
| C(3)—C(5)—H(5) | 118.5 |
| C(6)—C(5)—H(5) | 118.5 |
| C(7)—C(6)—C(5) | 119.2(6) |
| C(7)—C(6)—H(6) | 120.4 |
| C(5)—C(6)—H(6) | 120.4 |
| C(6)—C(7)—C(1) | 119.0(6) |
| C(6)—C(7)—S(1) | 119.2(5) |
| C(1)—C(7)—S(1) | 121.8(5) |
| O(3)—C(8)—C(11) | 108.0(5) |
| O(3)—C(8)—C(9) | 111.9(5) |
| C(11)—C(8)—C(9) | 102.9(5) |
| O(3)—C(8)—H(8) | 111.3 |
| C(11)—C(8)—H(8) | 111.3 |
| C(9)—C(8)—H(8) | 111.3 |
| O(4)—C(9)—C(8) | 108.5(5) |
| O(4)—C(9)—H(9A) | 110.0 |
| C(8)—C(9)—H(9A) | 110.0 |
| O(4)—C(9)—H(9B) | 110.0 |
| C(8)—C(9)—H(9B) | 110.0 |
| H(9A)—C(9)—H(9B) | 108.4 |
| O(4)—C(10)—C(12) | 107.8(4) |
| O(4)—C(10)—C(15) | 108.5(4) |
| C(12)—C(10)—C(15) | 109.0(4) |
| O(4)—C(10)—C(11) | 103.8(4) |
| C(12)—C(10)—C(11) | 112.8(4) |
| C(15)—C(10)—C(11) | 114.5(4) |
| C(8)—C(11)—C(10) | 105.0(4) |
| C(8)—C(11)—H(11A) | 110.8 |
| C(10)—C(11)—H(11A) | 110.8 |
| C(8)—C(11)—H(11B) | 110.8 |
| C(10)—C(11)—H(11B) | 110.8 |
| H(11A)—C(11)—H(11B) | 108.8 |
| C(13)—C(12)—C(10) | 112.7(4) |
| C(13)—C(12)—H(12A) | 109.0 |
| C(10)—C(12)—H(12A) | 109.0 |
| C(13)—C(12)—H(12B) | 109.0 |
| C(10)—C(12)—H(12B) | 109.0 |
| H(12A)—C(12)—H(12B) | 107.8 |
| N(1)—C(13)—C(12) | 110.4(4) |
| N(1)—C(13)—H(13A) | 109.6 |
| C(12)—C(13)—H(13A) | 109.6 |
| N(1)—C(13)—H(13B) | 109.6 |
| C(12)—C(13)—H(13B) | 109.6 |
| H(13A)—C(13)—H(13B) | 108.1 |
| N(1)—C(14)—C(15) | 110.0(4) |
| N(1)—C(14)—H(14A) | 109.7 |
| C(15)—C(14)—H(14A) | 109.7 |
| N(1)—C(14)—H(14B) | 109.7 |
| C(15)—C(14)—H(14B) | 109.7 |
| H(14A)—C(14)—H(14B) | 108.2 |
| C(14)—C(15)—C(10) | 112.5(4) |
| C(14)—C(15)—H(15A) | 109.1 |
| C(10)—C(15)—H(15A) | 109.1 |
| C(14)—C(15)—H(15B) | 109.1 |
| C(10)—C(15)—H(15B) | 109.1 |
| H(15A)—C(15)—H(15B) | 107.8 |
| O(5)—C(16)—O(6) | 124.1(5) |
| O(5)—C(16)—N(1) | 123.9(5) |
| O(6)—C(16)—N(1) | 112.0(5) |
| O(6)—C(17)—C(19) | 102.6(4) |
| O(6)—C(17)—C(18) | 111.3(4) |
| C(19)—C(17)—C(18) | 111.5(5) |
| O(6)—C(17)—C(20) | 109.3(4) |
| C(19)—C(17)—C(20) | 110.0(5) |
| C(18)—C(17)—C(20) | 111.8(5) |
| C(17)—C(18)—H(18A) | 109.5 |
| C(17)—C(18)—H(18B) | 109.5 |
| H(18A)—C(18)—H(18B) | 109.5 |
| C(17)—C(18)—H(18C) | 109.5 |
| H(18A)—C(18)—H(18C) | 109.5 |
| H(18B)—C(18)—H(18C) | 109.5 |
| C(17)—C(19)—H(19A) | 109.5 |
| C(17)—C(19)—H(19B) | 109.5 |
| H(19A)—C(19)—H(19B) | 109.5 |
| C(17)—C(19)—H(19C) | 109.5 |
| H(19A)—C(19)—H(19C) | 109.5 |
| H(19B)—C(19)—H(19C) | 109.5 |
| C(17)—C(20)—H(20A) | 109.5 |
| C(17)—C(20)—H(20B) | 109.5 |
| H(20A)—C(20)—H(20B) | 109.5 |
| C(17)—C(20)—H(20C) | 109.5 |
| H(20A)—C(20)—H(20C) | 109.5 |
| H(20B)—C(20)—H(20C) | 109.5 |

Symmetry transformations used to generate equivalent atoms.

TABLE 9

Anisotropic displacement parameters (Å$^2$ × 10$^3$) for C31.
The anisotropic displacement factor exponent takes the form:
$-2\pi^2[h^2 a^{*2} U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| S(1) | 86(1) | 94(1) | 66(1) | −7(1) | 4(1) | 3(1) |
| N(1) | 48(3) | 88(3) | 59(3) | 3(3) | −3(2) | −14(2) |
| O(1) | 117(4) | 94(3) | 84(3) | −29(2) | 3(2) | −13(3) |
| O(2) | 74(3) | 141(4) | 105(3) | 13(3) | 12(2) | 20(3) |

TABLE 9-continued

Anisotropic displacement parameters (Å² × 10³) for C31.
The anisotropic displacement factor exponent takes the form:
$-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| O(3)  | 78(3)   | 83(3)  | 63(3)  | 2(2)  | −3(2)  | −4(2)  |
| O(4)  | 113(3)  | 60(2)  | 66(3)  | 2(2)  | −17(2) | 26(2)  |
| O(5)  | 52(3)   | 150(4) | 83(3)  | −3(2) | −5(2)  | −27(3) |
| O(6)  | 50(2)   | 87(2)  | 63(3)  | 7(2)  | 7(2)   | −2(2)  |
| C(1)  | 81(4)   | 98(5)  | 56(4)  | −1(3) | −8(3)  | −19(4) |
| C(2)  | 92(5)   | 112(6) | 61(4)  | 6(4)  | −22(3) | 1(5)   |
| C(3)  | 139(8)  | 89(5)  | 66(5)  | 0(4)  | −19(4) | −22(5) |
| C(4)  | 229(11) | 99(6)  | 148(7) | 36(5) | −64(7) | −15(6) |
| C(5)  | 122(7)  | 109(6) | 102(5) | −2(4) | −29(5) | −43(5) |
| C(6)  | 85(5)   | 103(5) | 90(5)  | −6(4) | −18(3) | −18(4) |
| C(7)  | 68(4)   | 94(4)  | 48(3)  | −9(3) | −4(3)  | −9(3)  |
| C(8)  | 72(4)   | 75(4)  | 69(4)  | −9(3) | −4(3)  | −7(4)  |
| C(9)  | 125(6)  | 116(5) | 69(5)  | −6(4) | −17(4) | 45(5)  |
| C(10) | 57(4)   | 53(3)  | 57(3)  | 8(3)  | 1(2)   | 7(3)   |
| C(11) | 94(5)   | 47(3)  | 80(5)  | −7(3) | 14(3)  | 0(3)   |
| C(12) | 44(3)   | 65(3)  | 75(4)  | 4(3)  | 1(2)   | −3(3)  |
| C(13) | 47(3)   | 85(4)  | 68(4)  | −4(3) | 1(2)   | 4(3)   |
| C(14) | 69(4)   | 94(4)  | 65(4)  | 1(3)  | 10(3)  | −27(3) |
| C(15) | 52(4)   | 80(4)  | 64(4)  | 11(3) | 12(3)  | 0(3)   |
| C(16) | 50(4)   | 66(4)  | 67(4)  | −6(3) | 4(3)   | −9(3)  |
| C(17) | 67(4)   | 71(4)  | 59(4)  | 4(3)  | 3(3)   | 0(3)   |
| C(18) | 117(6)  | 88(4)  | 82(5)  | −13(3)| −10(4) | −3(4)  |
| C(19) | 89(5)   | 110(5) | 98(5)  | 15(4) | 33(4)  | −4(4)  |
| C(20) | 97(5)   | 76(4)  | 105(5) | −1(3) | −2(4)  | 22(4)  |

Step 3. Synthesis of tert-butyl (3S)-3-hydroxy-1-oxa-8-azaspiro[4.5]decane-8-carboxylate (C32) and tert-butyl (3R)-3-hydroxy-1-oxa-8-azaspiro[4.5]decane-8-carboxylate (C33)

Sodium borohydride (445 mg, 11.8 mmol) was added to a 0° C. solution of tert-butyl 3-oxo-1-oxa-8-azaspiro[4.5]decane-8-carboxylate (1.50 g, 5.88 mmol) in methanol (59 mL) and the reaction mixture was stirred at 23° C. for 2 hours. After removal of solvent in vacuo, the residue was partitioned between ethyl acetate and water. The aqueous layer was extracted with ethyl acetate, and the combined organic layers were dried over magnesium sulfate, filtered, and concentrated under reduced pressure to provide a mixture of C32 and C33 as a colorless oil. Yield of racemic product: 1.45 g, 5.63 mmol, 96%. GCMS m/z 257.1 [M⁺]. ¹H NMR (400 MHz, CDCl₃) δ 4.54-4.48 (br m, 1H), 3.93 (dd, half of ABX pattern, J=10.2, 4.3 Hz, 1H), 3.85-3.79 (m, 1H), 3.67-3.53 (br m, 2H), 3.40-3.28 (m, 2H), 1.97 (dd, half of ABX pattern, J=13.7, 6.2 Hz, 1H), 1.89-1.48 (m, 6H, assumed; partially obscured by water peak), 1.46 (s, 9H).

A portion of this racemic material (1.30 g, 5.05 mmol) was separated into its component enantiomers via supercritical fluid chromatography [Column: Phenomenex Lux Amylose-1, 5 µm; Mobile phase: 85:15 carbon dioxide/(methanol containing 0.2% ammonium hydroxide)]. The first-eluting product, obtained as a gum that exhibited a negative (−) rotation, was designated as C32. Yield: 650 mg, 2.53 mmol, 50% for the separation. The second-eluting product, obtained as a solid that exhibited a positive (+) rotation, was designated as C33. Yield: 620 mg, 2.41 mmol, 48% for the separation. The indicated absolute stereochemistries of C32 and C33 were assigned on the basis of conversion of C32 to C30 (see step 4).

Step 4. Alternate synthesis of tert-butyl (3S)-3-{[(4-methylphenyl)sulfonyl]oxy}-1-oxa-8-azaspiro[4.5]decane-8-carboxylate (C30)

p-Toluenesulfonyl chloride (244 mg, 1.28 mmol) was added to a solution of C32 (300 mg, 1.17 mmol) in dichloromethane (12 mL). 4-(Dimethylamino)pyridine (285 mg, 2.33 mmol) was then added, and the reaction mixture was stirred overnight. After addition of water, the mixture was extracted with dichloromethane, and the combined organic layers were concentrated in vacuo and purified via silica gel chromatography (Gradient: 10% to 55% ethyl acetate in heptane). The product was obtained as a gum that exhibited a positive (+) rotation. Yield: 426 mg, 1.04 mmol, 89%. LCMS m/z 412.5 [M+H]⁺. ¹H NMR (400 MHz, CDCl₃) δ 7.76 (d, J=8.2 Hz, 2H), 7.34 (d, J=7.8 Hz, 2H), 5.10-5.03 (m, 1H), 3.94-3.86 (m, 2H), 3.62-3.53 (m, 2H), 3.27-3.17 (m, 2H), 2.43 (s, 3H), 1.98 (dd, half of ABX pattern, J=14.4, 2.0 Hz, 1H), 1.90 (dd, half of ABX pattern, J=14.6, 6.4 Hz, 1H), 1.79-1.71 (m, 1H), 1.59-1.45 (m, 3H), 1.42 (s, 9H). This sample, derived from C32, was established as possessing the indicated absolute stereochemistry via comparison of its optical rotation with that of the C30 sample synthesized in step 2 above.

Step 5. Synthesis of tert-butyl (3R)-3-(4-fluoro-1H-pyrazol-1-yl)-1-oxa-8-azaspiro[4.5]decane-8-carboxylate (C34)

To a solution of C30 (222 mg, 0.539 mmol) in N,N-dimethylformamide (3 mL) were added cesium carbonate (528 mg, 1.62 mmol) and 4-fluoro-1H-pyrazole (69.6 mg, 0.809 mmol). The reaction mixture was stirred overnight at room temperature, and then at 50° C. for 3 hours, whereupon it was diluted with water and extracted with ethyl acetate (3×50 mL). The combined organic layers were dried over magnesium sulfate, filtered, concentrated in vacuo, and purified via chromatography on silica gel (Gradient: 10% to 65% ethyl acetate in heptane) to provide the product as a colorless oil. Yield: 148 mg, 0.455 mmol, 84%. LCMS m/z 326.4 [M+H]⁺. ¹H NMR (400 MHz, CDCl₃) δ 7.37 (d, J=5.1 Hz, 1H), 7.32 (d, J=4.3 Hz, 1H), 4.88-4.80 (m, 1H), 4.15 (dd, half of ABX pattern, J=10.0, 6.0 Hz, 1H), 4.10 (dd, half of ABX pattern, J=10.2, 4.7 Hz, 1H), 3.68-3.56 (br m, 2H), 3.37-3.26 (m, 2H), 2.28 (dd, half of ABX pattern, J=13.7, 8.6 Hz, 1H), 2.17 (dd, half of ABX pattern, J=13.5, 5.3 Hz, 1H), 1.80-1.59 (m, 3H), 1.59-1.49 (m, 1H), 1.44 (s, 9H).

Step 6. Synthesis of (3R)-3-(4-fluoro-1H-pyrazol-1-yl)-1-oxa-8-azaspiro[4.5]decane, Trifluoroacetate Salt (C35)

Trifluoroacetic acid (0.71 mL) was added to a 0° C. solution of C34 (200 mg, 0.615 mmol) in dichloromethane (6.2 mL), and the reaction mixture was stirred at 0° C. for 35 minutes. It was then concentrated in vacuo, and azeotroped repeatedly with heptane (3×10 mL) to afford the product as an oil. This material was taken directly into the following step. $^1$H NMR (400 MHz, CDCl$_3$), derived from a reaction using C34 that was carried out on similar scale: δ 8.2-7.9 (br s, 2H), 7.48 (br d, J=3.9 Hz, 1H), 7.45 (br d, J=4.7 Hz, 1H), 5.06-4.98 (m, 1H), 4.23 (dd, half of ABX pattern, J=10.6, 3.9 Hz, 1H), 4.19 (dd, half of ABX pattern, J=10.6, 5.9 Hz, 1H), 3.47-3.30 (br m, 4H), 2.44 (dd, half of ABX pattern, J=14.1, 8.2 Hz, 1H), 2.27 (dd, half of ABX pattern, J=14.1, 4.7 Hz, 1H), 2.12-1.93 (m, 4H).

Step 7. Synthesis of 1,1,1,3,3,3-hexafluoropropan-2-yl (3R)-3-(4-fluoro-1H-pyrazol-1-yl)-1-oxa-8-azaspiro[4.5]decane-8-carboxylate (12)

A solution of C35 (from the previous step; ≤0.615 mmol) and triethylamine (0.62 g, 6.1 mmol) in acetonitrile (10 mL) was stirred for 15 minutes at 0° C. Addition of C12 (reaction solution in acetonitrile, containing 0.80 mmol) to the cold solution was effected slowly, over 20 minutes, and stirring was continued at 0° C. for 30 minutes. The reaction mixture was then warmed to room temperature and allowed to stir overnight. After removal of volatiles in vacuo, the residue was dissolved in dichloromethane and washed sequentially with 1 M hydrochloric acid, saturated aqueous ammonium chloride solution, and saturated aqueous sodium chloride solution. The organic layer was then dried, filtered, and concentrated under reduced pressure. Silica gel chromatography (Gradient: 0% to 60% ethyl acetate in heptane), followed by reversed-phase HPLC (Waters Sunfire C18, 5 μm; Mobile phase A: 0.05% trifluoroacetic acid in water (v/v); Mobile phase B: 0.05% trifluoroacetic acid in acetonitrile (v/v); Gradient: 50% to 100% B) afforded the product. Yield: 47.4 mg, 0.113 mmol, 18% over two steps. LCMS m/z 420.5 [M+H]$^+$. $^1$H NMR (400 MHz, CDCl$_3$) δ 7.38 (d, J=4.7 Hz, 1H), 7.36 (d, J=4.3 Hz, 1H), 5.82-5.70 (m, 1H), 4.91-4.82 (m, 1H), 4.23-4.12 (m, 2H), 3.92-3.80 (m, 2H), 3.48-3.33 (m, 2H), 2.31 (dd, half of ABX pattern, J=13.7, 8.2 Hz, 1H), 2.30-2.22 (m, 1H), 1.93-1.84 (br m, 1H), 1.83-1.54 (m, 3H).

Example 13

1-({[(3R)-3-(4-Fluoro-1H-pyrazol-1-yl)-1-oxa-8-azaspiro[4.5]dec-8-yl]carbonyl}oxy)pyrrolidine-2,5-dione (13)

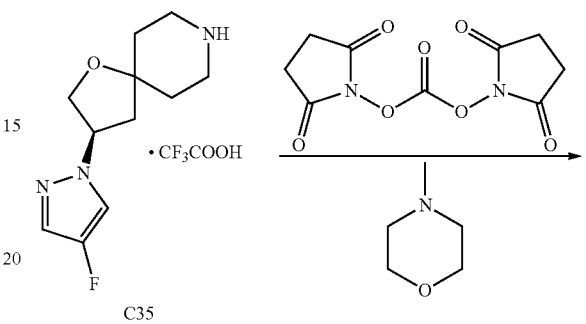

To a stirred solution of C35 (71 mg, 0.21 mmol) in dichloromethane (6 mL) were added N,N'-disuccinimidyl carbonate (84.8 mg, 0.331 mmol) and 4-methylmorpholine (0.395 mL, 3.59 mmol). The reaction mixture was stirred at room temperature overnight, whereupon water was added, and the mixture was extracted with dichloromethane (3×20 mL). The combined organic layers were washed with hydrochloric acid (1 M; 20 mL), dried over magnesium sulfate, filtered, and concentrated in vacuo. Silica gel chromatography (Gradient: 0% to 75% ethyl acetate in heptane) afforded the product as a solid. Yield: 53 mg, 0.145 mmol, 69%. LCMS m/z 367.4 [M+H]$^+$. $^1$H NMR (400 MHz, CDCl$_3$) δ 7.37 (d, J=4.7 Hz, 1H), 7.34 (d, J=4.3 Hz, 1H), 4.90-4.81 (m, 1H), 4.17 (dd, half of ABX pattern, J=10.0, 6.0 Hz, 1H), 4.14 (dd, half of ABX pattern, J=10.2, 5.1 Hz, 1H), 3.98-3.77 (m, 2H), 3.55-3.30 (m, 2H), 2.81 (s, 4H), 2.31 (dd, half of ABX pattern, J=13.7, 8.2 Hz, 1H), 2.24 (dd, half of ABX pattern, J=13.7, 5.1 Hz, 1H), 1.93-1.62 (m, 4H).

Example 14
1,1,1,3,3,3-Hexafluoropropan-2-yl 2-{[6-(difluoromethyl)pyridin-3-yl]oxy}-7-azaspiro[3.5]nonane-7-carboxylate (14)
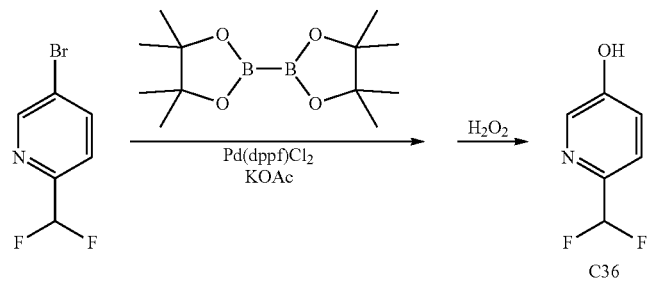
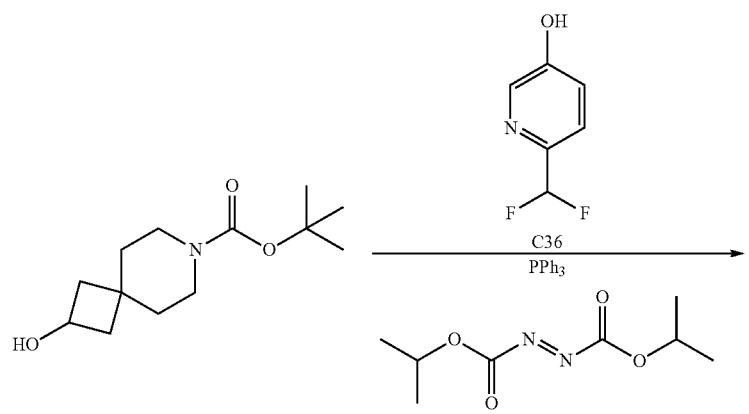
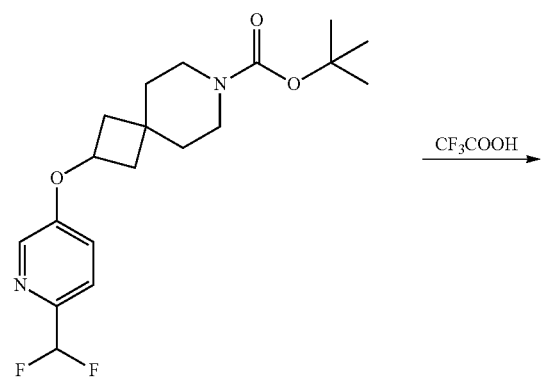

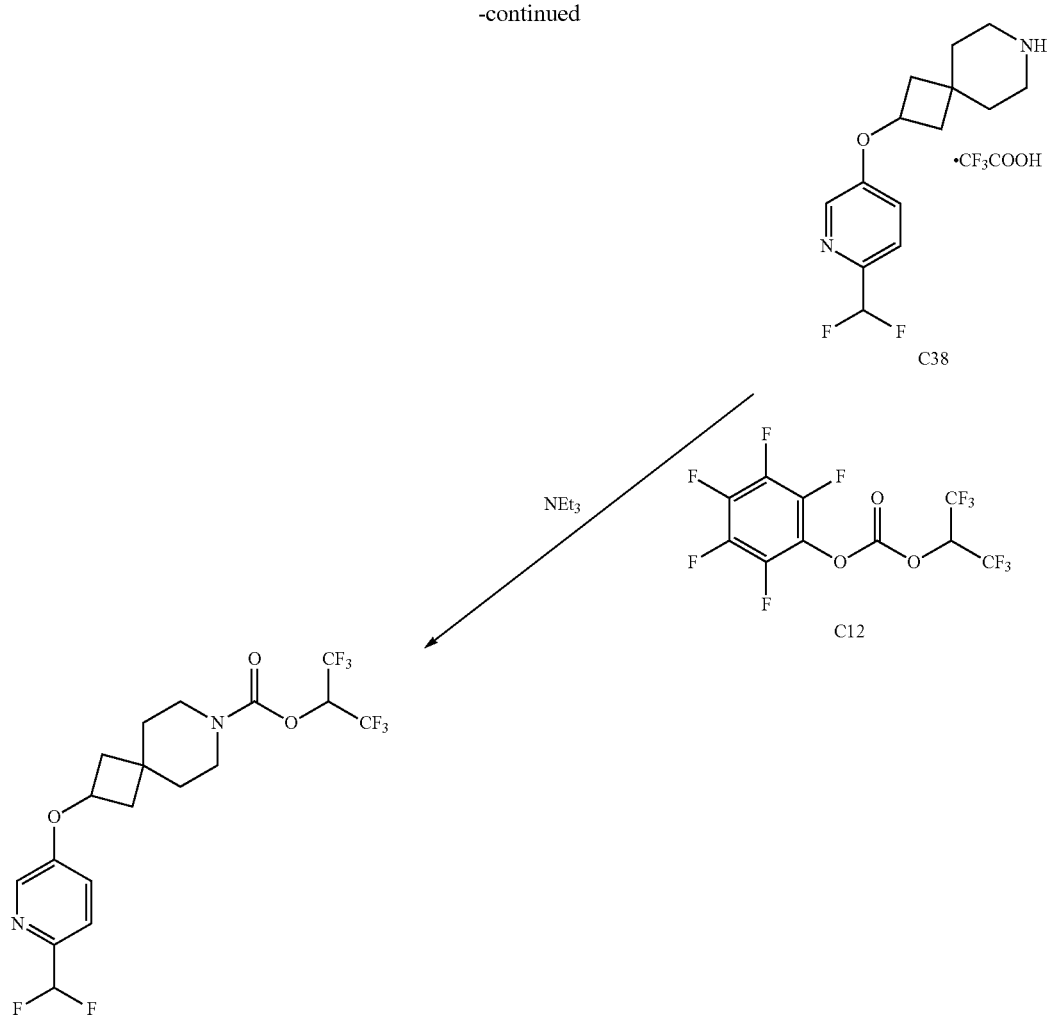

Step 1. Synthesis of 6-(difluoromethyl)pyridin-3-ol (C36)

4,4,4',4',5,5,5',5'-Octamethyl-2,2'-bi-1,3,2-dioxaborolane (537 mg, 2.11 mmol), [1,1'-bis(diphenylphosphino)ferrocene]dichloropalladium(II) (141 mg, 0.193 mmol), and potassium acetate (377 mg, 3.84 mmol) were added to a 30° C. solution of 5-bromo-2-(difluoromethyl)pyridine (400 mg, 1.92 mmol) in 1,4-dioxane (5 mL). After the reaction mixture had been degassed with nitrogen for 5 minutes, it was stirred for 18 hours at 115° C., whereupon it was filtered. Concentration of the filtrate provided a black solid (1.17 g), which was divided into two portions for addition of the next reagent. One portion of this material (870 mg, 1.43 mmol) was dissolved in a mixture of tetrahydrofuran (10 mL) and water (10 mL) and treated with hydrogen peroxide (30% aqueous solution; 487 mg, 4.29 mmol) at 28° C. The reaction mixture was stirred for 15 hours at 28° C., whereupon it was combined with the reaction mixture from the second portion, and the oxidant was quenched via addition of saturated aqueous sodium sulfite solution (5 mL) (until the resulting mixture tested negative with potassium iodide-starch test paper). The resulting mixture was extracted with ethyl acetate (2×20 mL), and the combined organic layers were dried over sodium sulfate, filtered, and concentrated in vacuo. Silica gel chromatography (Gradient: 0% to 25% ethyl acetate in petroleum ether) provided the product as a white solid. Yield: 148 mg, 1.02 mmol, 53%. LCMS m/z 145.9 [M+H]$^+$. $^1$H NMR (400 MHz, CDCl$_3$) δ 8.28 (d, J=2.5 Hz, 1H), 7.56 (d, J=8.5 Hz, 1H), 7.30 (dd, J=8.5, 2.5 Hz, 1H), 6.62 (t, J$_{HF}$=55.7 Hz, 1H).

Step 2. Synthesis of tert-butyl 2-{[6-(difluoromethyl)pyridin-3-yl]oxy}-7-azaspiro[3.5]nonane-7-carboxylate (C37)

To a 0° C. mixture of tert-butyl 2-hydroxy-7-azaspiro[3.5]nonane-7-carboxylate (50 mg, 0.21 mmol), C36 (39.1 mg, 0.269 mmol), and triphenylphosphine (109 mg, 0.416 mmol) in tetrahydrofuran (1.5 mL) was added diisopropyl azodicarboxylate (83.8 mg, 0.414 mmol) in a drop-wise manner, and the reaction mixture was stirred at 28° C. for 15 hours. It was then directly purified via preparative thin-layer chromatography on silica gel (Eluent: 3:1 petroleum ether/ethyl acetate), providing the product as a yellow gum (100 mg), which by $^1$H NMR analysis was contaminated with material derived from diisopropyl azodicarboxylate. $^1$H NMR (400 MHz, CDCl$_3$), product peaks only: δ 8.22 (d, J=2.5 Hz, 1H), 7.56 (d, J=8.5 Hz, 1H), 7.18 (dd, J=8.5, 3.0 Hz, 1H), 6.61 (t, J$_{HF}$=55.7 Hz, 1H), 4.80-4.72 (m, 1H), 3.42-3.36 (m 2H), 3.36-3.30 (m, 2H), 2.49-2.41 (m, 2H), 2.03-1.95 (m, 2H), 1.65-1.56 (m, 4H, assumed; partially obscured by water peak), 1.46 (s, 9H).

Step 3. Synthesis of 2-{[6-(difluoromethyl)pyridin-3-yl]oxy}-7-azaspiro[3.5]nonane, Trifluoroacetate Salt (C38)

Trifluoroacetic acid (1 mL) was added to a 0° C. solution of C37 (250 mg, 0.679 mmol) in dichloromethane (4 mL). The reaction mixture was stirred at 10° C. for 1 hour, whereupon it was concentrated under reduced pressure to afford the product as a yellow oil. A portion of this material was taken directly to the following step. LCMS m/z 268.9 [M+H]+.

Step 4. Synthesis of 1,1,1,3,3,3-hexafluoropropan-2-yl 2-{[6-(difluoromethyl)pyridin-3-yl]oxy}-7-azaspiro[3.5]nonane-7-carboxylate (14)

Triethylamine (0.170 mL, 1.22 mmol) was slowly added to a 0° C. solution of C38 (from the previous step; ≤0.408 mmol) in acetonitrile (3 mL), and the mixture was stirred for 30 minutes at 0° C. A solution of C12 (reaction solution in acetonitrile, containing 1.07 mmol) was added under ice-cooling, and the reaction mixture was allowed to stir at 10° C. for 18 hours. After solvent had been removed in vacuo, the residue was purified via reversed-phase HPLC (Column: Agela Durashell C18, 5 μm; Mobile phase A: 0.225% formic acid in water; Mobile phase B: acetonitrile; Gradient: 55% to 75% B) to provide the product as a white solid. Yield: 74.9 mg, 0.162 mmol, 40% over two steps. LCMS m/z 463.2 [M+H]+. $^1$H NMR (400 MHz, CDCl$_3$) 8.22 (d, J=2.5 Hz, 1H), 7.56 (d, J=8.5 Hz, 1H), 7.18 (dd, J=8.8, 2.8 Hz, 1H), 6.62 (t, J$_{HF}$=55.7 Hz, 1H), 5.76 (septet, J=6.2 Hz, 1H), 4.83-4.74 (m, 1H), 3.56-3.50 (m, 2H), 3.50-3.44 (m, 2H), 2.54-2.44 (m, 2H), 2.08-2.00 (m, 2H), 1.76-1.64 (m, 4H).

TABLE 10

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]+ or HPLC retention time; Mass spectrum m/z [M + H]+ (unless otherwise indicated) |
|---|---|---|---|
| 15 | Example 2[1]; P1 | 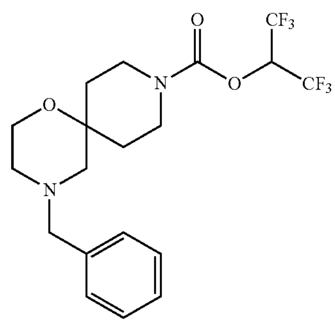 [SMILES: O=C(OC(C(F)(F)F)C(F)(F)F)N1CCC2(CC1)CN(Cc1ccccc1)CCO2] | 7.36-7.23 (m, 5H), 5.75 (septet, J = 6.3 Hz, 1H), 3.88-3.77 (m, 2H), 3.77-3.72 (m, 2H), 3.46 (s, 2H), 3.36-3.21 (m, 2H), 2.49-2.42 (m, 2H), 2.22 (s, 2H), 2.15-2.01 (m, 2H), 1.49-1.34 (m, 2H); 440.9 |
| 16 | Example 3; P1 | 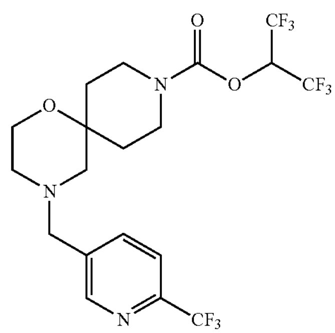 [SMILES: O=C(OC(C(F)(F)F)C(F)(F)F)N1CCC2(CC1)CN(Cc1ccc(C(F)(F)F)nc1)CCO2] | 3.18 minutes[2]; 510 |
| 17 | Example 3; P1 | 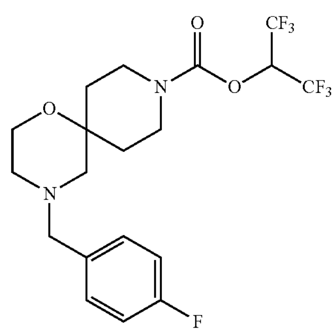 [SMILES: O=C(OC(C(F)(F)F)C(F)(F)F)N1CCC2(CC1)CN(Cc1ccc(F)cc1)CCO2] | 2.77 minutes[3]; 459 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 18 | Example 3; P1 | 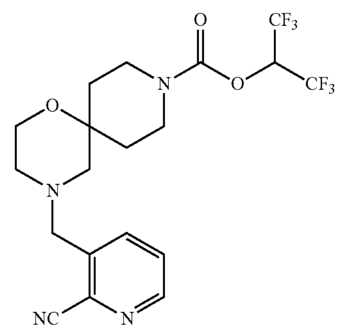 [SMILES: N#Cc1ncccc1CN1CCOC2(CCN(C(=O)OC(C(F)(F)F)C(F)(F)F)CC2)C1] | 3.20 minutes$^3$; 467 |
| 19 | Example 3; P1 | 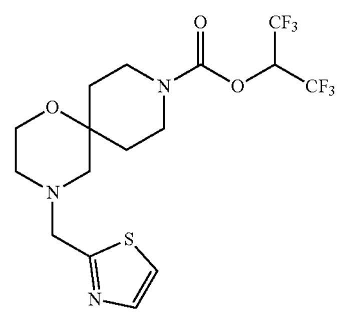 [SMILES: O=C(OC(C(F)(F)F)C(F)(F)F)N1CCC2(CC1)CN(Cc1nccs1)CCO2] | 3.04 minutes$^2$; 448 |
| 20 | Example 3; P1 | 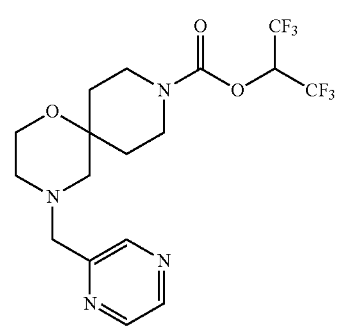 [SMILES: O=C(OC(C(F)(F)F)C(F)(F)F)N1CCC2(CC1)CN(Cc1cnccn1)CCO2] | 3.00 minutes$^4$; 443 |
| 21 | Example 3; P1 | 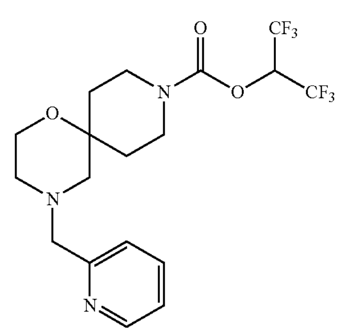 [SMILES: O=C(OC(C(F)(F)F)C(F)(F)F)N1CCC2(CC1)CN(Cc1ccccn1)CCO2] | 2.80 minutes$^2$; 442 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 22 | Example 4[5]; P1 | 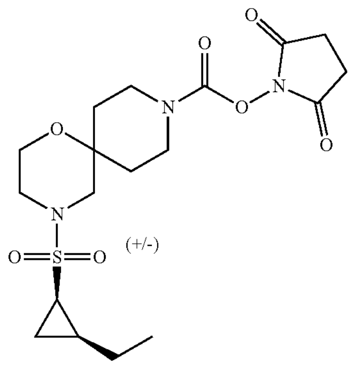 [SMILES: CC[C@H]1C[C@H]1S(=O)(=O)N1CCOC2(CCN(C(=O)ON3C(=O)CCC3=O)CC2)C1] | 2.74 minutes[2]; 430 |
| 23 | Example 3; P1 | 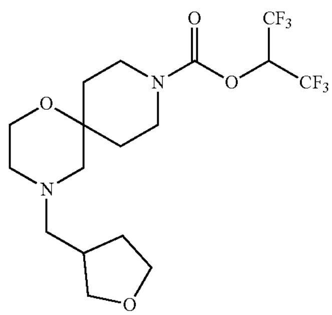 [SMILES: O=C(OC(C(F)(F)F)C(F)(F)F)N1CCC2(CC1)CN(CC1CCOC1)CCO2] | 2.67 minutes[2]; 435 |
| 24 | Example 3; P1 | 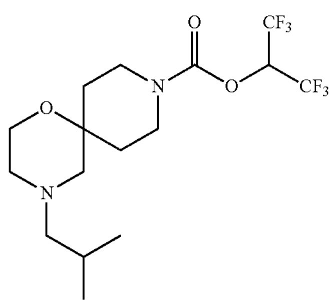 [SMILES: CC(C)CN1CCOC2(CCN(C(=O)OC(C(F)(F)F)C(F)(F)F)CC2)C1] | 2.75 minutes[2]; 407 |
| 25 | Example 15[6]; P1 | 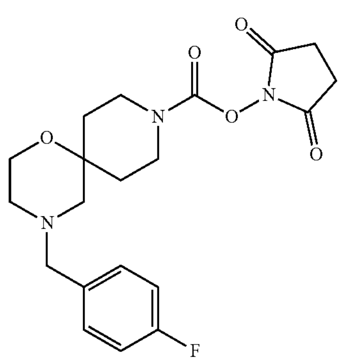 [SMILES: O=C(ON1C(=O)CCC1=O)N1CCC2(CC1)CN(Cc1ccc(F)cc1)CCO2] | 7.31-7.23 (m, 2H, assumed; partially obscured by solvent peak), 7.01 (dd, J = 8.3, 8.1 Hz, 2H), 3.96-3.87 (m, 1H), 3.86-3.77 (m, 1H), 3.77-3.70 (m, 2H), 3.43-3.33 (m, 1H), 3.41 (s, 2H), 3.31-3.21 (m, 1H), 2.82 (s, 4H), 2.46-2.39 (m, 2H), 2.22 (s, 2H), 2.15-2.02 (m, 2H), 1.6-1.40 (m, 2H, assumed; partially obscured by water peak); 406.1 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 26 | Example 7[7]; P1 | 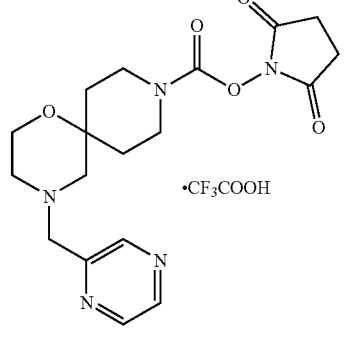 | $^1$H NMR (400 MHz, CD$_3$OD) δ 8.74 (d, J = 1.3 Hz, 1H), 8.72-8.69 (m, 1H), 8.67 (d, J = 2.6 Hz, 1H), 4.43 (s, 2H), 4.04-3.94 (m, 3H), 3.92-3.83 (m, 1H), 3.46-3.22 (m, 4H, assumed; partially obscured by solvent peak), 3.16-3.04 (m, 2H), 2.81 (s, 4H), 2.21-2.00 (br m, 2H), 1.79-1.59 (m, 2H); 390.2 |
| 27 | Example 1[5]; P1 | 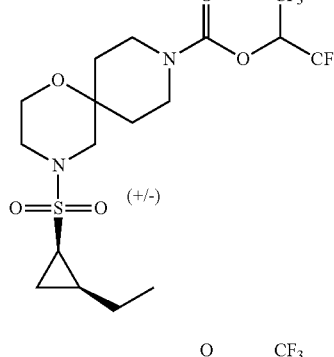 | 5.75 (septet, J = 6.2 Hz, 1H), 3.95-3.82 (m, 2H), 3.79 (dd, J = 5.0, 4.5 Hz, 2H), 3.36-3.21 (m, 4H), 3.14-3.03 (m, 2H), 2.09-2.00 (m, 2H), 2.00-1.94 (m, 1H), 1.60-1.45 (m, 3H), 1.44-1.35 (m, 2H), 1.34-1.27 (m, 1H), 1.02 (t, J = 7.3 Hz, 3H), 0.89-0.82 (m, 1H); 483.1 |
| 28 | Example 1[8]; P1 | 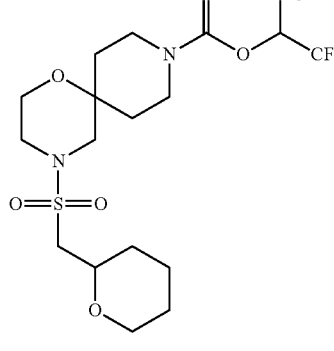 | 5.75 (septet, J = 6.2 Hz, 1H). 4.03-3.96 (m, 1H), 3.92-3.74 (m, 5H), 3.49-3.41 (m, 1H), 3.37-3.22 (m, 4H), 3.13 (dd, half of ABX pattern, J = 15.0, 8.4 Hz, 1H), 3.13-3.04 (m, 2H). 2.97 (dd, half of ABX pattern, J = 15.0, 2.6 Hz, 1H), 2.08-1.98 (br m, 2H), 1.92-1.84 (br m, 1H), 1.70-1.45 (m, 6H, assumed; partially obscured by water peak), 1.42-1.30 (m, 1H); 513.2 |
| 29 | Example 4[8]; P1 | 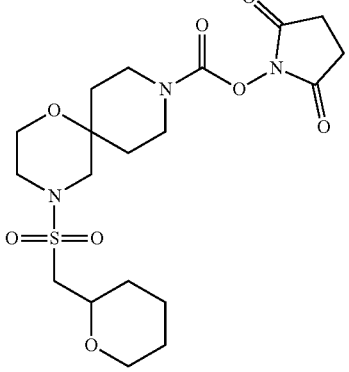 | 4.03-3.89 (m, 2H), 3.89-3.73 (m, 4H), 3.49-3.35 (m, 2H), 3.35-3.22 (m, 3H), 3.14-3.05 (m, 2H), 3.14 (dd, half of ABX pattern, J = 14.5, 8.4 Hz, 1H), 2.97 (dd, half of ABX pattern, J = 15.0, 2.6 Hz, 1H), 2.83 (s, 4H), 2.11-1.99 (br m, 2H), 1.92-1.84 (br m, 1H), 1.77-1.50 (m, 6H, assumed; partially obscured by water peak), 1.41-1.30 (m, 1H); 460.0 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 30 | Example 7[9]; P1 | 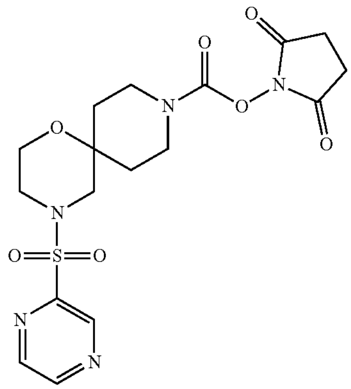 [SMILES: O=C(ON1C(=O)CCC1=O)N1CCC2(CC1)CN(S(=O)(=O)c1cnccn1)CCO2] | 9.16 (d, J = 1.5 Hz, 1H), 8.84 (d, J = 2.5 Hz, 1H), 8.72-8.69 (m, 1H), 4.02-3.91 (br m, 1H), 3.91-3.78 (m, 3H), 3.46-3.14 (m, 6H), 2.83 (s, 4H), 2.10-1.98 (m, 2H), 1.74-1.5 (m, 2H, assumed; partially obscured by water peak); 440.1 |
| 31 | Example 1[9]; P1 | 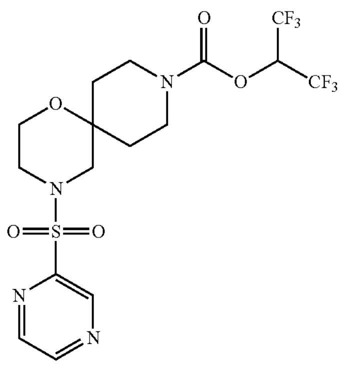 [SMILES: O=C(OC(C(F)(F)F)C(F)(F)F)N1CCC2(CC1)CN(S(=O)(=O)c1cnccn1)CCO2] | 9.16 (d, J = 1.5 Hz, 1H), 8.84 (d, J = 2.5 Hz, 1H), 8.72-8.68 (m, 1H), 5.76 (septet, J = 6.3 Hz, 1H), 3.95-3.84 (m, 2H), 3.83 (dd, J = 5.0, 5.0 Hz, 2H), 3.42-3.15 (m, 6H), 2.08-1.98 (m, 2H), 1.65-1.48 (m, 2H, assumed; partially obscured by water peak); 493.2 |
| 32 | Example 1; P2 | 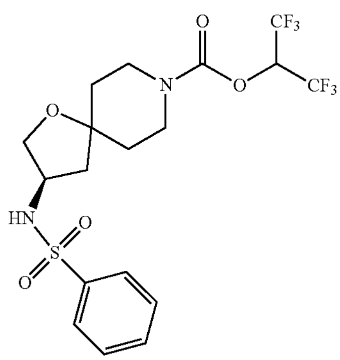 [SMILES: O=C(OC(C(F)(F)F)C(F)(F)F)N1CCC2(CC1)C[C@@H](NS(=O)(=O)c1ccccc1)CO2] | 7.88 (d, J = 7.5 Hz, 2H), 7.63 (dd, half of ABX pattern, J = 7.5, 7.0 Hz, 1H), 7.56 (dd, half of ABX pattern, J = 7.5, 7.5 Hz, 2H), 5.79-5.69 (m, 1H), 4.64 (br d, J = 8.0 Hz, 1H), 4.03-3.92 (br m, 1H), 3.89-3.71 (m, 3H), 3.54 (dd, 9.8, 4.3 Hz, 1H), 3.40-3.24 (m, 2H), 2.05-1.95 (m, 1H), 1.77-1.41 (m, 5H, assumed; partially obscured by water peak); 490.9 |
| 33 | Example 1; C4 | 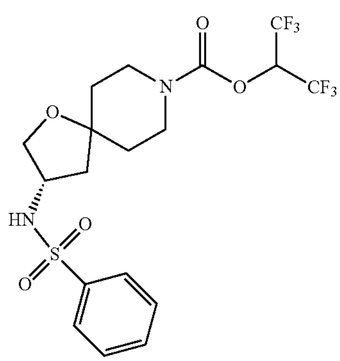 [SMILES: O=C(OC(C(F)(F)F)C(F)(F)F)N1CCC2(CC1)C[C@H](NS(=O)(=O)c1ccccc1)CO2] | 7.89 (d, J = 7.5 Hz, 2H), 7.63 (dd, half of ABX pattern, J = 7.5, 7.0 Hz, 1H), 7.55 (dd, half of ABX pattern, J = 7.5, 7.0 Hz, 2H), 5.80-5.68 (m, 1H), 4.78 (br d, J = 7.5 Hz, 1H), 4.02-3.91 (br m, 1H), 3.89-3.70 (m, 3H), 3.54 (dd, J = 9.5, 4.5 Hz, 1H), 3.41-3.22 (m, 2H), 2.06-1.93 (m, 1H), 1.78-1.40 (m, 5H, assumed; partially obscured by water peak); 490.9 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 34 | Example 5; C3 | 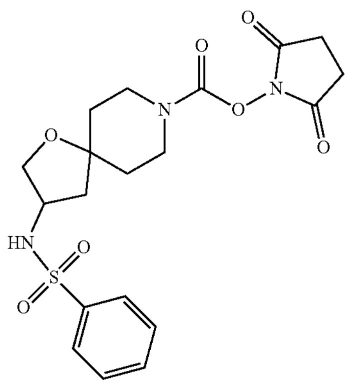 [SMILES: O=C(ON1C(=O)CCC1=O)N1CCC2(CC1)CC(NS(=O)(=O)c1ccccc1)CO2] | 7.91-7.86 (m, 2H), 7.63 (br dd, half of ABX pattern, J = 7.5, 7.0 Hz, 1H), 7.56 (br dd, half of ABX pattern, J = 8.0, 7.0 Hz, 2H), 4.63 (br d, J = 8.0 Hz, 1H), 4.02-3.93 (br m, 1H), 3.91-3.81 (br m, 1H), 3.84 (dd, J = 9.5, 5.5 Hz, 1H), 3.81-3.72 (br m, 1H), 3.54 (dd, J = 9.8, 4.3 Hz, 1H), 3.48-3.35 (br m, 1H), 3.35-3.23 (br m, 1H), 2.82 (s, 4H), 1.99 (dd, half of ABX pattern, J = 13.3, 7.8 Hz, 1H), 1.78-1.66 (m, 2H), 1.66-1.51 (m, 3H, assumed; partially obscured by water peak); 437.9 |
| 35 | Example 7[10]; P4 | 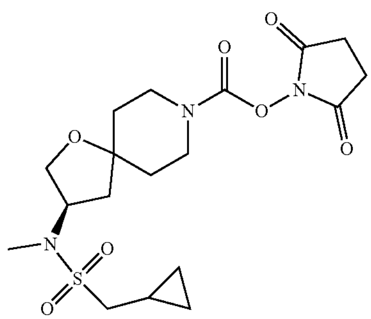 [SMILES: CN([C@H]1COC2(CCN(C(=O)ON3C(=O)CCC3=O)CC2)C1)S(=O)(=O)CC1CC1] | 4.75-4.65 (m, 1H), 4.00-3.75 (br m, 2H), 3.97 (dd, half of ABX pattern, J = 9.9, 7.7 Hz, 1H), 3.82 (dd, half of ABX pattern, J = 9.9, 5.5 Hz, 1H), 3.54-3.22 (m, 2H), 2.88 (s, 3H), 2.87 (d, J = 7.5 Hz, 2H), 2.83 (s, 4H), 2.09 (dd, half of ABX pattern, J = 13.2, 9.2 Hz, 1H), 1.94-1.71 (m, 4H), 1.7-1.5 (m, 1H, assumed; obscured by water peak), 1.15-1.03 (m, 1H), 0.75-0.67 (m, 2H), 0.40-0.34 (m, 2H); LCMS m/z 452.3 [M + Na$^+$] |
| 36 | Example 1[10]; P4 | 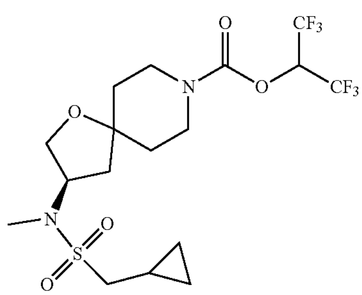 [SMILES: CN([C@H]1COC2(CCN(C(=O)OC(C(F)(F)F)C(F)(F)F)CC2)C1)S(=O)(=O)CC1CC1] | 5.75 (septet, J = 6.2 Hz, 1H), 4.75-4.65 (m, 1H), 4.01-3.93 (m, 1H), 3.92-3.76 (m, 3H), 3.46-3.25 (m, 2H), 2.88 (s, 3H), 2.87 (d, J = 7.0 Hz, 2H), 2.09 (dd, J = 13.6, 9.0 Hz, 1H), 1.84-1.69 (m, 4H), 1.55-1.43 (m, 1H), 1.15-1.03 (m, 1H), 0.75-0.68 (m, 2H), 0.41-0.34 (m, 2H); LCMS m/z 505.2 [M + Na$^+$] |
| 37 | P5[11] | 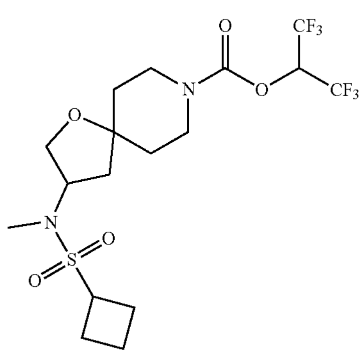 [SMILES: CN(C1COC2(CCN(C(=O)OC(C(F)(F)F)C(F)(F)F)CC2)C1)S(=O)(=O)C1CCC1] | 5.75 (septet, J = 6.1 Hz, 1H), 4.72-4.61 (m, 1H), 3.97-3.69 (m, 5H), 3.45-3.24 (m, 2H), 2.83 (s, 3H), 2.60-2.47 (m, 2H), 2.32-2.21 (m, 2H), 2.09-1.97 (m, 3H), 1.80-1.69 (m, 4H), 1.55-1.42 (m, 1H); 483.2 |

TABLE 10-continued

Method of Preparation, Structure, and Physicochemical Data for Examples 15-53.

| Example Number | Method of Preparation; Non-commercial starting materials | Structure | ¹H NMR (400 MHz, CDCl₃) δ; Mass spectrum, observed ion m/z [M + H]⁺ or HPLC retention time; Mass spectrum m/z [M + H]⁺ (unless otherwise indicated) |
|---|---|---|---|
| 38 | P5[11] | 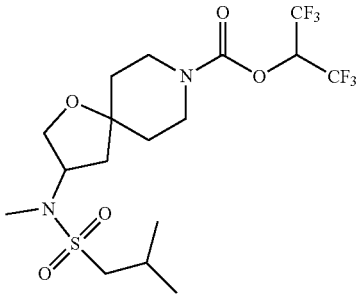 [SMILES: CC(C)CS(=O)(=O)N(C)C1COC2(CCN(C(=O)OC(C(F)(F)F)C(F)(F)F)CC2)C1] | 5.75 (septet, J = 6.2 Hz, 1H), 4.71-4.62 (m, 1H), 4.01-3.92 (m, 1H), 3.92-3.76 (m, 3H), 3.45-3.25 (m, 2H), 2.84 (s, 3H), 2.78 (dd, half of ABX pattern, J = 14, 7 Hz, 1H), 2.74 (dd, half of ABX pattern, J = 13.5, 6.5 Hz, 1H), 2.32-2.17 (m, 1H), 2.08 (dd, half of ABX pattern, J = 13.3, 8.8 Hz, 1H), 1.82-1.70 (m, 4H), 1.57-1.43 (m, 1H), 1.11 (d, J = 7.0 Hz, 3H), 1.11 (d, J = 6.5 Hz, 3H); 485.2 |
| 39 | P5[11] | 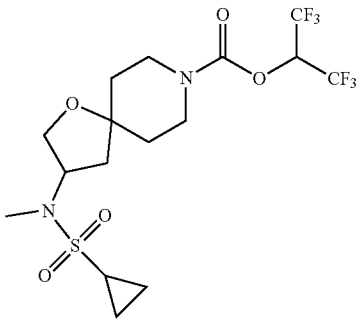 [SMILES: CN(C1COC2(CCN(C(=O)OC(C(F)(F)F)C(F)(F)F)CC2)C1)S(=O)(=O)C1CC1] | 5.75 (septet, J = 6.1 Hz, 1H), 4.73-4.63 (m, 1H), 4.00-3.92 (m, 1H), 3.92-3.76 (m, 3H), 3.45-3.24 (m, 2H), 2.88 (s, 3H), 2.30-2.21 (m, 1H), 2.08 (dd, half of ABX pattern, J = 13.6, 9.0 Hz, 1H), 1.86-1.69 (m, 4H), 1.57-1.42 (m, 1H), 1.21-1.14 (m, 2H), 1.03-0.96 (m, 2H); 469.2 |
| 40 | P5[11] | 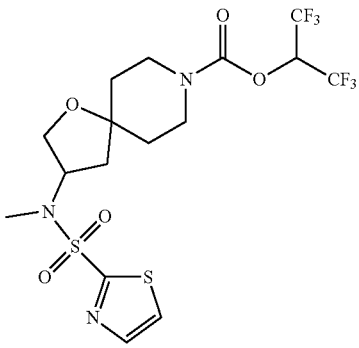 [SMILES: CN(C1COC2(CCN(C(=O)OC(C(F)(F)F)C(F)(F)F)CC2)C1)S(=O)(=O)c1nccs1] | 7.98 (d, J = 3.0 Hz, 1H), 7.65 (d, J = 3.5 Hz, 1H), 5.74 (septet, J = 6.3 Hz, 1H), 4.94-4.85 (m, 1H), 3.96-3.73 (m, 4H), 3.42-3.22 (m, 2H), 2.95 (s, 3H), 2.04 (dd, J = 13.6, 9.0 Hz, 1H), 1.82-1.67 (m, 3H, assumed; partially obscured by water peak), 1.65 (dd, J = 13.8, 6.8 Hz, 1H), 1.53-1.39 (m, 1H); 512.2 |
| 41 | P5[11] | 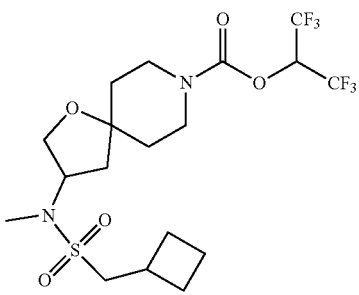 [SMILES: CN(C1COC2(CCN(C(=O)OC(C(F)(F)F)C(F)(F)F)CC2)C1)S(=O)(=O)CC1CCC1] | 5.75 (septet, J = 6.3 Hz, 1H), 4.68-4.59 (m, 1H), 4.00-3.92 (m, 1H), 3.92-3.76 (m, 3H), 3.45-3.25 (m, 2H), 3.05-2.95 (m, 2H), 2.85-2.72 (m, 1H), 2.83 (s, 3H), 2.26-2.16 (m, 2H), 2.08 (dd, J = 13.0, 9.0 Hz, 1H), 2.02-1.94 (m, 1H), 1.93-1.82 (m, 3H), 1.82-1.69 (m, 4H), 1.58-1.43 (m, 1H); 497.2 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 42 | P5[11] | 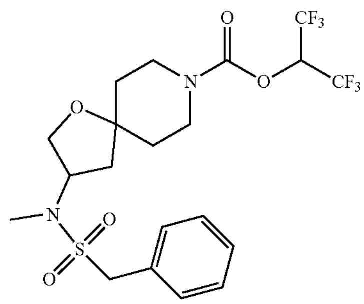 [SMILES: CN(C1COC2(CCN(C(=O)OC(C(F)(F)F)C(F)(F)F)CC2)C1)S(=O)(=O)Cc1ccccc1] | 7.43-7.36 (m, 5H), 5.74 (septet, J = 6.2 Hz, 1H), 4.41-4.30 (m, 1H), 4.24 (s, 2H), 3.84-3.67 (m, 2H), 3.61-3.50 (m, 2H), 3.40-3.19 (m, 2H), 2.73 (s, 3H), 1.74-1.53 (m, 4H, assumed; partially obscured by water peak), 1.55 (dd, half of ABX pattern, J = 13.0, 7.5 Hz, 1H), 1.44-1.29 (m, 1H); LCMS m/z 541.2 [M + Na$^+$] |
| 43 | P6[12] | 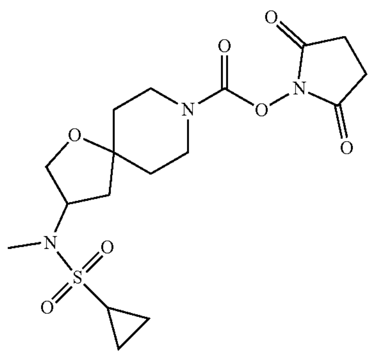 [SMILES: CN(C1COC2(CCN(C(=O)ON3C(=O)CCC3=O)CC2)C1)S(=O)(=O)C1CC1] | 4.74-4.63 (m, 1H), 4.01-3.76 (br m, 2H), 3.97 (dd, half of ABX pattern, J = 9.7, 7.5 Hz, 1H), 3.86 (dd, half of ABX pattern, J = 10.1, 5.3 Hz, 1H), 3.54-3.23 (m, 3H), 2.88 (s, 3H), 2.83 (br s, 4H), 2.30-2.22 (m, 1H), 2.09 (dd, J = 13.2, 8.8 Hz, 1H), 1.96-1.70 (m, 4H), 1.25-1.15 (m, 2H), 1.04-0.94 (m, 2H); LCMS m/z 438.1 [M + Na$^+$] |
| 44 | P6[12] | 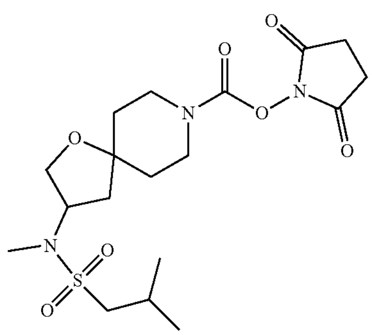 [SMILES: CC(C)CS(=O)(=O)N(C)C1COC2(CCN(C(=O)ON3C(=O)CCC3=O)CC2)C1] | 4.71-4.62 (m, 1H), 4.00-3.77 (br m, 2H), 3.97 (dd, half of ABX pattern, J = 10.0, 7.5 Hz, 1H), 3.81 (dd, half of ABX pattern, J = 10.0, 5.5 Hz, 1H), 3.54-3.23 (m, 2H), 2.84 (s, 3H), 2.83 (br s, 4H), 2.78 (dd, half of ABX pattern, J = 14, 7 Hz, 1H), 2.74 (dd, half of ABX pattern, J = 14, 6 Hz, 1H), 2.31-2.19 (m, 1H), 2.08 (dd, J = 13.3, 8.8 Hz, 1H), 1.95-1.73 (m, 4H), 1.7-1.52 (m, 1H, assumed; partially obscured by water peak), 1.11 (d, J = 6.5 Hz, 3H), 1.11 (d, J = 6.5 Hz, 3H); 432.3 |
| 45 | P6[12] | 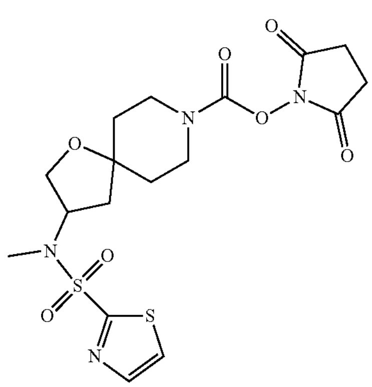 [SMILES: CN(C1COC2(CCN(C(=O)ON3C(=O)CCC3=O)CC2)C1)S(=O)(=O)c1nccs1] | 7.99 (d, J = 3.1 Hz, 1H), 7.65 (d, J = 3.1 Hz, 1H), 4.93-4.84 (m, 1H), 3.97-3.72 (br m, 2H), 3.92 (dd, half of ABX pattern, J = 10.6, 7.5 Hz, 1H), 3.76 (dd, half of ABX pattern, J = 10.3, 5.1 Hz, 1H), 3.50-3.17 (m, 2H), 2.95 (s, 3H), 2.82 (br s, 4H), 2.02 (dd, J = 13.6, 9.2 Hz, 1H), 1.91-1.69 (m, 3H), 1.69-1.47 (m, 2H, assumed; partially obscured by water peak); 459.1 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 46 | P6[12] | 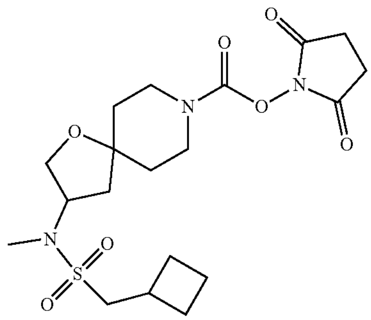 [SMILES: CN(C1COC2(CCN(C(=O)ON3C(=O)CCC3=O)CC2)C1)S(=O)(=O)CC1CCC1] | 4.68-4.58 (m, 1H), 4.00-3.75 (br m, 2H), 3.96 (dd, half of ABX pattern, J = 10.1, 7.5 Hz, 1H), 3.80 (dd, half of ABX pattern, J = 9.9, 5.5 Hz, 1H), 3.53-3.24 (m, 2H), 3.05-2.95 (m, 2H), 2.86-2.74 (m, 1H), 2.83 (br s, 7H), 2.27-2.17 (m, 2H), 2.09 (dd, J = 13.2, 8.8 Hz, 1H), 2.04-1.72 (m, 8H), 1.69-1.52 (m, 1H, assumed; largely obscured by water peak); LCMS m/z 466.3 [M + Na$^+$] |
| 47 | P6[12] | 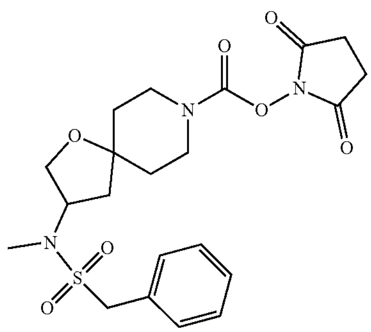 [SMILES: CN(C1COC2(CCN(C(=O)ON3C(=O)CCC3=O)CC2)C1)S(=O)(=O)Cc1ccccc1] | 7.44-7.36 (m, 5H), 4.40-4.30 (m, 1H), 4.24 (s, 2H), 3.93-3.66 (m, 2H), 3.59 (dd, half of ABX pattern, J = 9.8, 7.3 Hz, 1H), 3.53 (dd, half of ABX pattern, J-9.8, 5.8 Hz, 1H), 3.48-3.16 (m, 2H), 2.82 (br s, 4H), 2.73 (s, 3H), 1.85-1.37 (m, 6H, assumed; partially obscured by water peak); LCMS m/z 488.3 [M + Na$^+$] |
| 48 | P6[12] | 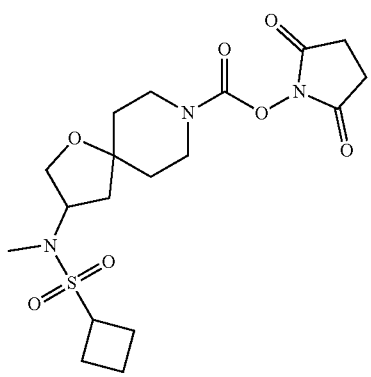 [SMILES: CN(C1COC2(CCN(C(=O)ON3C(=O)CCC3=O)CC2)C1)S(=O)(=O)C1CCC1] | 4.71-4.61 (m, 1H), 4.00-3.68 (m, 5H), 3.52-3.21 (m, 2H), 2.83 (s, 7H), 2.60-2.46 (m, 2H), 2.33-2.20 (m, 2H), 2.11-1.97 (m, 3H), 1.93-1.51 (m, 5H, assumed; partially obscured by water peak); 430.3 |
| 49 | Example 1[13]; P3 | 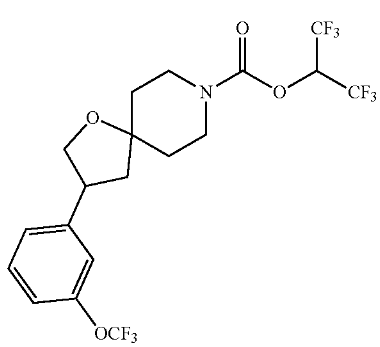 [SMILES: O=C(OC(C(F)(F)F)C(F)(F)F)N1CCC2(CC1)CC(c1cccc(OC(F)(F)F)c1)CO2] | 7.35 (dd, J = 8.0, 7.5 Hz, 1H), 7.18 (br d, J = 7.5 Hz, 1H), 7.13-7.07 (m, 2H), 5.77 (septet, J = 6.2 Hz, 1H), 4.25 (dd, J = 8.0, 8.0 Hz, 1H), 3.93-3.82 (m, 2H), 3.81 (dd, J = 9.0, 9.0 Hz, 1H), 3.61-3.50 (m, 1H), 3.50-3.35 (m, 2H), 2.29 (dd, J = 12.8, 8.3 Hz, 1H), 1.89-1.59 (m, 5H); 496.2 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 50 | Example 7$^{13}$; P3 | 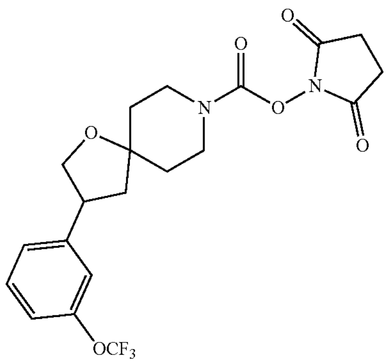 [SMILES: O=C(ON1C(=O)CCC1=O)N1CCC2(CC1)CC(c1cccc(OC(F)(F)F)c1)CO2] | 7.35 (dd, J = 8.0, 8.0 Hz, 1H), 7.18 (br d, J = 7.5 Hz, 1H), 7.13-7.07 (m, 2H), 4.24 (dd, J = 8.5, 7.5 Hz, 1H), 4.00-3.91 (br m, 1H), 3.90-3.82 (br m, 1H), 3.80 (dd, J = 9.0, 9.0 Hz, 1H), 3.60-3.48 (m, 2H), 3.48-3.33 (m, 1H), 2.83 (s, 4H), 2.30 (dd, J = 12.8, 8.3 Hz, 1H), 1.93-1.65 (m, 5H); 443.2 |
| 51 | P6$^{12}$ | 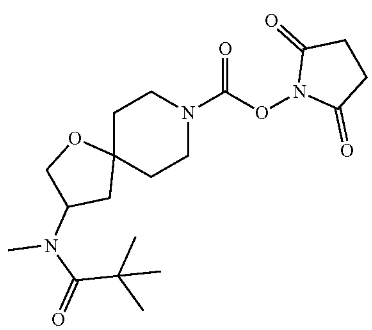 [SMILES: CN(C(=O)C(C)(C)C)C1COC2(CCN(C(=O)ON3C(=O)CCC3=O)CC2)C1] | 5.24-5.13 (m, 1H), 3.99-3.74 (br m, 2H), 3.96 (dd, half of ABX pattern, J = 9.9, 7.7 Hz, 1H), 3.78 (dd, half of ABX pattern, J = 9.9, 5.5 Hz, 1H), 3.55-3.26 (m, 2H), 2.96 (s, 3H), 2.82 (s, 4H), 2.11 (dd, J = 13.2, 8.8 Hz, 1H), 1.95-1.76 (m, 3H), 1.72 (dd, J = 13.2, 7.5 Hz, 1H), 1.67-1.53 (m, 1H, assumed; largely obscured by water peak), 1.30 (s, 9H); 396.3 |
| 52 | P5$^{11}$ | 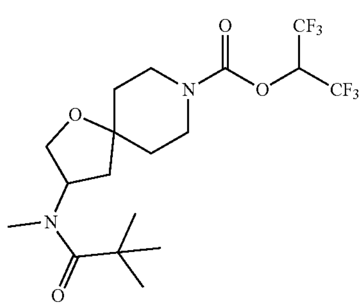 [SMILES: CN(C(=O)C(C)(C)C)C1COC2(CCN(C(=O)OC(C(F)(F)F)C(F)(F)F)CC2)C1] | 5.75 (septet, J = 6.3 Hz, 1H), 5.24-5.13 (m, 1H), 4.00-3.91 (m, 1H), 3.91-3.77 (m, 2H), 3.78 (dd, J = 9.8, 5.3 Hz, 1H), 3.47-3.27 (m, 2H), 2.96 (s, 3H), 2.10 (dd, J = 13.6, 9.0 Hz, 1H), 1.83-1.65 (m, 4H, assumed; partially obscured by water peak), 1.60-1.45 (m, 1H), 1.29 (s, 9H); 449.3 |

TABLE 10-continued

Method of Preparation, Structure, and Physicochemical Data for Examples 15-53.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 53 | Example 7; C38 | 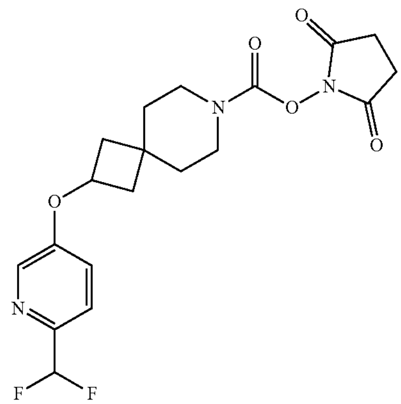 [SMILES: O=C(ON1C(=O)CCC1=O)N1CCC2(CC1)CC(Oc1ccc(C(F)F)nc1)C2] | 8.21 (d, J = 2.5 Hz, 1H), 7.56 (d, J = 8.5 Hz, 1H), 7.17 (dd, J = 8.5, 3.0 Hz, 1H), 6.61 (t, J$_{HF}$ = 55.7 Hz, 1H), 4.82-4.73 (m, 1H), 3.66-3.39 (m, 4H), 2.82 (s, 4H), 2.54-2.44 (m, 2H), 2.08-1.99 (m, 2H), 1.81-1.65 (br m, 4H, assumed; partially obscured by water peak); 410.2 |

[1] The requisite ter-butyl 4-benzyl-1-oxa-4,9-diazaspiro[5.5] undecane-9-carboxylate was synthesized from P1 via potassium carbonate-mediated alkylation with benzyl bromide.
[2] Conditions for analytical HPLC. Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL./minute.
[3] Conditions for analytical HPLC. Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.
[4] Conditions for analytical HPLC. Column: Waters XBridge C18, 2.1 × 50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute.
[5] cis-2-Ethylcyclopropanesulfonyl chloride may be prepared in the following manner: propan-2-yl cis-2-ethenylcyclopropanesulfonate may be synthesized from butadiene using the method described by R. Pellicciari et al., J. Med Chem. 2007, 50, 4630-4641. Hydrogenation provides propan-2-yl cis-2-ethylcyclopropanesulfonate, which is then treated with sodium iodide in acetone at elevated temperature to afford sodium cis-2-ethylcyclopropanesulfonate. Treatment of this material with thionyl chloride affords the requisite cis-2-ethylcyclopropanesulfonyl chloride.
[6] In this case, 1-hydroxypyrrolidine-2,5-dione was used in place of 1,1,1,3,3,3-hexafluoropropan-2-ol in the final step, and 4-(dimethylamino)pyridine was added to the reaction mixture.
[7] Reaction of P1 with 2-(bromomethyl)pyrazine and N,N-diisopropylethylamine afforded tert-butyl 4-(pyrazin-2-ylmethyl)-1-oxa-4,9-diazaspiro[5.5]undecane-9-carboxylate; subsequent deprotection with trifluoroacetic acid provided 4-(pyrazin-2-ylmethyl)-1-oxa-4,9-diazaspiro[5.5]undecane, trifluoroacetate salt.
[8] Reaction of P1 with tetrahydro-2H-pyran-2-ylmethanesulfonyl chloride in the presence of triethylamine and 4-(dimethylamino)pyridine, followed by deprotection using trifluoroacetic acid, afforded the requisite 4-[(tetrahydro-2H-pyran-2-ylmethyl)sulfonyl]-1-oxa-4,9-diazaspiro[5.5]undecane, trifluoroacetate salt.
[9] Pyrazine-2-sulfonyl chloride (prepared from pyrazine-2(1H)-thione using the method of S. W. Wright et al., J. Org. Chem. 2006, 71, 1080-1084) was reacted with P1 to provide tert-butyl 4-(pyrazin-2-ylsulfonyl)-1-oxa-4,9-diazaspiro[5.5]undecane-9-carboxylate. Subsequent deprotection with trifluoroacetic acid afforded 4-(pyrazin-2-ylsulfonyl)-1-oxa-4,9-diazaspiro[5.5]undecane, trifluoroacetate salt.
[10] Compound P4 was converted to 1-cyclopropyl-N-methyl-N-[(3R)-1-oxa-8-azaspiro[4.5]dec-3-yl]methanesulfonamide, trifluoroacetate salt using the general method described in Preparation P5 for synthesis of C9.
[11] This Example was synthesized via reaction of P5 with the appropriate sulfonyl chloride or acyl chloride, in the presence of triethylamine.
[12] This Example was synthesized via reaction of P6 with the appropriate sulfonyl chloride or acyl chloride, in the presence of triethylamine.
[13] Reaction of P3 with 3-bromophenyl trifluoromethyl ether in the presence of nickel(II) iodide, zinc, 4,4'-di-tert-butyl-2,2'-bipyridine, and pyridine provided tert-butyl 3-[3-(trifluoromethoxy)phenyl]-1-oxa-8-azaspiro[4.5]decane-8-carboxylate, which was deprotected with trifluoroacetic acid to afford the requisite 3-[3-(trifluoromethoxy)phenyl]-1-oxa-8-azaspiro[4.5]decane, trifluoroacetate salt.

Example AA

MAGL Enzymatic Assay

Assessment of MAGL inhibition utilizes human recombinant Monoacylglycerol Lipase and the fluorogenic substrate 7-hydroxycoumarinyl arachidonate (7-HCA, Biomol ST-502). 400 nL of a test compound at decreasing concentration (ranging from 150 μM down to 1.5 nM) was spotted into a 384-well back plate (PerkinElmer, 6007279) using a Labcyte Echo, followed by addition of 10 μL of MAGL enzyme in assay buffer (50 mM HEPES, pH 7.4, 100 mM NaCl, 5 mM MgCl$_2$, 0.1% Triton X-100 and 25% glycerin). An equal volume of 7-HCA in assay buffer with 10% DMSO was added either immediately (T=0 min) or after a 30 minute incubation (T=30 min) to initiate the reaction. The final concentration of MAGL enzyme was 88 μM and 7-HCA substrate was 5 μM. After these dilutions, the final concentration of the test compound ranged from 3 μM to 0.03 nM. The reaction was allowed to progress for 60 minutes, after which the plate was read at an Ex/Em of 340/465. Percent inhibitions were calculated based on control wells containing no compound (0% inhibition) and a control compound (e.g., a MAGL inhibitor whose activity is known or was previously reported in the literature, such as one with about 100% inhibition). IC$_{50}$ values were generated based on a four parameter fit model using ABASE software from IDBS. See e.g., Wang, Y. et al., "A Fluorescence-Based Assay for Monoacylglycerol Lipase Compatible with Inhibitor Screening," Assay and Drug Development Technologies, 2008, Vol. 6 (3) pp 387-393 (reporting an assay for measuring MAGL activity).

To measure MAGL inactivation, the same protocol for the (T=0 min) MAGL inhibition IC$_{50}$ assay was performed with data collected every minute to acquire enzyme progress curves at decreasing concentrations of compound. K$_{obs}$ values were calculated from this data and k$_{inact}$/K$_I$ ratios were determined from a plot of K$_{obs}$ values vs. compound concentrations.

TABLE 11

Biological Data (MAGL IC$_{50}$, and MAGL k$_{inact}$/K$_I$) and Compound Name for Examples 1-53.

| Example Number | MAGL (T = 0 min) IC$_{50}$ (nM)$^a$ | MAGL (T = 30 min) IC$_{50}$ (nM)$^a$ | MAGL K$_{inact}$/K$_I$ (1/s per M)$^a$ | Compound Name |
|---|---|---|---|---|
| 1 | 3.09 | 0.259 | 543000 | 1,1,1,3,3,3-hexafluoropropan-2-yl 4-(phenylsulfonyl)-1-oxa-4,9-diazaspiro[5.5]undecane-9-carboxylate |
| 2 | 7.94 | 1.00 | 85900 | 1,1,1,3,3,3-hexafluoropropan-2-yl 4-[(4-fluorophenyl)sulfonyl]-1-oxa-4,9-diazaspiro[5.5]undecane-9-carboxylate |
| 3 | 59.9 | 8.49 | 6240 | 1,1,1,3,3,3-hexafluoropropan-2-yl 4-(tetrahydro-2H-pyran-3-ylmethyl)-1-oxa-4,9-diazaspiro[5.5]undecane-9-carboxylate |
| 4 | 204 | 20.3 | 2140 | 1-[({4-[(4-fluorophenyl)sulfonyl]-1-oxa-4,9-diazaspiro[5.5]undec-9-yl}carbonyl)oxy]pyrrolidine-2,5-dione |
| 5 | 1480 | 136 | N.D. | 1-{[(4-benzyl-1-oxa-4,9-diazaspiro[5.5]undec-9-yl}carbonyl]oxy}pyrrolidine-2,5-dione |
| 6 | 4.39 | 0.470 | 188000 | 1,1,1,3,3,3-hexafluoropropan-2-yl (3R)-3-[methyl(phenylsulfonyl)amino]-1-oxa-8-azaspiro[4.5]decane-8-carboxylate |
| 7 | 214 | 15.6 | 8060 | N-[(3R)-8-{[(2,5-dioxopyrrolidin-1-yl)oxy]carbonyl}-1-oxa-8-azaspiro[4.5]dec-3-yl]-N-methylbenzenesulfonamide |
| 8 | 35.0 | 3.29 | 15700 | 1,1,1,3,3,3-hexafluoropropan-2-yl 2-benzoyl-2,8-diazaspiro[4.5]decane-8-carboxylate |
| 9 | 760 | 57.4 | N.D. | 1-{[(2-benzoyl-2,8-diazaspiro[4.5]dec-8-yl)carbonyl]oxy}pyrrolidine-2,5-dione |
| 10 | 637 | 80.6 | N.D. | 4-(8-{[(2,5-dioxopyrrolidin-1-yl)oxy]carbonyl}-1-oxa-8-azaspiro[4.5]dec-3-yl)benzonitrile |
| 11 | 17.6 | 2.46 | 9710 | 1,1,1,3,3,3-hexafluoropropan-2-yl 3-(4-cyanophenyl)-1-oxa-8-azaspiro[4.5]decane-8-carboxylate |
| 12 | 57.0 | 4.90 | N.D. | 1,1,1,3,3,3-hexafluoropropan-2-yl(3R)-3-(4-fluoro-1H-pyrazol-1-yl)-1-oxa-8-azaspiro[4.5]decane-8-carboxylate |
| 13 | 1950 | 121 | N.D. | 1-({[(3R)-3-(4-fluoro-1H-pyrazol-1-yl)-1-oxa-8-azaspiro[4.5]dec-8-yl]carbonyl}oxy)pyrrolidine-2,5-dione |
| 14 | 3.63$^c$ | 0.942$^c$ | N.D. | 1,1,1,3,3,3-hexafluoropropan-2-yl 2-{6-(difluoromethyl)pyridin-3-yl]oxy}-7-azaspiro[3.5]nonane-7-carboxylate |
| 15 | 55.8 | 7.86 | 14400 | 1,1,1,3,3,3-hexafluoropropan-2-yl 4-benzyl-1-oxa-4,9-diazaspiro[5.5]undecane-9-carboxylate |
| 16 | 78.5 | 10.4 | 9540 | 1,1,1,3,3,3-hexafluoropropan-2-yl 4-{[6-(trifluoromethyl)pyridin-3-yl]methyl}-1-oxa-4,9-diazaspiro[5.5]undecane-9-carboxylate |
| 17 | 67.5 | 10.5 | 7720 | 1,1,1,3,3,3-hexafluoropropan-2-yl 4-(4-fluorobenzyl)-1-oxa-4,9-diazaspiro[5.5]undecane-9-carboxylate |
| 18 | 90.5 | 14.0 | 6280 | 1,1,1,3,3,3-hexafluoropropan-2-yl 4-[(2-cyanopyridin-3-yl)methyl]-1-oxa-4,9-diazaspiro[5.5]undecane-9-carboxylate |
| 19 | 221 | 28.5 | N.D. | 1,1,1,3,3,3-hexafluoropropan-2-yl 4-(1,3-thiazol-2-ylmethyl)-1-oxa-4,9-diazaspiro[5.5]undecane-9-carboxylate |
| 20 | 255 | 35.0 | N.D. | 1,1,1,3,3,3-hexafluoropropan-2-yl 4-(pyrazin-2-ylmethyl)-1-oxa-4,9-diazaspiro[5.5]undecane-9-carboxylate |
| 21 | 307 | 40.5 | N.D. | 1,1,1,3,3,3-hexafluoropropan-2-yl 4-(pyridin-2-ylmethyl)-1-oxa-4,9-diazaspiro[5.5]undecane-9-carboxylate |
| 22 | 454 | 46.3 | N.D. | 1-[({4-[(cis-2-ethylcyclopropyl)sulfonyl]-1-oxa-4,9-diazaspiro[5.5]undec-9-yl}carbonyl)oxy]pyrrolidine-2,5-dione |
| 23 | 432 | 58.0 | N.D. | 1,1,1,3,3,3-hexafluoropropan-2-yl 4-(tetrahydrofuran-3-ylmethyl)-1-oxa-4,9-diazaspiro[5.5]undecane-9-carboxylate |
| 24 | 443 | 81.9 | N.D. | 1,1,1,3,3,3-hexafluoropropan-2-yl 4-(2-methylpropyl)-1-oxa-4,9-diazaspiro[5.5]undecane-9-carboxylate |
| 25 | 1320 | 158 | N.D. | 1-({[4-(4-fluorobenzyl)-1-oxa-4,9-diazaspiro[5.5]undec-9-yl]carbonyl}oxy)pyrrolidine-2,5-dione |

TABLE 11-continued

Biological Data (MAGL IC$_{50}$, and MAGL k$_{inact}$/K$_I$) and Compound Name for Examples 1-53.

| Example Number | MAGL (T = 0 min) IC$_{50}$ (nM)$^a$ | MAGL (T = 30 min) IC$_{50}$ (nM)$^a$ | MAGL K$_{inact}$/K$_I$ (1/s per M)$^a$ | Compound Name |
|---|---|---|---|---|
| 26 | >3000 | 539 | N.D. | 1-({[4-(pyrazin-2-ylmethyl)-1-oxa-4,9-diazaspiro[5.5]undec-9-yl]carbonyl}oxy)pyrrolidine-2,5-dione, trifluoroacetate salt |
| 27 | 6.25 | 0.679 | 148000 | 1,1,1,3,3,3-hexafluoropropan-2-yl 4-[(cis-2-ethylcyclopropyl)sulfonyl]-1-oxa-4,9-diazaspiro[5.5]undecane-9-carboxylate |
| 28 | 10.3 | 2.22 | 99000 | 1,1,1,3,3,3-hexafluoropropan-2-yl 4-[(tetrahydro-2H-pyran-2-ylmethyl)sulfonyl]-1-oxa-4,9-diazaspiro[5.5]undecane-9-carboxylate |
| 29 | 264 | 73.6 | N.D. | 1-[({4-[(tetrahydro-2H-pyran-2-ylmethyl)sulfonyl]-1-oxa-4,9-diazaspiro[5.5]undec-9-yl}carbonyl)oxy]pyrrolidine-2,5-dione |
| 30 | 1540 | 134 | N.D. | 1-({[4-(pyrazin-2-ylsulfonyl)-1-oxa-4,9-diazaspiro[5.5]undec-9-yl]carbonyl}oxy)pyrrolidine-2,5-dione |
| 31 | 20.8 | 2.26 | 19800 | 1,1,1,3,3,3-hexafluoropropan-2-yl 4-(pyrazin-2-ylsulfonyl)-1-oxa-4,9-diazaspiro[5.5]undecane-9-carboxylate |
| 32 | 13.7 | 1.08 | 67700 | 1,1,1,3,3,3-hexafluoropropan-2-yl (3R)-3-[(phenylsulfonyl)amino]-1-oxa-8-azaspiro[4.5]decane-8-carboxylate |
| 33 | 15.0 | 1.21 | 54800 | 1,1,1,3,3,3-hexafluoropropan-2-yl (3S)-3-[(phenylsulfonyl)amino]-1-oxa-8-azaspiro[4.5]decane-8-carboxylate |
| 34 | 418 | 52.8 | N.D. | N-(8-{[(2,5-dioxopyrrolidin-1-yl)oxy]carbonyl}-1-oxa-8-azaspiro[4.5]dec-3-yl)benzenesulfonamide |
| 35 | 1380 | 105 | N.D. | 1-cyclopropyl-N-[(3R)-8-{[(2,5-dioxopyrrolidin-1-yl)oxy]carbonyl}-1-oxa-8-azaspiro[4.5]dec-3-yl]-N-methylmethanesulfonamide |
| 36 | 37.3 | 2.79 | 25200 | 1,1,1,3,3,3-hexafluoropropan-2-yl (3R)-3-{[(cyclopropylmethyl)sulfonyl]methyl]amino}-1-oxa-8-azaspiro[4.5]decane-8-carboxylate |
| 37 | 25.8 | 3.03 | 22000 | 1,1,1,3,3,3-hexafluoropropan-2-yl 3-[(cyclobutylsulfonyl)(methyl)amino]-1-oxa-8-azaspiro[4.5]decane-8-carboxylate |
| 38 | 22.0 | 2.19 | 22600 | 1,1,1,3,3,3-hexafluoropropan-2-yl 3-{methyl[(2-methylpropyl)sulfonyl]amino}-1-oxa-8-azaspiro[4.5]decane-8-carboxylate |
| 39 | 47.7 | 4.04 | 21400 | 1,1,1,3,3,3-hexafluoropropan-2-yl 3-[(cyclopropylsulfonyl)(methyl)amino]-1-oxa-8-azaspiro[4.5]decane-8-carboxylate |
| 40 | 22.9 | 1.43 | 47700 | 1,1,1,3,3,3-hexafluoropropan-2-yl 3-[methyl(1,3-thiazol-2-ylsulfonyl)amino]-1-oxa-8-azaspiro[4.5]decane-8-carboxylate |
| 41 | 12.0 | 1.25 | 28000 | 1,1,1,3,3,3-hexafluoropropan-2-yl 3-{[(cyclobutylmethyl)sulfonyl)methyl]amino}-1-oxa-8-azaspiro[4.5]decane-8-carboxylate |
| 42 | 4.93 | 0.587 | 69300 | 1,1,1,3,3,3-hexafluoropropan-2-yl 3-[(benzylsulfonyl)(methyl)amino]-1-oxa-8-azaspiro[4.5]decane-8-carboxylate |
| 43 | 2720 | 225 | N.D. | N-(8-{[(2,5-dioxopyrrolidin-1-yl)oxy]carbonyl}-1-oxa-8-azaspiro[4.5]dec-3-yl)-N-methylcyclopropanesulfonamide |
| 44 | 794 | 79.8 | N.D. | N-(8-{[(2,5-dioxopyrrolidin-1-yl)oxy]carbonyl}-1-oxa-8-azaspiro[4.5]dec-3-yl)-N,2-dimethylpropane-1-sulfonamide |
| 45 | 655 | 73.0 | N.D. | N-(8-{[(2,5-dioxopyrrolidin-1-yl)oxy]carbonyl}-1-oxa-8-azaspiro[4.5]dec-3-yl)-N-methyl-1,3-thiazole-2-sulfonamide |
| 46 | 514 | 50.7 | N.D. | 1-cyclobutyl-N-(8-{[(2,5-dioxopyrrolidin-1-yl)oxy]carbonyl}-1-oxa-8-azaspiro[4.5]dec-3-yl)-N-methylmethanesulfonamide |
| 47 | 192 | 23.0 | 1870 | N-(8-{[(2,5-dioxopyrrolidin-1-yl)oxy]carbonyl}-1-oxa-8-azaspiro[4.5]dec-3-yl)-N-methyl-1-phenylmethanesulfonamide |

TABLE 11-continued

Biological Data (MAGL IC$_{50}$, and MAGL k$_{inact}$/K$_I$) and Compound Name for Examples 1-53.

| Example Number | MAGL (T = 0 min) IC$_{50}$ (nM)$^a$ | MAGL (T = 30 min) IC$_{50}$ (nM)$^a$ | MAGL K$_{inact}$/K$_I$ (1/s per M)$^a$ | Compound Name |
|---|---|---|---|---|
| 48 | 797 | 67.8 | N.D. | N-(8-{[(2,5-dioxopyrrolidin-1-yl)oxy]carbonyl}-1-oxa-8-azaspiro[4.5]dec-3-yl)-N-methylcyclobutanesulfonamide |
| 49 | 8.34 | 1.45 | 39700 | 1,1,1,3,3,3-hexafluoropropan-2-yl 3-[3-(trifluoromethoxy)phenyl]-1-oxa-8-azaspiro[4.5]decane-8-carboxylate |
| 50 | 19.0 | 2.46 | 26700 | 1-[({3-[3-(trifluoromethoxy)phenyl]-1-oxa-8-azaspiro[4.5]dec-8-yl}carbonyl)oxy]pyrrolidine-2,5-dione |
| 51 | >692 | >247 | 3290 | N-(8-{[(2,5-dioxopyrrolidin-1-yl)oxy]carbonyl}-1-oxa-8-azaspiro[4.5]dec-3-yl)-N,2,2-trimethylpropanamide |
| 52 | 8.04 | 0.666 | 109000 | 1,1,1,3,3,3-hexafluoropropan-2-yl 3-[(2,2-dimethylpropanoyl)(methyhamino)-1-oxa-8-azaspiro[4.5]decane-8-carboxylate |
| 53 | 69.3 | 10.1 | 1630 | 1-{[(2-{[6-(difluoromethyl)pyridin-3-yl]oxy}-7-azaspiro[3.5]non-7-yl)carbonyl]oxy}pyrrolidine-2,5-dione |

$^a$Reported IC$_{50}$ values or K$_{inact}$/K$_I$ values are the geometric mean of 2-4 determinations, unless otherwise indicated.
b. N.D. = not determined
$^c$The reported IC$_{50}$ value or K$_{inact}$/K$_I$ value is the result from a single determination.
d. The reported IC$_{50}$ value or K$_{inact}$/K$_I$ value is the geometric mean of determinations.

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A compound of Formula 1:

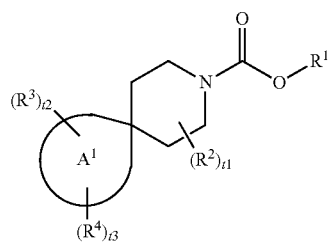

I or a pharmaceutically acceptable salt thereof, wherein:
the moiety of Formula M-1 of Formula I

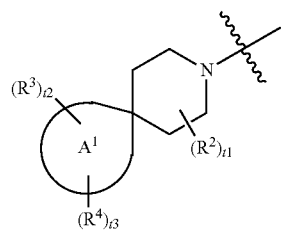

M-1 is a moiety of Formula M1-a:

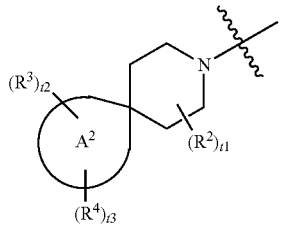

M-1a wherein ring A$^2$ is 5- or 6-membered heterocycloalkyl; or the moiety of Formula M-1 of Formula I

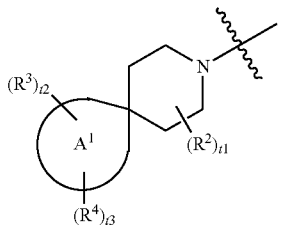

M-1 is a moiety of Formula M-1b, M-1c, M-1d, or M-1e:

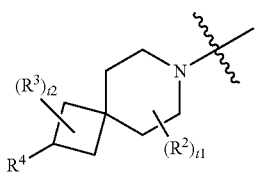

M-1b

-continued

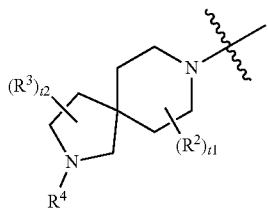
M-1c

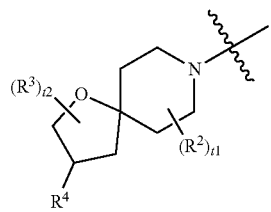
M-1d or

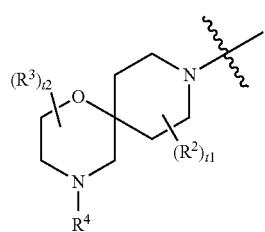
M-1e

R¹ is R^{1B};

R^{1B} is 2,5-dioxopyrrolidin-1-yl-;

R⁴ is selected from the group consisting of R⁶, —N(R⁵)(C(=O)R⁶), —N(R⁵)(S(=O)₂R⁶), —C(=O)—R⁶, —S(=O)₂R⁶, —NR⁵R⁶, —SO₂NR⁵R⁶, and —OR⁶;

R⁵ is selected from the group consisting of H, $C_{1-4}$ alkyl, $C_{3-4}$ cycloalkyl, and $C_{3-4}$ cycloalkyl-$C_{1-2}$ alkyl-;

R⁶ is selected from the group consisting of $C_{1-6}$ alkyl, $C_{3-10}$ cycloalkyl, 4- to 10-membered heterocycloalkyl, $C_{6-10}$ aryl, 5- to 10-membered heteroaryl, ($C_{3-10}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxyalkyl, $C_{3-4}$ cycloalkyl, $C_{3-4}$ cycloalkyl-$C_{1-2}$ alkyl-, $C_{1-4}$ alkoxy, $C_{1-4}$ haloalkoxy, —C(=O)$C_{1-4}$ alkyl, —C(=O)OH, —C(=O)O—$C_{1-4}$ alkyl, —C(=O)NH$C_{1-4}$ alkyl, —C(=O)N($C_{1-4}$ alkyl)₂, —OC(=O)—$C_{1-4}$ alkyl, —OC(=O)O—$C_{1-4}$ alkyl, —NH₂, —NH($C_{1-4}$ alkyl), —N($C_{1-4}$ alkyl)₂, —NHC(=O)$C_{1-4}$ alkyl, —NHC(=O)O$C_{1-4}$ alkyl, and —NHC(=O)NH$C_{1-4}$ alkyl;

t1 is 0;

t2 is 0; and t3 is 1.

2. The compound of claim 1, or a pharmaceutically acceptable salt thereof, wherein the moiety of Formula M-1 of Formula I

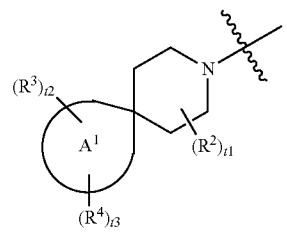
M-1 is a moiety of Formula M1-a:

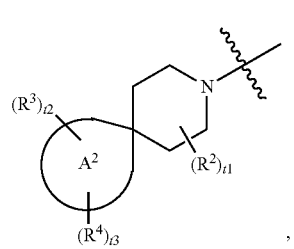
M-1a wherein ring A² is 5- or 6-membered heterocycloalkyl.

3. The compound of claim 1, or a pharmaceutically acceptable salt thereof, wherein the moiety of Formula M-1 of Formula I

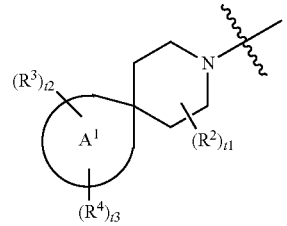
M-1 is a moiety of Formula M-1b, M-1c, M-1d, or M-1e:

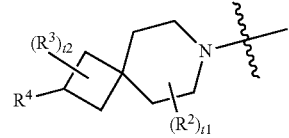
M-1b

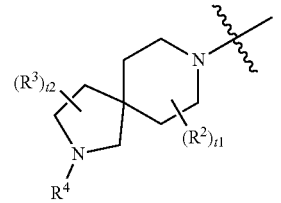
M-1c

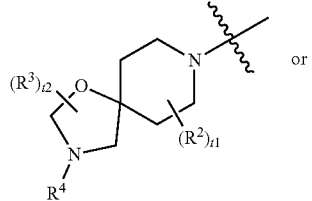
M-1d or

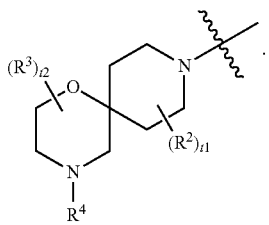

M-1e

4. The compound of claim 3, or a pharmaceutically acceptable salt thereof, wherein the moiety of Formula M-1 of Formula I is a moiety of Formula M-1b; and $R^4$ is selected from the group consisting of $R^6$, —N($R^5$)(C(=O)$R^6$), —N($R^5$)(S(=O)$_2R^6$), and —O$R^6$.

5. The compound of claim 3, or a pharmaceutically acceptable salt thereof, wherein the moiety of Formula M-1 of Formula I is a moiety of Formula M-1c; and $R^4$ is selected from the group consisting of $R^6$, —C(=O)—$R^6$, —S(=O)$_2R^6$, and —SO$_2$N$R^5R^6$.

6. The compound of claim 3, or a pharmaceutically acceptable salt thereof, wherein the moiety of Formula M-1 of Formula I is a moiety of Formula M-1d; and $R^4$ is selected from the group consisting of $R^6$, —N($R^5$)(C(=O)$R^6$), —N($R^5$)(S(=O)$_2R^6$), —C(=O)—$R^6$, —S(=O)$_2R^6$, —N$R^5R^6$, —SO$_2$N$R^5R^6$, and —O$R^6$.

7. The compound of claim 3, or a pharmaceutically acceptable salt thereof, wherein the moiety of Formula M-1 of Formula I is a moiety of Formula M-1e; and $R^4$ is selected from the group consisting of $R^6$, —C(=O)—$R^6$, —S(=O)$_2R^6$, and —SO$_2$N$R^5R^6$.

8. A compound of claim 1 selected from the group consisting of:
  1-[({4-[(4-fluorophenyl)sulfonyl]-1-oxa-4,9-diazaspiro[5.5]undec-9-yl}carbonyl)oxy]pyrrolidine-2,5-dione;
  N-[(3R)-8-{[(2,5-dioxopyrrolidin-1-yl)oxy]carbonyl}-1-oxa-8-azaspiro[4.5]dec-3-yl]-N-methylbenzenesulfonamide;
  1-cyclopropyl-N-[(3R)-8-{[(2,5-dioxopyrrolidin-1-yl)oxy]carbonyl}-1-oxa-8-azaspiro[4.5]dec-3-yl]-N-methylmethanesulfonamide; and
  1-{[(2-{[6-(difluoromethyl)pyridin-3-yl]oxy}-7-azaspiro[3.5]non-7-yl)carbonyl]oxy}pyrrolidine-2,5-dione,
or a pharmaceutically acceptable salt thereof.

9. A pharmaceutical composition comprising a compound or pharmaceutically acceptable salt according to claim 1, and a pharmaceutically acceptable carrier.

10. A method for inhibiting MAGL comprising contacting the MAGL with a compound or pharmaceutically acceptable salt according to claim 1.

11. The compound of claim 4, or a pharmaceutically acceptable salt thereof, wherein $R^4$ is $R^6$ or —O$R^6$; and $R^6$ is selected from the group consisting of phenyl and 5- to 6-membered heteroaryl, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

12. The compound of claim 5, or a pharmaceutically acceptable salt thereof, wherein $R^4$ is selected from the group consisting of $R^6$, —C(=O)—$R^6$, —S(=O)$_2R^6$, and —SO$_2$N$R^5R^6$.

13. The compound of claim 5, or a pharmaceutically acceptable salt thereof, wherein $R^4$ is —C(=O)—$R^6$.

14. The compound of claim 6, or a pharmaceutically acceptable salt thereof, wherein $R^4$ is selected from the group consisting of $R^6$, —N($R^5$)(C(=O)$R^6$), and —N($R^5$)(S(=O)$_2R^6$).

15. The compound of claim 14, or a pharmaceutically acceptable salt thereof, wherein $R^5$ is H or $C_{1-4}$ alkyl; and $R^6$ is selected from the group consisting of phenyl, 5- or 6-membered heteroaryl, and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

16. The compound of claim 6, or a pharmaceutically acceptable salt thereof, wherein $R^4$ is selected from the group consisting of —N($R^5$)(C(=O)$R^6$) and —N($R^5$)(S(=O)$_2R^6$); $R^5$ is H or $C_{1-4}$ alkyl; and $R^6$ is selected from the group consisting of phenyl, 5- or 6-membered heteroaryl, and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy.

17. The compound of claim 7, or a pharmaceutically acceptable salt thereof, wherein $R^4$ is —S(=O)$_2R^6$; and $R^6$ is selected from the group consisting of phenyl, 5- or 6-membered heteroaryl, and ($C_{3-10}$ cycloalkyl)-$C_{1-4}$ alkyl-, wherein each of the selections is optionally substituted with one or more substituents each independently selected from the group consisting of halogen, —CN, oxo, —OH, $C_{1-4}$ alkyl, $C_{1-4}$ haloalkyl, $C_{1-4}$ hydroxylalkyl, $C_{3-4}$ cycloalkyl, $C_{3-4}$ cycloalkyl-$C_{12}$ alkyl-, $C_{1-4}$ alkoxy, and $C_{1-4}$ haloalkoxy.

* * * * *